(12) United States Patent
Choi et al.

(10) Patent No.: US 7,977,373 B2
(45) Date of Patent: Jul. 12, 2011

(54) PRODRUGS OF ION CHANNEL MODULATING COMPOUNDS AND USES THEREOF

(75) Inventors: Lewis Siu Leung Choi, Burnaby (CA); Doug Ta Hung Chou, Vancouver (CA); Allen W. Davidoff, Calgary (CA); Adewale Eniade, Coquitlam (CA); Bertrand M. C. Plouvier, Vancouver (CA)

(73) Assignee: Cardiome Pharma Corp., Vancouver, British Columbia (CA)

(*) Notice: Subject to any disclaimer, the term of this patent is extended or adjusted under 35 U.S.C. 154(b) by 648 days.

(21) Appl. No.: 11/547,423

(22) PCT Filed: Mar. 31, 2005

(86) PCT No.: PCT/US2005/010878
§ 371 (c)(1),
(2), (4) Date: Sep. 30, 2008

(87) PCT Pub. No.: WO2005/113011
PCT Pub. Date: Dec. 1, 2005

(65) Prior Publication Data
US 2009/0105256 A1    Apr. 23, 2009

Related U.S. Application Data

(60) Provisional application No. 60/586,992, filed on Jul. 8, 2004, provisional application No. 60/559,405, filed on Apr. 1, 2004.

(51) Int. Cl.
A61K 31/405    (2006.01)
A61K 31/5377   (2006.01)
A61K 31/496    (2006.01)

(52) U.S. Cl. ............. 514/424; 514/254.01; 514/235.5; 514/227.8; 514/326

(58) Field of Classification Search ............ 514/424, 514/254.01, 235.5, 326, 227.8
See application file for complete search history.

(56) References Cited

U.S. PATENT DOCUMENTS

| | | | |
|---|---|---|---|
| 2,954,380 A | 9/1960 | Shapiro et al. | 260/268 |
| 3,218,328 A | 11/1965 | Shapiro et al. | 260/294 |
| 4,145,435 A | 3/1979 | Szmuszkovicz | 424/274 |
| 4,179,501 A | 12/1979 | Szmuszkovicz | 424/226 |
| 4,188,403 A | 2/1980 | Orth et al. | 424/330 |
| 4,598,087 A | 7/1986 | Horwell | 514/429 |
| 4,656,182 A | 4/1987 | Horwell | 514/324 |
| 4,663,343 A | 5/1987 | Horwell et al. | 514/429 |
| 4,684,728 A | 8/1987 | Möhring et al. | 544/182 |
| 4,855,316 A | 8/1989 | Horwell et al. | 514/422 |
| 4,880,800 A | 11/1989 | Wallis et al. | 514/211 |
| 4,906,655 A | 3/1990 | Horwell et al. | 514/422 |
| 5,019,588 A | 5/1991 | Horwell et al. | 514/409 |
| 5,051,428 A | 9/1991 | Horwell et al. | 514/320 |
| 5,059,620 A | 10/1991 | Stout et al. | 514/422 |
| 5,492,825 A | 2/1996 | Jan et al. | 435/240.2 |
| 5,506,257 A | 4/1996 | MacLeod et al. | 514/422 |
| 5,637,583 A | 6/1997 | MacLeod et al. | 514/212 |
| 5,670,335 A | 9/1997 | Jan et al. | 435/29 |
| 5,728,535 A | 3/1998 | Lester et al. | 435/7.2 |
| 5,734,021 A | 3/1998 | Lester et al. | 530/350 |
| 5,750,537 A | 5/1998 | Nomura et al. | 514/304 |
| 5,817,698 A | 10/1998 | Brown et al. | 514/646 |
| 5,885,984 A | 3/1999 | MacLeod et al. | 514/211 |
| 6,174,879 B1 | 1/2001 | MacLeod et al. | 514/212.01 |
| 6,180,632 B1 | 1/2001 | Myers et al. | 514/252.1 |
| 6,210,809 B1 | 4/2001 | Okutomi et al. | 428/546 |
| 6,214,810 B1 | 4/2001 | Fermini et al. | 514/75 |
| 6,451,819 B2 | 9/2002 | Alanine et al. | 514/326 |
| 6,521,619 B2 | 2/2003 | Link et al. | 514/237.2 |
| 6,649,603 B2 | 11/2003 | Sum | 514/210.01 |
| 6,979,685 B1 | 12/2005 | Beatch et al. | 514/231.2 |
| 7,053,087 B1 | 5/2006 | Beatch et al. | 514/237.8 |
| 7,057,053 B2 * | 6/2006 | Beatch et al. | 548/541 |
| 7,101,877 B2 * | 9/2006 | Bain et al. | 514/231.2 |
| 7,259,184 B2 | 8/2007 | Beatch et al. | 514/424 |
| 7,345,086 B2 | 3/2008 | Beatch et al. | 514/424 |
| 7,345,087 B2 | 3/2008 | Beatch et al. | 514/424 |
| 7,507,545 B2 | 3/2009 | Fedida et al. | 435/7.2 |
| 7,524,879 B2 | 4/2009 | Beatch et al. | 514/424 |
| 7,534,790 B2 * | 5/2009 | Bain et al. | 514/231.2 |
| 2003/0073617 A1 | 4/2003 | Li et al. | 514/2 |

(Continued)

FOREIGN PATENT DOCUMENTS

CA    1234808    4/1988

(Continued)

OTHER PUBLICATIONS

Wu and Farrelly, Toxicology 236:1-6, 2007.*
Vippagunta et al., Advanced Drug Delivery Reviews, vol. 48, p. 3-26 (on p. 3), 2001.*
Tsai et al. Biotechnol. Prog. 1997, vol. 13, p. 82-88.*
Adcock et al., "RSD931, a novel anti-tussive agent acting on airway sensory nerves", *Br J Pharm* 138(3):407-416, 2003.
Altria et al., "Capillary Electrophoresis as a Routine Analytical Tool in Pharmaceutical Analysis", *LCGC* 19(9): 972-985, Sep. 2001.

(Continued)

*Primary Examiner* — Yong Chu
(74) *Attorney, Agent, or Firm* — Seed IP Law Group PLLC

(57) ABSTRACT

Prodrugs of ion channeling modulating compounds, including, for example, prodrugs of the ion channel modulating compound of the following formula: are described herein, as well as methods of making and using such prodrugs and pharmaceutical compositions containing such prodrugs.

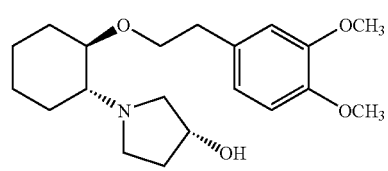

9 Claims, No Drawings

U.S. PATENT DOCUMENTS

| | | | |
|---|---|---|---|
| 2003/0130170 A1 | 7/2003 | Li et al. | 514/2 |
| 2005/0002693 A1 | 1/2005 | Pak et al. | 399/165 |
| 2005/0038256 A1 | 2/2005 | Barrett et al. | 546/236 |
| 2005/0070552 A1 | 3/2005 | Fedida et al. | 514/255.06 |
| 2006/0252753 A1 | 11/2006 | Beatch et al. | 514/237.8 |
| 2007/0099983 A1 | 5/2007 | Barrett et al. | 514/408 |
| 2007/0190156 A1 | 8/2007 | Beatch et al. | 424/489 |
| 2007/0197632 A1 | 8/2007 | Beatch et al. | 514/327 |
| 2007/0254945 A1 | 11/2007 | Jung et al. | 514/424 |
| 2009/0088464 A1 | 4/2009 | Choi et al. | 514/424 |
| 2010/0029639 A1 | 2/2010 | Bain et al. | 514/233.5 |
| 2010/0056603 A1 | 3/2010 | Beatch et al. | 514/424 |

FOREIGN PATENT DOCUMENTS

| | | |
|---|---|---|
| CA | 1235122 | 4/1988 |
| CA | 1243020 | 10/1988 |
| CA | 2004575 | 6/1990 |
| CA | 2058502 | 6/1993 |
| CA | 2172513 | 3/1995 |
| CA | 2244209 A1 | 7/1997 |
| CA | 2008391 | 12/1997 |
| CA | 2289055 A1 | 1/1999 |
| CA | 2268590 A1 | 10/2000 |
| CA | 2132841 | 3/2001 |
| DE | 2 259 260 | 6/1974 |
| DE | 2 658 401 | 7/1978 |
| DE | 3 517 901 A1 | 12/1985 |
| EP | 0 014 263 B1 | 8/1980 |
| EP | 222533 A1 | 5/1987 |
| EP | 147085 B1 | 3/1990 |
| EP | 372466 A2 | 6/1990 |
| EP | 380063 B1 | 8/1990 |
| EP | 0 546 583 A1 | 6/1993 |
| EP | 552386 A1 | 7/1993 |
| EP | 720605 BI | 7/1996 |
| HU | 215963 B | 2/1995 |
| JP | 02-270864 | 11/1990 |
| WO | WO 93/19056 | 9/1993 |
| WO | WO 94/07843 A1 | 4/1994 |
| WO | WO 94/14435 A1 | 7/1994 |
| WO | WO 95/08544 A1 | 3/1995 |
| WO | WO 95/28155 A1 | 10/1995 |
| WO | WO 96/18615 A1 | 6/1996 |
| WO | WO 96/23894 A1 | 8/1996 |
| WO | WO 97/32857 A1 | 9/1997 |
| WO | WO 97/49680 A1 | 12/1997 |
| WO | WO 98/40055 A2 | 9/1998 |
| WO | WO 99/02159 A1 | 1/1999 |
| WO | WO 99/03468 A1 | 1/1999 |
| WO | WO 99/11252 A2 | 3/1999 |
| WO | WO 99/16431 A1 | 4/1999 |
| WO | WO 99/50205 A2 | 10/1999 |
| WO | WO 99/50225 A1 | 10/1999 |
| WO | WO 99/53908 A2 | 10/1999 |
| WO | WO 9950225 A1 * | 10/1999 |
| WO | WO 00/23023 A1 | 4/2000 |
| WO | WO 00/47547 A2 | 8/2000 |
| WO | WO 00/51981 A1 | 9/2000 |
| WO | WO 01/96335 A1 | 12/2001 |
| WO | WO 02/18334 A1 | 3/2002 |
| WO | WO 03/105756 A2 | 12/2003 |
| WO | WO 2004/008103 A2 | 1/2004 |
| WO | WO 2004/014973 A2 | 2/2004 |
| WO | WO 2004/082585 A2 | 9/2004 |
| WO | WO 2004/098525 A2 | 11/2004 |
| WO | WO 2004/099137 A1 | 11/2004 |
| WO | WO 2005/018635 A2 | 3/2005 |
| WO | WO 2005/094897 A2 | 10/2005 |

OTHER PUBLICATIONS

Alzheimer's Disease Information Page [online], [retrieved on Oct. 3, 2006]. Retrieved from the Internet, URL: <http://www.ninds.nih.gov/disorders/alzheimersdisease/alzheimersdisease.htm>.

Amin et al., "RPR 101821, a New Potent Cholesterol-lowering Agent. Inhibition of Squalene Synthase and 7-Dehydrocholesterol Reductase", *Naunyn-Schmiedeberg's Arch Pharmacol* 353:233-240, 1996.

Asensio et al., "Epoxidation of Primary and Secondary Alkenylammonium Salts with Dimethyldioxirane, Methyl(trifluoromethyl)dioxirane, and *m*-Chloroperbenzoic Acid. A General Synthetic Route to Epoxyalkylamines", *J. Org. Chem.* 60(12): 3692-3699, 1995.

Atwell and Denny, "Monoprotection of $\alpha,\omega$-Alkanediamines with the *N*-Benzyloxycarbonyl Group," *Synthesis*: 1032-1033 + Errata and Addenda, Dec. 1984.

Bain et al., "Better Antiarrhythmics? Development of Antiarrhythmic Drugs Selective for Ischaemia-Dependent Arrhythmias", *Drug Development Research* 42:198-210, 1997.

Bakalarz-Jeziorna et al., "Synthesis of multifunctionalized phosphonic acid esters via opening of oxiranes and azetidinium salts with phosphoryl-substituted carbanions", *J. Chem. Soc., Perkin Trans.* 1: 1086-1090, 2001.

Barrett and Walker, "Glibenclamide Possesses Transient, Ischaemia Selective Class III Antiarrhythmic Actions But Does Not Prevent Ischaemic Arrhythmias", *BPS Proceedings* 116P, 1996.

Barrett et al., "A Model of Myocardial Ischemia for the Simultaneous Assessment of Electrophysiological Changes and Arrhythmias in Intact Rabbits", *J Pharmacol Toxicol Methods* 37(1):27-36, 1997.

Barrett et al., "Ischaemia selectivity confers efficacy for suppression of ischaemia-induced arrhythmias in rats", *Eur J Pharm* 398:365-374, 2000.

Barrett et al., "Atypical Dose Response Curves for Antiarrhythmic Drugs", *BPS Proceedings* 115P, 1996.

Barrett, "Ischemia Selective Electrophysiological and Antiarrhythmic Actions of RSD1019 in Ischemic Cardiac Tissue", *J Mol Cell Cardiol* 29:197, 1997.

Barrett et al., "RSD1019 suppresses ischaemia-induced monophasic action potential shortening and arrhythmias in anaesthetized rabbits", *Br J Pharm* 131(3):405-414, 2000.

Beatch et al., "RSD1235 Selectively Prolongs Atrial Refractoriness and Terminates AF in Dogs with Electrically Remodelled Atria", *Pharmacologist* 44(2) (Supp I), A15: XIVth World Congress of Pharmacology: Meeting Abstracts, 2002. Abstract No. 22.11.

Beatch et al., "Effect of a Novel Anti-tussive Compound CP1 Against Citric Acid Induced Cough in Guinea-Pigs", *Proc West Pharmacol Soc* 44:252, 2001.

Beatch et al., "RSD1235 Rapidly and Effectively Terminates Atrial Fibrillation", Abstract submission ESC Congress Aug. 30-Sep. 3, 2003, in Vienna, Austria.

Beatch et al., "RSD1235, A Novel Atrial-Selective Antiarrhythmic Drug, Shows Rapid and Extensive Oral Absorption in Man", 12th International Congress on Cardiovascular Pharmacotherapy, May 7-10, 2003, Barcelona, Spain.

Beatch et al., "Ventricular Fibrillation, an Uncontrolled Arrhythmia Seeking New Targets", *Drug Develop Res* 55:45-52, 2002.

Beatch, "Antihistamine-induced Ventricular Arrhythmias", *BPS Proceedings* 120P, 1996.

Beatch et al., "Characterization of a Non-Human Primate Model of Drug-Induced Torsades De Pointes", *Proc West Pharmacol Soc* 40:13-16, 1997.

Beatch et al., "RSD1235 Selectively Prolongs Atrial Refractoriness and Terminates AF in Dogs with Electrically Remodelled Atria", *PACE* 24(Part II):698. Abstract 702, May 10, 2002.

Bian et al., "Effects of Kappa-opioid receptor stimulation in the heart and the involvement of protein kinase C", *Brit J Pharm* 124:600-606, 1998.

Billman, "RSD-1235", *Curr Opin Investigational Drugs* 4(3):352-354, 2003.

Bogatskii et al., "Effect of Polymethylene- and Polyhydroxyethylene-bis-(2-Amino-1,3-Diazepinium) Iodides on Cell and Model Membranes," *Byulleten' Éksperimental'noi Biologii i Meditsiny* 94(8): 52-54, Aug. 1982 [English translation included from the Department of Chemistry of Macrocyclic Complexones, Physicochemical Institute, Academy of Sciences of the Ukrainian SSR, Odessa, pp. 1071-1074.].

Boiadjiev and Lightner, "pH-Sensitive Exciton Chirality Chromophore. Solvatochromic Effects on Circular Dichroism Spectra", *Tetrahedron: Asymmetry* 7(10):2825-2832, 1996.

Bouvier et al., "A new paclitaxel prodrug for use in ADEPT strategy," *Org. Biomol. Chem.* 1: 3343-3352, 2003.

Bowen et al., "Characterization of the Enantiomers of cis-N-[2-(3,4-Dichlorophenyl)Ethyl]-N-Methyl-2-(1-Pyrrolidinyl)Cyclohexylamine (BD737 and BD738): Novel Compounds with High Affinity, Selectivity and Biological Efficacy at Sigma Receptors", *J Pharmacol Exp Ther* 262(1):32-40, 1992.

Bursi et al., "Structure-activity relationship study of human liver microsomes-catalyzed hydrolysis rate of ester prodrugs of MENT by comparative molecular field analysis (CoMFA)," *Steroids* 68: 213-220, 2003.

Cardiome Pharma Corp. (Jan. 31, 2001). "Nortran Drug Effective in Atrial Arrhythmia Model" (http://cardiome.com/wordpress/?p=104). Press Release.

Cardiome Pharma Corp. (Jun. 21, 2001). "Nortran Antiarrhythmia Drug Demonstrates Oral Bioavailability" (http://cardiome.com/wordpress/?p=99). Press Release.

Cardiome Pharma Corp. (Jul. 30, 2001). "Cardiome Pharma Completes Phase I Safety Study" (http://cardiome.com/wordpress/?p=97). Press Release.

Cardiome Pharma Corp. (Jan. 17, 2002). "Cardiome Reports Dosing of First Patient in Pivotal Phase II Study" (http://cardiome.com/wordpress/?p=90). Press Release.

Cardiome Pharma Corp. (Sep. 3, 2002). "Cardiome Drug Effective for Heart Patients" (http://cardiome.com/wordpress/?p=75). Press Release.

Cardiome Pharma Corp. (Dec. 5, 2002). "Cardiome Reports Oral Absorption of RSD1235 in Humans" (http://cardiome.com/wordpress/?p=72). Press Release.

Cardiome Pharma Corp. (Dec. 20, 2004). "Cardiome's Pivotal AF Study Achieves Primary Endpoint" (http://cardiome.com/wordpress/?p=14). Press Release.

Cardiome Pharma Corp. (Feb. 4, 2005). "Cardiome Reports Additional ACT 1 Clinical Results" (http://cardiome.com/wordpress/?p=2). Press Release.

Cardiome Pharma Corp. (Apr. 25, 2005). "Cardiome Successfully Completes Second Phase 1 Trial" (http://cardiome.com/wordpress/?p=230). Press Release.

Cardiome Pharma Corp. (Aug. 31, 2005). "Cardiome Successfully Completes RSD1235 Oral Phase 1 Trial" (http://cardiome.com/wordpress/?p=255). Press Release.

Cardiome Pharma Corp. (Sep. 29, 2005). "Cardiome and Astellas Announce Positive Results from Second Phase 3 Trial" (http://cardiome.com/wordpress/?p=262). Press Release.

Cardiome Pharma Corp. (May 5, 2006). "Cardiome Reports Additional Phase 1. Trial Data for Oral RAD1235" (http://cardiome.com/workpress/?p=291). Press Release Cardiome Pharma Corp. (Jul. 24, 2006). "Cardiome Announces Interim Phase 2A Results for Oral RSD1235" (http://cardiome.com/wordpress/?p=312). Press Release.

Cardiome Pharma Corp. (Sep. 13, 2006). "Cardiome Announces Positive Phase 2A Results for Oral RSD1235" (http://cardiome.com/wordpress/?p=321). Press Release.

Cardiome Pharma Corp. Healthcare (Underweight) Company Report Dec. 12, 2002. 26 pages.

Carmeliet and Mubagwa, "Antiarrhythmic drugs and cardiac ion channels: mechanisms of action", *Progress in Biophysics & Molecular Biology* 70: 1-72, 1998.

Clohs and Wong, "Validation of a capillary electrophoresis assay for assessing the metabolic stability of verapamil in human liver microsomes", *J Cap Elec & Microchip Tech* 007(5/6):113-117, 2002.

Clohs, "Capillary Electrophoresis and Its Applications in the Pharmaceutical Industry—Short Course: One Platform Fits Many Applications", CCS 2002, 52 pages.

Clohs, "Capillary Electrophoresis as an Analytical Tool in the Drug Discovery Process", Presentation CE Symposium, Aug. 2000, 40 pages.

Clohs, "The Versatility of CE for Drug Pharmacokinetics and Metabolism Studies", CE in the Biotechnology & Pharmaceutical Industries (Symposium), Boston, Aug. 2001, 46 pages.

Clohs, "Pharmacokinetics profiling of new drug candidates: a key process in drug discovery", *Beckman Coulter P/ACE Setter* 4(1):6, Jun. 2000.

Clohs and Winstanley, "CE Analysis of Propranolol in Human Serum Using Dynamic Capillary Coating", *CE Currents: LCGS Europe*, Reader Service 14, pp: 289-293, May 2002.

Clohs, "Bio-Analytical Applications of Capillary Electrophoresis in a Drug Discovery Setting", CSC Seminar, Jun. 5, 2002, 29 pages.

Clohs, "CE and Drug Metabolism Studies: A Powerful Combination in Drug Discovery", CE in the Biotechnology and Pharmaceutical Industries (Symposium), Washington, DC, Aug. 2002, 31 pages.

Comley et al., "Antipneumocystis Activity of 17C91, a Prodrug of Atovaquone," *Antimicrobial Agents and Chemotherapy* 39(10): 2217-2219, Oct. 1995.

Crotti et al., "Regiochemical control of the ring-opening of epoxides by means of chelating processes Part 13 . . . ", Chemical Abstracts 129(17):662-663, Abstract No. 216472k, 1998.

Crotti et al., "Synthesis and Ring-Opening Reactions of the Diastereoisomeric cis- and trans-Epoxides Derived from 3-(Benzyloxy)cyclopentene and 2-(Benzyloxy)-2,5-dihydrofuran", *Eur J Org Chem* 8:1675-1686, 1998.

Curtis and Walker, "Quantification of arrhythmias using scoring systems: an examination of seven scores in an in vivo model of regional myocardial ischaemia", *Cardiovascular Research* 22: 656-665, 1988.

De Costa et al., "Synthesis and Evaluation of N-Substituted cis-N-Methy1-2-(1-pyrrolidinyl)cyclohexylamines as High Affinity σ Receptor Ligands. Identification of a New Class of Highly Potent and Selective σ Receptor Probes", *J Med Chem* 33:3100-3110, 1990.

De Groot et al., "Elongated Multiple Electronic Cascade and Cyclization Spacer Systems in Activatible Anticancer Prodrugs for Enhanced Drug Release," *J. Org. Chem.* 66: 8815-8830, 2001.

Doci et al., "Local Anesthetic Effects of Intradermal RSD921 in Healthy Subjects", Proceedings of the 100th Annual Meeting of the American Society for Clinical Pharmacology and Therapeutics, San Antonio, Texas, Mar. 18-20, 1999, Abstract PIII-2 in *Clin Pharm & Therap* 65(2):177, Feb. 1999.

Duan et al., "Potassium Channel Blocking Properties of Propafenone in Rabbit Atrial Myocytes", *J Pharm Exp Ther* 264(3): 1113-1123, 1993.

Ezrin et al., "Safety and Pharmacokinetics of RSD1235, a Novel Atrial Fibrillation Converting Drug, in Healthy Volunteers", Abstracts: 11th Int. Congress Cardiovasc. Pharmacother. 16 Abstract P297, 2002.

Ezrin et al., "A Dose-Ranging Study of RSD1235, A Novel Antiarrhythmic Agent, in Healthy Volunteers", Pharmacologist, 44(2) (Supplement I), A15: XIVth World Congress of Pharmacology: Meeting Abstracts, 2002. Abstract No. 22.10.

Fedida et al., " Kv1.5 is an Important Component of Repolarizing $K^+$ Current in Canine Atrial Myocytes", Circulation Research Peer Review Plus Manuscript PDF, 38 pages, 2002.

Florent et al., "Prodrugs of Anthracyclines for Use in Antibody-Directed Enzyme Prodrug Therapy," *J. Med. Chem.* 41: 3572-3581, 1998.

Franciosi et al., "Phase II Clinical Trial of RSD921 as a Local Anaesthetic in Patients Undergoing Venous Cannulation for Elective Treatment", in Proceedings of the 28th Annual ACCP Meeting Abstract 32, p. 977, Feb. 2000.

Franciosi and McLarnon, "pH-dependent blocking actions of three novel antiarrhythmic compounds on $K^+$ and $Na^+$ currents in rat ventricular myocytes", *Eur J Pharm* 425:95-107, 2001.

Franqueza et al., "Effects of propafenone and 5-hydroxy-propafenone on hKv1.5 channels", *Br J Pharm* 125:969-978, 1998.

Friess et al., "Central Activity Evoked in the Cat by Cis-Trans Isomers of 1,2-Aminocyclohexanol Dervivatives", *Taxicol Appl Pharmacol* 3:638-653, 1961.

Fuchs et al., "Synthesen und biologische Aktivitäten von Derivaten des thyrotropin-releasing-Hormons (TRH) mit ω-Aminoalkylresten am Prolinamidstickstoff," *Liebigs Ann. Chem.*: 602-608, 1977.

Geiger, "Synthese eines Heptadecapeptids mit hoher adrenocorticotroper Wirkung," *Liebigs Ann. Chem.* 750: 165-170, 1971.

Ginrich et al., "A New Class of Potent Vascular Endothelial Growth Factor Receptor Tyrosine Kinase Inhibitors: Structure-Activity Relationships for a Series of 9-Alkoxymethyl-12-(3-hydroxypropyl)indeno[2,1-α]pyrolo[3,4-c]carbazole-5-ones and the Identification of CEP-5214 and its Dimethylglycine Ester Prodrug Clinical Candidate CEP-7055," *J. Med. Chem.* 46:5375-5388, 2003.

Grant, "Mechanisms of Atrial Fibrillation and Action of Drugs Used in its Management", *Am J Cardiol* 82:43N-49N, Oct. 16, 1998.

Graul et al., "Methylprednisolone Suleptanate," *Drugs of the Future* 22(8): 833-840, 1997.

Halfpenny et al., "Highly Selective k-Opioid Analgesics. 3. Synthesis and Structure-Activity Relationships of Novel N-[2-(1-Pyrrolidiny1)-4-or-5-substituted-cyclohexyl]arylacetamide Derivatives", *J Med Chem* 33:286-291, 1990.

Halfpenny et al., "Highly Selective k-Opioid Analgesics. 2. Synthesis and Structure-Activity Relationships of Novel N-[(2-Aminocyclohexyl)aryl]acetamide Derivatives", *J Med Chem* 32:1620-1626, 1989.

Hansen et al., "Partially Protected Polyamines," *Synthesis*: 404-405, May 1982.

Hayes et al., "RSD 992 Enhances Erection and Copulation in Rats and Erection in Primates", *Int J Impotence Res* p. 189 (Abstract P24), 1996.

Hayes et al., "Actions of Arylpiperazines on Corpus Cavernosum Smooth Muscle in Vitro", *Asia Pac J Pharmacol* 12:97-103, 1997.

Hayes et al., "Direct Actions of Arylpiperazines on Rabbit and Human Corpus Caversonal Smooth Muscle in Vitro", *Asia Pac J Pharmacol*, Abstract S15, 1997.

Herrin et al., "Antimalarials. Synthesis and Antimalarial Activity of 1-(4-Methoxycinnamoy1)-4-(5-phenyl-4-oxo-2-oxazolin-2-yl)piperazine and Derivatives," *Journal of Medicinal Chemistry* 18(12): 1216-1223, 1975.

Hesketh et al., "Safety of RSD1235 in a rabbit Purkinje fiber model", in Proceedings of the XIVth World Congress of Phar. Meeting, Abstract No. 22.12, 2002.

Hou et al., "Synthesis of novel and enantiomerically pure epoxypropylamine: a divergent route to the chiral β-adrenergic blocking agents", *Tetrahedron: Asymmetry* 10: 2319-2326, 1999.

Houssin et al., "A Convenient and General Method for the Preparation of *tert*-Butoxycarbonylaminoalkanenitriles and Their Conversion to Mono-*tert*-butoxycarbonlalkanediamines," *Synthesis*: 259-261, Mar. 1988.

Howard and Walker, "Electrical Stimulation Studies with Quinacainol, a Putative 1C Agent, in the Anaesthetised Rat", *Proc. West. Pharmacol. Soc.* 33: 123-127, 1990.

Iwasaki et al., "Chemo- and Stereoselective Monobenzoylation of 1,2-Diols Catalyzed by Organotin Compounds", *J. Org. Chem.* 65(4): 996-1002, 2000.

Keefe et al., "New Antiarrhythmic Drugs: Their Place in Therapy", *Drugs* 22:363-400, 1981.

Kertesz et al., "The Electrophysiological and Antiarrhythmic Actions of RSD Analogs of U50,488H in Rats", in Proceedings of the West Pharmacol Soc. 9 pages, 1994.

Knorr et al., "New Coupling Reagents in Peptide Chemistry," *Tetrahedron Letters* 30(15): 1927-1930, 1989.

Lang et al., "Clinical Evaluation of RSD921 As a Local Anaesthetic in Patients Undergoing Venous Cannulation for Elective Treatment", *Clin Pharm & Therapeutics*, p. 142, Feb. 2000. Abstract PIII-1.

Lewis et al., "Enzyme inhibition during the conversion of squalene to cholesterol", *Steroids* 60:475-483, Jul. 1995.

Li et al., "Adrenergic Modulation of Ultrarapid Delayed Rectifier $K^+$ Current in Human Atrial Myocytes", *Circ Res* 78(5):903-915, May 1996.

Malayev et al., "Mechanism of Clofilium Block of the Human Kv1.5 Delayed Rectifier Potassium Channel", *Mol Pharm* 47:198-205, 1995.

Martens et al., "Einfache Synthese neuer anellierter Pyrrole", *J Synth Org Chem* 12:965-967, Dec. 1989.

Mátyus et al., "Antiarrhythmic Agents: Current Status and Perspectives", *Medicinal Research Reviews* 17(5):427-451, 1997.

McLarnon et al., "Mixed Block of $K^+$ and $Na^+$ Currents by KC8851, A Structural Analogue of Tedisamil in Vitro and in Vivo Studies", *BPS Proceedings* 114P, 1996.

Moorman et al., "$pK_a$ Does Not Predict pH Potentiation of Sodium Channel Blockade by Lidocaine and W6211 in Guinea Pig Ventricular Myocardium", *The Journal of Pharmacology and Experimental Therapeutics* 238(1):159-166, 1986.

Morisawa et al., "Preparation of fluorocarbocyclic nucleosides as antitumor agents", Chemical Abstracts 115(5):904-905, abstract No. 50215n, 1991.

Nakashima et al., "Angiotensin II Type I Receptor Antagonist Prevents the Promotion of Atrial Fibrillation", *PACE* 24(Part II):698, May 10, 2002. Abstract 701.

Nattel et al., "Effects of the novel antiarrhythmic agent azimilide on experimental atrial fibrillation and atrial electrophysiologic properties", *Cardiovascular Research* 37:627-635, 1998.

Nattel et al., "RSD1235: a novel antiarrhythmic agent with a unique electrophysiological profile that terminates AF in dogs", *Eur Heart J* 22(Suppl):448 (Abstract P2362), 2001.

Nattel, "Experimental evidence for proarrhythmic mechanisms of antiarrhythmic drugs", *Cardiovascular Research* 37:567-577, 1998.

Nattel et al., "The Role of Channel Opening in Transient Outward Current Block by Quinidine, Flecainide, and 4-Aminopyridine in Human Atrial Myocytes", K Channels II: Regulation and Block, Abstract No. Tu-Pos403, 1994.

Nishi et al., "Studies on 2-Oxoquinoline Derivatives as Blood Platelet Aggregation Inhibitors. IV. Synthesis and Biological Activity of the Metabolites of 6-[4-(1-Cyclohexy1-1H-5-tetrazolyl)butoxy]-2-oxo-1,2,3,4-tetrahydroquinoline (OPC-13013)", *Chem Pharm Bull* 33(3):1140-1147, 1985.

Orth et al., "Cyclopentane-1-amines", Chemical Abstracts 89(15):555, Abstract No. 129113f, 1978.

Orth et al., "The Novel AF Conversion Agent RSD1235 Preferentially Blocks a Late Component of the Human Heart (hH1) $Na^+$ Current Active During Repolarization", EP Abstracts Oct. 3, 2003.

Page, "Beta-Blockers for Atrial Fibrillation: Must We Consider Asymptomatic Arrhythmias?", *Journal of the American College of Cardiology* 36(1): 147-150, Jul. 2000.

Paggiaro, "Methylprednisolone suleptanate Pharmacia Corp," *Current Opinion in Investigational Drugs* 1(1): 97-103, 2000.

Panfilov et al., "Reactions of Sodium Borohydride in Acetic Acid: Reductive Amination of Carbonyl Compounds", *Pharmaceutical Chemistry Journal* 34(7): 371-373, 2000.

Plouvier et al., "Synthesis and Structure Activity Relationships of a Series of 2- Aminocyclohexyl . . . as Potential Ischaemia Selective Ventricular Antiarrhythmics", BMPS 994.

Pugsley and Goldin, "Molecular analysis of the $Na^+$ channel blocking actions of the novel class I antiarrhythmic", *Br J Pharm* 127:9-18, 1999.

Pugsley et al., "A Characterization of the Antiarrhythmic and Electrophysiological Properties of RSD992, A Novel Arylpiperazine Drug", XIVth World Congress of Pharmacology: Meeting Abstract 22.8, in Pharmacologist 44(2, Supp 1):A15, 2002.

Pugsley et al., "Electropharmacology of Two New Class 1 agents", Heart and Stroke Annual Conference, p. 12, 1995.

Pugsley et al., "Sodium Channel-Blocking Properties of Spiradoline, a Kappa Receptor Agonist, are Responsible for Its Antiarrhythmic Action in the Rat", *J Cardiovas Pharmacol* 32:863-874, 1998.

Pugsley et al., "Are the arrhythmias due to myocardial ischaemia and infarction dependent upon the sympathetic system?", *Cardiol Res* 43:830-831, 1999.

Rautio et al., "Synthesis and in Vitro Evaluation of Novel Morpholinyl- and Methylpiperazinylacyloxyalkyl Prodrugs of 2-(6-Methoxy-2-naphthyl)propionic Acid (Naproxen) for Topical Drug Delivery," *J. Med. Chem.* 43: 1489-1494, 2000.

Ribeiro et al., "Determination of RSD921 in human plasma by high-performance liquid chromatography-tandem mass spectrometry using tri-deuterated RSD921 as internal standard: application to a phase I clinical trial", *J Mass Spectrom* 36:1133-1139, 2001.

Rich et al., "Quinidine Block of the Human Cardiac hKv1.5 Channel in Inside-Out Patches, K Channels II: Regulation and Block", Abstract No. Tu-Pos404, p. A209, 1999.

Roden and George, "The Cardiac Ion Channels: Relevance to Management of Arrhythmias", *Annu Rev Med* 47:135-148, 1996.

Roy et al., "RSD1235 Rapidly and Effectively Terminates Atrial Fibrillation", *Eur Heart J*, p. 3699, 2003.

Rynbrandt et al., "Cis-1-[2-(p-Anisidinomethyl)cyclohexyl]piperidine and Related Compounds. Oral Hypoglycemic Agents", *J Med Chem* 14(10): 985-987, 1971.

Saari et al., "Cyclization-Activated Prodrugs. Basic Carbamates of 4-Hydroxyanisole," *J. Med. Chem.* 33: 97-101, 1990.

Sanguinetti, "Modulation of Potassium Channels by Antiarrhythmic and Antihypertensive Drugs", *Hypertension* 19(3):228-236, Mar. 1992.

Schultz, "Prodrugs of Biologically Active Phosphate Esters," *Bioorganic & Medicinal Chemistry* 11: 885-898, 2003.

Singh, "Antiarrhythmic Drugs: A Reorientation in Light of Recent Developments in the Control of Disorders of Rhythm", *Am J Cardiol* 81(6A):3D-13D, Mar. 19, 1998.

Singh, "Atrial Fibrillation: Epidemiologic Considerations and Rationale for Conversion and Maintenance of Sinus Rhythm", *J Cardiovasc Pharmacol Therapeut* 8(Supp 1):S13-S26, 2003.

Snyders et al., "A Rapidly Activating and Slowly Inactivating Potassium Channel Cloned from Human Heart", *J. Gen. Physiol.* 101:513-543, Apr. 1993.

Snyders and Yeola, "Determinants of Antiarrhythmic Drug Action—Electrostatic and Hydrophobic Components of Block of the Human Cardiac hKv1.5 Channel", *Circ Res* 77(3):575-583, Sep. 19951.

Sohma et al., "Development of Water-Soluble Prodrugs of the HIV-1 Protease Inhibitor KNI-727: Importance of the Conversion Time for Higher Gastrointestinal Absorption of Prodrugs Based on Spontaneous Chemical Cleavage," *J. Med. Chem.* 46: 4124-4135, 2003.

Srilatha et al., "Alterations in Rabbit Corpus Cavernosal Pharmacology by High Cholesterol Diet", *Asia Pac J Pharmacol*, Abstract S15, 1997.

Steinbeck, "Proarrhythmische Wirkungen von Antiarrhythmika—Theoretische and Klinische Aspekte", *Z Kardiol* 81(Supp 4):139-143, 1992.

Stevenson, "Atrial Fibrillation and Heart Failure—Five More Years", *N. Engl J Med* 351(23):2437-2440, Dec. 2, 2004.

Tong et al., "Determination of an arylether antiarrhythmic and its N-dealkyl metabolite in rat plasma and hepatic microsomal incubates using liquid chromatography-tandem mass spectrometry", *J Chromatog B* 759:259-266, 2001.

Valenzuela et al., "Comparative effects of nonsedating histamine $H_1$ receptor antagonists, ebastine and terfenadine, on human Kv1.5 channels", *Eur J Pharm* 326:257-263, 1997.

Valenzuela et al., "Effects of Ropivacaine on a Potassium Channel (hKv1.5) Cloned from Human Ventricle", *Anesthesiology* 86:718-728, 1997.

Walker, "Antiarrhythmic Drug Development—Illusion and Disillusion?", *Drug Develop Res* 55:1-2, 2002.

Walker et al., "Determination of an arylacetamide antiarrhythmic in rat blood and tissues using reversed-phase high-performance liquid chromatography", *J Chromatog B* 675:257-263, 1996.

Walker et al., "Increased Electrophysiological Activity in Raised $K^+$ and low pH Improves Antiarrhythmic Efficacy for a Group of Morpholinocyclohexyl Derivatives", *BPS Proceedings* 118P, 1996.

Walker and Guppy, "Targeting Ischemic Ventricular Arrhythmias", Cardiac Drug Development Guide, Humana Press Inc., Totowa, NJ, pp. 175-201, 2003.

Wang et al., "Effects of Flecainide, Quinidine, and 4-Aminopyridine on Transient Outward and Ultrarapid Delayed Rectifier Currents in Human Atrial Myocytes", *J Pharm Exp Ther* 272(1):184-196, 1995.

Wang et al., "Sustained Depolarization-Induced Outward Current in Human Atrial Myocytes", *Circ Res* 73(6):1061-1076, Dec. 1993.

Wat et al., "Effects of Arylbenzacetamides on Neuromuscular Preparation", *Proc West Pharmacol Soc* 1994.

Wolf et al., "Impact of Atrial Fibrillation on Mortality, Stroke, and Medical Costs", *Arch Intern Med* 158: 229-234, Feb. 9, 1998.

Wong and Clohs, "Protein Binding Study of AA5, a New Antiarrhythmic Drug", Nortran Pharmaceuticals Inc., Vancouver, BC, Poster Conference, Aug. 2000.

Wong and Clohs, "Capillary Electrophoresis Assay to Assess In Vitro Metabolic Stability of Novel Compounds in Human Liver Microsomes", Cardiome Pharma Corp., Vancouver, BC, AAPS Poster, Oct. 2001.

Yeola et al., "Molecular Analysis of a Binding Site for Quinidine in a Human Cardiac Delayed Rectifier $K^+$ Channel—Role of S6 in Antiarrhythmic Drug Binding", *Circ Res* 78(6): 1105-1114, Jun. 1996.

Yong et al., "Low pKa Predicts Antiarrhythmic Efficacy in a Series of Aminocyclohexyl Esters", *J Mol Cell Cardiol*, Abstract 057, 1997.

Yong et al., "RSD1000: A Novel Antiarrhythmic Agent with Increased Potency Under Acidic and High-Potassium Conditions", *J Pharm Exp Ther* 289(1):236-244, 1999.

Yong et al., "RSD1000: A Novel Antiarrhythmic Agent with an Improved Therapeutic Index", *BPS Proceedings* 119P, 1996.

Yong et al., "SAR Evidence that Antiarrhythmic Activity is Unrelated to Opioid Kappa Agonist Activity", *BPS Proceedings* 117P, 1996.

Zhang et al., "Inhibition of [$^3$H]-U69593 binding and the cardiac effects of U50, 488H by calcium channel blockers in the rat heart", *Brit J Pharmacol* 120:827-832, 1997.

Zolotoy et al., "Physicochemical Determinants for Drug Induced Blockade of HERG Potassium Channels: Effect of Charge and Charge Shielding", *Curr Med Chem* 1(3): 1-17, 2003.

\* cited by examiner

PRODRUGS OF ION CHANNEL MODULATING COMPOUNDS AND USES THEREOF

FIELD OF THE INVENTION

The field of the compounds and methods described herein is generally prodrugs of ion channel modulating compounds and their uses, and includes but is not limited to prodrugs of ion channel modulating compounds and their uses as antiarrhythmics, particularly for the treatment and/or prevention of atrial fibrillation (AF) and for the treatment and/or prevention of atrial flutter.

BACKGROUND OF THE INVENTION

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

For example, cardiac ion channels are proteins that reside in the cell membrane and control the electrical activity of cardiac tissue. In response to external stimuli, such as changes in potential across the cell membrane, these ion channels can form a pore through the cell membrane, and allow movement of specific ions into or out of the cell. The integrated behavior of thousands of ion channels in a single cell results in an ionic current, and the integrated behavior of many of these ionic currents makes up the characteristic cardiac action potential.

Arrhythmia is a variation from the normal rhythm of the heart beat and generally represents the end product of abnormal ion-channel structure, number or function. Both atrial arrhythmias and ventricular arrhythmias are known. The major cause of fatalities resulting from cardiac arrhythmias is the subtype of ventricular arrhythmias known as ventricular fibrillation (VF). Conservative estimates indicate that, in the U.S. alone, each year over one million Americans will have a new or recurrent coronary attack (defined as myocardial infarction or fatal coronary heart disease). About 650,000 of these individuals will be first heart attacks and 450,000 of these individuals will be recurrent attacks. About one-third of individuals experiencing these attacks will die as a result. At least 250,000 people a year die of coronary heart disease within 1 hour of the onset of symptoms and before they reach adequate medical aid. These are sudden deaths caused by cardiac arrest, usually resulting from ventricular fibrillation.

Atrial fibrillation (AF) is the most common arrhythmia seen in clinical practice and is a cause of morbidity in many individuals (Pritchett E. L., *N. Engl. J. Med.* 327(14): 1031 Oct. 1, 1992, discussion 1031-2; Kannel and Wolf, *Am. Heart J.* 123(1): 264-7 Jan. 1992). The prevalence of AF is likely to increase as the population ages and it is estimated that 3-5% of patients over the age of 60 years have AF (Kannel W. B., Abbot R. D., Savage D. D., McNamara P. M., *N. Engl. J. Med.* 306(17): 1018-22, 1982; Wolf P. A., Abbot R. D., Kannel W. B., *Stroke* 22(8): 983-8, 1991). While AF is rarely fatal, it can impair cardiac function and is a major cause of stroke (Hinton R. C., Kistler J. P., Fallon J. T., Friedlich A. L., Fisher C. M., *Am. J. Cardiol.* 40(4): 509-13, 1977; Wolf P. A., Abbot R. D., Kannel W. B., *Arch. Intern. Med.* 147(9): 1561-4, 1987; Wolf P. A., Abbot R. D., Kannel W. B., *Stroke* 22(8): 983-8, 1991; Cabin H. S., Clubb K. S., Hall C., Perlmutter R. A., Feinstein A. R., *Am. J. Cardiol.* 65(16): 1112-6, 1990).

Antiarrhythmic agents have been developed to prevent or alleviate cardiac arrhythmia. For example, Class I antiarrhythmic compounds have been used to treat supraventricular arrhythmias and ventricular arrhythmias. Treatment of ventricular arrhythmia is very important since such an arrhythmia can be fatal. Serious ventricular arrhythmias (ventricular tachycardia and ventricular fibrillation) occur most often in the presence of myocardial ischemia and/or infarction. Ventricular fibrillation often occurs in the setting of acute myocardial ischemia, before infarction fully develops. At present, there is no satisfactory pharmacotherapy for the treatment and/or prevention of ventricular fibrillation during acute ischemia. In fact, many Class I antiarrhythmic compounds may actually increase mortality in patients who have had a myocardial infarction.

Class Ia, Ic and III antiarrhythmic drugs have been used to convert recent onset AF to sinus rhythm and prevent recurrence of the arrhythmia (Fuch and Podrid, 1992; Nattel S., Hadjis T., Talajic M., *Drugs* 48(3): 345-71, 1994). However, drug therapy is often limited by adverse effects, including the possibility of increased mortality, and inadequate efficacy (Feld G. K., *Circulation* 83(6): 2248-50, 1990; Coplen S. E., Antman E. M., Berlin J. A., Hewitt P., Chalmers T. C., *Circulation* 1991; 83(2): 714 and *Circulation* 82(4): 1106-16, 1990; Flaker G. C., Blackshear J. L., McBride R., Kronmal R. A., Halperin J. L., Hart R. G., *J. Am. Coll. Cardiol* 20(3): 527-32, 1992; CAST, *N. Engl. J. Med.* 321: 406, 1989; Nattel S., *Cardiovasc. Res.* 37(3): 567-77, 1998). Conversion rates for Class I antiarrhythmics range between 50-90% (Nattel S., Hadjis T., Talajic M., *Drugs* 48(3): 345-71, 1994; Steinbeck G., Remp T., Hoffmann E., *J. Cardiovasc. Electrophysiol.* 9 (8 Suppl):S104-8, 1998). Class III antiarrhythmics appear to be more effective for terminating atrial flutter than for AF and are generally regarded as less effective than Class I drugs for terminating of AF (Nattel S., Hadjis T., Talajic M., *Drugs* 48(3): 345-71, 1994; Capucci A., Aschieri D., Villani G. Q., *Drugs Aging* 13(1): 51-70, 1998). Examples of such drugs include ibutilide, dofetilide and sotalol. Conversion rates for these drugs range between 30-50% for recent onset AF (Capucci A., Aschieri D., Villani G. Q., *Drugs Aging* 13(1): 51-70, 1998), and they are also associated with a risk of the induction of Torsades de Pointes ventricular tachyarrhythmias. For ibutilide, the risk of ventricular proarrhythmia is estimated at ~4.4%, with ~1.7% of patients requiring cardioversion for refractory ventricular arrhythmias (Kowey P. R., VanderLugt J. T., Luderer J. R., *Am. J. Cardiol.* 78 (8A): 46-52, 1996). Such events are particularly tragic in the case of AF as this arrhythmia is rarely a fatal in and of itself.

There remains a need in the art to identify new antiarrhythmic treatments, for both ventricular arrhythmias as well as for atrial arrhythmias. The present invention fulfills this need, and further provides other related advantages.

Related Literature

Certain ion channel modulating agents are disclosed in PCT Published Patent Application No. WO 1999/50225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. WO 2005002693.

SUMMARY OF THE INVENTION

In one aspect, this invention is directed to prodrugs of ion channel modulating compounds, wherein the prodrug comprises an ion channel modulating compound attached to one or more prodrug moieties.

In another aspect, this invention is directed to pharmaceutical compositions comprising prodrugs of ion channel modulating compounds and pharmaceutically acceptable excipients.

In another aspect, this invention is directed to methods of treating arrhythmia in a subject in need thereof, wherein the method comprises administering to the subject a therapeutically effective amount of a prodrug of an ion channel modulating compound or a pharmaceutical composition comprising an ion channel modulating compound and a pharmaceutically acceptable excipient.

In another aspect, this invention is directed to method for modulating ion channel activity in a subject in need thereof, wherein the method comprises administering to the subject a therapeutically effective amount of a prodrug of an ion channel modulating compound or a pharmaceutical composition comprising an ion channel modulating compound and a pharmaceutically acceptable excipient.

These aspects are described in more detail below.

DETAILED DESCRIPTION OF THE INVENTION

As disclosed within the present invention, a variety of cardiac pathological conditions may be treated and/or prevented by the use of one or more of the compounds disclosed herein that, either singly or together with one or more additional therapeutic agents, are able to selectively inhibit certain combinations of cardiac ionic currents. More specifically, the cardiac currents referred to above are the sodium currents and early repolarising currents.

Early repolarising currents correspond to those cardiac ionic currents which activate rapidly after depolarization of membrane voltage and which effect repolarisation of the cell. Many of these currents are potassium currents and may include, but are not limited to, the transient outward current $I_{to1}$ such as Kv4.2 and Kv4.3), and the ultrarapid delayed rectifier current ($I_{Kur}$) such as Kv1.5, Kv1.4 and Kv2.1). The ultrarapid delayed rectifier current ($I_{Kur}$) has also been described as $I_{sus}$. A second calcium dependent transient outward current ($I_{to2}$) has also been described.

The cardiac pathological conditions that may be treated and/or prevented by the compounds of the present invention may include, but are not limited to, arrhythmias such as the various types of atrial and ventricular arrhythmias.

Of particular interest to the present invention are the ion channel modulating compounds disclosed in PCT Published Patent Application No. WO 1999/50225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. WO 2005002693; the disclosures of which are incorporated in full herein by reference in their entireties.

A. Definitions

In accordance with the present invention and as used herein, the following terms are defined to have the following meanings, unless explicitly stated otherwise:

"Acyl" refers to branched or unbranched hydrocarbon fragments terminated by a carbonyl —(C=O)— group containing the specified number of carbon atoms. Examples include acetyl [$CH_3(C=O)$—, a $C_2$acyl] and propionyl [$CH_3CH_2(C=O)$—, a $C_3$acyl].

"Alkanoyloxy" refers to an ester substituent wherein the ether oxygen is the point of attachment to the molecule. Examples include propanoyloxy [($CH_3CH_2(C=O)$—O—, a $C_3$alkanoyloxy] and ethanoyloxy [$CH_3(C=O)$—O—, a $C_2$alkanoyloxy].

"Alkoxy" refers to an O-atom substituted by an alkyl group, for example, methoxy [—$OCH_3$, a $C_1$alkoxyl.

"Alkoxyalkyl" refers to an alkylene group substituted with an alkoxy group. For example, methoxyethyl [$CH_3OCH_2CH_2$—] and ethoxymethyl($CH_3CH_2OCH_2$—] are both $C_3$alkoxyalkyl groups.

"Alkoxycarbonyl" refers to an ester substituent wherein the carbonyl carbon is the point of attachment to the molecule. Examples include ethoxycarbonyl [$CH_3CH_2O(C=O)$—, a $C_3$alkoxycarbonyl] and methoxycarbonyl [$CH_3O(C=O)$—, a $C_2$alkoxycarbonyl].

"Alkyl" refers to a branched or unbranched hydrocarbon fragment containing the specified number of carbon atoms and having one point of attachment. Examples include n-propyl (a $C_3$alkyl), iso-propyl (also a $C_3$alkyl), and t-butyl (a $C_4$alkyl).

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group [—COOH]. Examples include carboxymethyl [HOOC—$CH_2$—, a $C_2$alkylcarboxy] and carboxyethyl [HOOC—$CH_2CH_2$—, a $C_3$alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds, where phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2$—, a $C_7$aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Heteroatom" refers to a non-carbon atom, where boron, nitrogen, oxygen, sulfur and phosphorus are preferred heteroatoms, with nitrogen, oxygen and sulfur being particularly preferred heteroatoms.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing a hydroxy (—OH) group. Examples include hydroxymethyl (—CH$_2$OH, a C$_1$hydroxyalkyl) and 1-hydroxyethyl (—CHOHCH$_3$, a C$_2$hydroxyalkyl).

"Thioalkyl" refers to a sulfur atom substituted by an alkyl group, for example thiomethyl(CH$_3$S—, a C$_1$thioalkyl).

"Modulating" in connection with the activity of an ion channel means that the activity of the ion channel may be either increased or decreased in response to administration of a compound or composition or method described herein. Thus, the ion channel may be activated, so as to transport more ions, or may be blocked, so that fewer or no ions are transported by the channel.

As used herein, a "subject" may generally be any human or non-human animal that would benefit from the methods described in this application. In one version of the methods, a subject is a human subject. In some versions of the methods, a subject is a warm-blooded animal. In some versions of the methods, a subject is a mammal. In some versions, the subject is any domestic animal, including, but not limited to dogs and cats. In some versions, the subject is any livestock animal, including but not limited to horses, pigs and cattle. In some versions, the subject is any zoo animal, including but not limited to Bengal tigers.

As used herein, unless the context makes clear otherwise, "treatment," and similar word such as "treated," "treating" etc., is an approach for obtaining beneficial or desired results, including and preferably clinical results. Treatment can involve optionally either the amelioration of symptoms of the disease or condition, or the delaying of the progression of the disease or condition.

As used herein, unless the context makes clear otherwise, "prevention," and similar word such as "prevented," "preventing" etc., is an approach for preventing the onset of a disease or condition or preventing the occurrence of the symptoms of a disease or condition, or optionally an approach for delaying the onset of a disease or condition or delaying the occurrence of the symptoms of a disease or condition. As used herein, "prevention" and similar words also includes reducing the intensity, effect, symptoms and/or burden of a disease or condition prior to onset of the disease or condition.

As used herein, an "effective amount" or a "therapeutically effective amount" of a substance is that amount sufficient to affect a desired biological effect, such as beneficial results, including clinical results.

As used herein, unless the context makes clear otherwise, "inhibition" and similar words such as "inhibit" of any ion channel means any decrease in current through that channel. When "inhibition" is used in the context of a specified concentration, it is determined by the IC$_{50}$. For example, an ion channel modulating compound which inhibits an ion channel at a concentration of 1 µM, the ion channel may be said to have an IC$_{50}$ of 1 µM for that ion channel modulating compound. This example is for illustrative purposes only and is in no way intended to be limiting.

As used herein, unless the context makes clear otherwise, "IC$_{50}$" or "IC$_{50}$ concentration" means a drug concentration at which the specified current amplitude (peak or steady-state, or integrated current) is inhibited by 50%.

As used herein, unless the context makes clear otherwise, "blocking" or "block" of an ion channel means any block or inhibition of current through that ion channel.

As used herein, unless the context makes clear otherwise, "recovery time constant of inhibition" refers to a time constant at which recovery of current amplitude occurs, presumed to reflect dissociation of a drug from its binding site, as for example, a sodium channel when the stimulus rate is decreased from 10 Hz to 1 Hz.

"Pharmaceutically acceptable carriers" for therapeutic use are well known in the pharmaceutical art, and are described, for example, in *Remington's Pharmaceutical Sciences*, Mack Publishing Co. (current edition). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

"Pharmaceutically acceptable salt" refers to salts of a compound of the invention derived from the combination of such compounds and a pharmaceutically acceptable organic or inorganic acid (acid addition salts) or a pharmaceutically acceptable organic or inorganic base (base addition salts) which retain the biological effectiveness and properties of the compounds of the present invention and which are not biologically or otherwise undesirable. The compounds of the invention described herein may be used in either the free base or salt forms, with both forms being considered as being within the scope intended herein. Pharmaceutically-acceptable salts of the compounds of the invention include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochloride and sulfates; and salts of organic acids, such as but not limited to acetates, lactates, malates, tartrates, citrates, ascorbates, succinates, butyrates, valerates and fumarates. Other examples of pharmaceutically acceptable salt include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

When the compounds described herein contain olefinic double bonds or other centers of geometric asymmetry, and unless specified otherwise, it is intended that the compounds include both E and Z geometric isomers. Likewise, all tautomeric forms are also Intended to be included.

It is also to be understood that the compounds described herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

For purposes of this invention, when a bond is indicated in a formula as a wavy line, such as the bond between the oxygen atom and cyclopentyl moiety in compound of formula (IA), it is meant to indicate a bond which can give rise to either R or S stereochemistry.

Following the standard chemical literature description practice and as used herein, a full wedge bond means above the ring plane, and a dashed wedge bond means below the ring plane; one full bond and one dashed bond (i.e., — — — —) means a trans configuration, whereas two full bonds or two dashed bonds means a cis configuration.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position.

Optically active (+) and (−), (R)- and (S)-, or (D)- and (L)-isomers may be prepared using chiral synthons or chiral reagents, or resolved using conventional techniques, such as reverse phase HPLC.

Thus, in the description of the compounds of formulae (I), (IA) and (IX) and Compound A, as described herein, all enantiomeric and diastereomeric forms of the compounds are intended. Pure stereoisomers, mixtures of enantiomers and/or diastereomers, and mixtures of different ion channel modulating compounds are described. The compounds of formulae (I), (IA) and (IX) may therefore occur as racemates, racemic mixtures and as individual diastereomers or enantiomers with all isomeric forms being included in the present invention. A racemate or racemic mixture does not imply a 50:50 mixture of stereoisomers. Where a given structural formula or chemical name is presented for a compound of formulae (I), (IA) and (IX) it is intended that all possible solvates, pharmaceutically acceptable salts, esters, amides, complexes, chelates, stereoisomers, geometric isomers, crystalline or amorphous forms, metabolites, or metabolic precursors of the compound are also separately described by the chemical structural formula or chemical name.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

The prodrugs of the invention may contain an "aminocycloalkyl ether moiety", i.e., the following moiety:

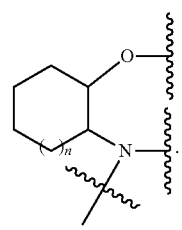

where n is 0, 1, 2, or 3. As used herein, the term "aminocycloalkyl ether moiety" includes compounds wherein the cycloalkyl group is a cyclohexyl group, such as in compounds of formula (I), formula (IA) and Compound A disclosed herein, and includes compounds wherein the cycloalkyl group is a cyclopentyl, cycloheptyl or cyclooctyl group, such as in compounds of formula (IX) disclosed herein.

As used herein, "equivalently inhibits" and "equivalently inhibited" means equally inhibits or equally inhibited. In one version, equivalently inhibits means that there is no statistically significant difference in inhibition of currents resulting from application of an ion channel modulating compound. For example, the early and sustained sodium currents are equivalently inhibited if there is no statistically significant difference in the effect of an ion channel modulating compound on early and sustained sodium currents.

As used herein, "rapidly associated and dissociated" means that a compound has blocking and unblocking kinetics of the "fast-on, fast-off" form such as the "fast-on, fast-off" kinetics defined by Carmeliet and Mubagwa (Prog. Biophys. Molec. Biol. 70, 1-72, 1998). For example, an ion channel modulating compound rapidly associates and dissociates from sodium channels where the ion channel modulating compound has "fast-on, fast-off" kinetics as defined by Carmeliet and Mubagwa.

As used herein, "rate-independent and use-independent" inhibition means inhibition that is predominantly heart rate and/or stimulus rate and use-independent such that there is no statistically significant effect of steady-state or transient changes in heart rate or stimulus rate with respect to the inhibition. For example, an ion channel modulating compound that inhibits Kv1 channels in a "rate-independent and use-independent" manner means that there is no influence of the heart rate or stimulus rate on the amount of inhibition produced by the ion channel modulating compound on Kv1 channels.

As used herein, "affects atrial repolarizing currents" means "has a statistically significant effect on atrial repolarizing current amplitudes."

As used herein, "prolongs atrial refractoriness" means "has a statistically significant prolonging effect on atrial refractoriness."

As used herein, "has substantially no effect on ventricular tissue" means "has no statistically significant effect on normal human ventricular action potential duration or refractoriness." Any apparent difference in effect, therefore, is attributed to intrinsic variability, such as in one aspect, less than a 10% difference.

As used herein, "does not substantially slow conduction" means "has no statistically significant effect on slowing conduction in the ventricles." As such, any apparent difference in effect, therefore, is attributed to intrinsic variability. In one aspect, the ion channel modulating compound has no statistically significant effect on the slowing of conduction wherein the compound produces less than a 15%, preferably less than a 10%, increase in cardiac QRS duration at physiological heart rates.

As used herein, "rate-dependent inhibition" of an ion channel means that the level of inhibition of the ion channel changes with the frequency of stimulation.

The term "QT interval" is used as is known in the art; for example, the QT interval as measured from an electrocardiogram. As used herein, unless the context makes clear otherwise, the term "prolongs" or "prolong" generally means extends or lengthens as in duration.

The term "antiarrhythmic" is used as is known in the art; for example, as a compound which prevents or alleviates irregularities in heart rate.

The term "induces" as used herein, unless the context indicates otherwise, generally means to stimulate the occurrence of.

The term "chemically induced" or "chemically induces" is used as is known in the art. As used herein, unless the context makes clear otherwise, the term "terminating" or "terminates" generally means to bring to an end or to halt.

B. Compounds of Formula (I), (IA), (IX) and Compound A

In one aspect, the prodrugs of the invention comprise an ion channel modulating compound and a prodrug moiety. Generally, any compound that modulates ion channel activity may by an ion channel modulating compound. A compound that modulates, ion channel activity may be a compound that increases or decreases ion channel activity. An ion channel modulating compound that decreases ion channel activity may be a compound that blocks ion channel activity completely or partially.

In another version, any compound that either singly or together with one or more additional compounds selectively inhibit certain combination of cardiac ionic currents is an ion channel modulating compound. The cardiac currents may be the sodium currents and early repolarizing currents. Ion channel modulating compounds may block cardiac currents from extracellular loci. Such compounds act on an external locus of the ion channel that is accessible from the extracellular surface. This facilitates access to the ion channel and provides rapid onset kinetics and exhibits frequency dependent blockade of currents. Such properties are all beneficial for compounds used to treat arrhythmias. An ion channel modulating compound may selectively inhibit cardiac early repolarizing currents and cardiac sodium currents. Ion channel modulating compounds may be used to selectively inhibit cardiac early repolarizing currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation and those conditions that precede the onset of arrhythmias such as atrial fibrillation. An ion channel modulating compound may be an atrial selective agent. An ion channel modulating compound may treat or prevent ventricular arrhythmia. An ion channel modulating compound may block cardiac sodium currents or cardiac early repolarizing currents. An ion channel modulating compound may inhibit multiple cardiac ionic currents. An ion channel modulating compound may be used to treat or prevent arrhythmic, including ventricular or atrial arrhythmia, particularly atrial fibrillation.

The ion channel modulating compounds may block the cardiac ion channels responsible for early repolarizing currents and sodium currents; and/or block cardiac early repolarizing currents and cardiac sodium currents under conditions where an arrhythmogenic substrate is present in the heart; and/or block the cardiac ion channels responsible for early repolarizing currents and sodium currents under conditions where an arrhythmogenic substrate is present in the heart; and/or block cardiac early repolarizing currents and cardiac sodium currents from extracellular loci in cardiac cells.

In one variation, the cardiac early repolarizing currents referred to above comprise ionic currents which activate rapidly after depolarization of membrane voltage and which effect repolarization of the cell. The early repolarizing currents may comprise the cardiac transient outward potassium current ($I_{to}$) and/or the ultrarapid delay rectifier current ($I_{Kur}$). The cardiac transient outward potassium current ($I_{to}$) and/or the ultrarapid delay rectifier current ($I_{Kur}$) may comprise at least one of the Kv4.2, Kv4.3, Kv2.1, Kv1.4 and Kv1.5 currents.

Ion channel modulating compounds may generally have any pKa, however ion channel modulating compounds typically have pKa values of between 4-9, and may have pKa values that are less than 8, including pKa values between 5-7.5. Methods to determine pKa values are well known in the art (see, e.g., Perrin, "Dissociation Constants of Organic Bases in Aqueous Solution", Butterworth, London, 1972). For ion channel modulating compounds with the specific ranges of pKa described above, the fraction of the charged (protonated) species will be increased under the pathological conditions such as cardiac arrhythmias and the presence of an arrhythmogenic substrate in the heart as described above due to the increase in cardiac milieu acidity. Where the charged form of a compound is active, its potency increases under conditions associated with an increase in cardiac milieu acidity.

Particular ion channel modulating compounds have structural characteristics that may be determined by various physical methods, such as single crystal X-ray crystallography. For instance, some ion channel modulating compounds comprise a cycloalkane ring and substituents J and K as shown below in structure T, wherein the relative positions of J and K provide a "C" shaped angle and wherein n=1, 2, 3 or 4.

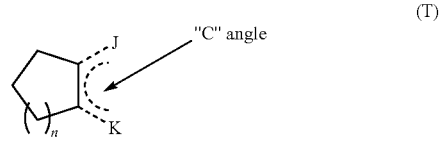

(T)

Typically, one of J and K comprises a hydrophobic moiety, such as but not limited to a moiety comprising alkyl and/or aryl moieties. In one variation, one of J and K comprises a hydrophobic aromatic moiety, which may be attached to the cycloalkane ring of structure T via an ether bond. Typically, one of J and K comprises a hydrophilic moiety, such as a heteroatom containing moiety, including but not limited to a nitrogen containing moiety that is available to form a quaternary salt and/or a hydroxyl moiety. In one variation, one of J and K comprises a nitrogen containing moiety substituted with a hydroxyl moiety or the like, such as a pyrrolidinyl moiety. In a particular variation of structure T, n=2, J comprises an aromatic moiety and K comprises a nitrogen containing moiety substituted with a hydroxyl moiety or the like. The cycloalkane ring may be optionally substituted. In one version, the cycloalkane ring may be replaced by a structural moiety imparting rigidity to the relative positions of the J and K groups. For example if the J and K groups are attached to atoms L and M that are directly bonded to each other, any group that does not allow substantial rotation about the bond between atoms L and M can impart rigidity to the relative positions of the J and K groups. For example, the ion channel modulating compound may be a compound of formula

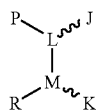

where J and K are as described above and groups P and R are moieties such that there is not substantial rotation about the L-M bond. In one example P and R are taken together form a cyclic moiety that prevents substantial rotation about the L-M bond.

In one version, the ion channel modulating compound comprises an amino substituted 5, 6, 7 or 8-membered ring, which may be a 5, 6, 7, or 8-membered substituted or unsubstituted cycloalkyl ring. The amino substituted cycloalkane ring may be an aminocyclohexyl ring and may be further substituted with one or more additional moieties. In one version, the amino substituted cycloalkane ring is further substituted with an ether moiety. In some instances, the ion channel modulating compound comprises an aminocyclohexyl ring that is further substituted with an ether moiety.

In another, the ion channel modulating compound is a protonated version of any of the ion channel modulating compounds described herein. That is, for each ion channel modulating compound described herein, the quaternary protonated amine form of the compound may also be considered as an amino ion channel modulating compound. These quaternary protonated amine forms of the compounds may be present in the solid phase, for example in crystalline or amorphous form, and may be present in solution. These quaternary protonated amine forms of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

One preferred embodiment of the invention are those prodrugs wherein the ion channel modulating compound is a compound of formula (I), or solvates or pharmaceutically acceptable salts thereof:

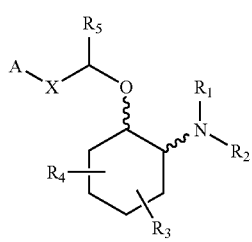

(I)

wherein, independently at each occurrence,

X is selected from a direct bond, —C($R_6$,$R_{14}$)—Y— and —C($R_{13}$)=CH—, with the proviso that when X is a direct bond and A is formula (III), then at least one of $R_7$, $R_8$ and $R_9$ is not hydrogen;

Y is selected from a direct bond, O, S and $C_1$-$C_4$alkylene;

$R_{13}$ is selected from hydrogen, $C_1$-$C_6$alkyl, $C_3$-$C_8$cycloalkyl, aryl and benzyl;

$R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached in formula (I), form a ring denoted by formula (II):

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached in formula (I), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cyclohexane ring shown in formula (I) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from $C_5$-$C_{12}$alkyl, a $C_3$-$C_{13}$-carbocyclic ring, and ring systems selected from formulae (III), (IV), (V), (VI), (VII) and (VIII):

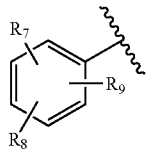
(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and $N(R_{15},R_{16})$ where $R_{15}$ and $R_{16}$ are independently selected from hydrogen, acetyl, methanesulfonyl and $C_1$-$C_6$alkyl;

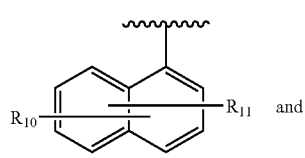
(IV) and

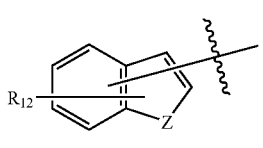
(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl;

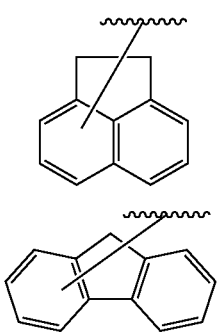
(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

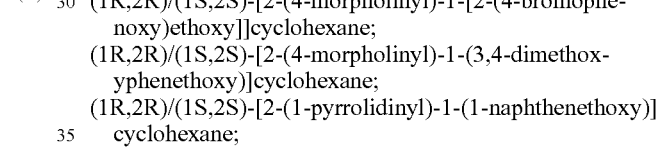
(VII)

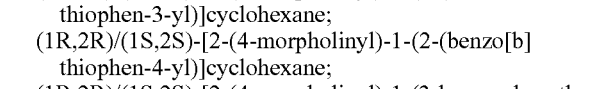
(VIII)

as isolated enantiomeric, diastereomeric and geometric isomers thereof, and mixtures thereof.

Of particular interest are prodrugs wherein the ion channel modulating compound of formula (I) is selected from the group consisting of the following:

(1R,2R)/(1S,2S)-[2-(4-morpholinyl)-1-(2-naphthenethoxy)]cyclohexane;
(1R,2R)/(1S,2S)-[2-(4-morpholinyl)-1-(1-naphthenethoxy)]cyclohexane;
(1R,2R)/(1S,2S)-[2-(4-morpholinyl)-1-(4-bromophenethoxy)]cyclohexane;
(1R,2R)/(1S,2S)-[2-(4-morpholinyl)-1-[2-(2-naphthoxy)ethoxy]]cyclohexane;
(1R,2R)/(1S,2S)-[2-(4-morpholinyl)-1-[2-(4-bromophenoxy)ethoxy]]cyclohexane;
(1R,2R)/(1S,2S)-[2-(4-morpholinyl)-1-(3,4-dimethoxyphenethoxy)]cyclohexane;
(1R,2R)/(1S,2S)-[2-(1-pyrrolidinyl)-1-(1-naphthenethoxy)]cyclohexane;
(1R,2R)/(1S,2S)-[2-(4-morpholinyl)-1-(2-(benzo[b]thiophen-3-yl)]cyclohexane;
(1R,2R)/(1S,2S)-[2-(4-morpholinyl)-1-(2-(benzo[b]thiophen-4-yl)]cyclohexane;
(1R,2R)/(1S,2S)-[2-(4-morpholinyl)-1-(3-bromophenethoxy)]cyclohexane;
(1R,2R)/(1S,2S)-[2-(4-morpholinyl)-1-(2-bromophenethoxy)]cyclohexane;
(1R,2R)/(1S,2S)-[2-(4-morpholinyl)-1-(3-(3,4-dimethoxyphenyl)propoxy)]cyclohexane;
(1R,2R)/(1S,2S)-[2-[bis(2-methoxyethyl)aminyl]-1-(2-naphthenethoxy)]cyclohexane;
(1R,2R)/(1S,2S)-2-(4-morpholinyl)-1-(3,4-dichlorophenethoxy)cyclohexane;
(1R,2R)/(1S,2S)-2-(3-ketopyrrolidinyl)-1-(1-naphthenethoxy)cyclohexane;
(1R,2R)/(1S,2S)-2-(1-acetylpiperazinyl)-1-(2-naphthenethoxy)cyclohexane;
(1R,2R)/(1S,2S)-2-(3-ketopyrrolidinyl)-1-(2,6-dichlorophenethoxy)cyclohexane;
(1R,2R)/(1S,2S)-2-[1,4-dioxa-7-azaspiro[4.4]non-7-yl]-1-(1-naphthenethoxy)cyclohexane;
(1R,2S)/(1S,2R)-2-(4-morpholinyl)-1-[(2-trifluoromethyl)phenethoxy]cyclohexane monohydrochloride;
(1R,2R)/(1S,2S)-2-(3-ketopyrrolidinyl)-1-[3-(cyclohexyl)propoxy]cyclohexane monohydrochloride;
(1R,2R)/(1S,2S)-2-(3-acetoxypyrrolidinyl)-1-(1-naphthenethoxy)cyclohexane monohydrochloride;
(1R,2R)/(1S,2S)-2-(4-morpholinyl)-1-[(2,6-dichlorophenyl)methoxy]cyclohexane monohydrochloride;
(1R,2R)/(1S,2S)-2-(3-ketopyrrolidinyl)-1-[(2,6-dichlorophenyl)methoxy]cyclohexane monohydrochloride;

(1R,2R)/(1S,2S)-2-(3-hydroxypyrrolidinyl)-1-(2,6-dichlorophenethoxy)cyclohexane monohydrochloride;
(1R,2R)/(1S,2S)-2-(3-ketopyrrolidinyl)-1-(2,2-diphenylethoxy)cyclohexane monohydrochloride;
(1R,2R)/(1S,2S)-2-(3-thiazolidinyl)-1-(2,6-dichlorophenethoxy)cyclohexane monohydrochloride;
(1R,2S)/(1S,2R)-2-(3-ketopyrrolidinyl)-1-(1-naphthenethoxy)cyclohexane monohydrochloride; and
(1R,2R)/(1S,2S)-2-(3-hydroxypyrrolidinyl)-1-(3,4-dimethoxyphenethoxy)cyclohexane monohydrochloride.

Another preferred embodiment of the prodrugs of the invention are those prodrugs wherein the ion channel modulating compound is a compound of formula (IA), or solvates, pharmaceutically acceptable salts, esters, amides, complexes, chelates, stereoisomers, stereoisomeric mixtures, geometric isomers, crystalline or amorphous forms, metabolites, or metabolic precursors thereof:

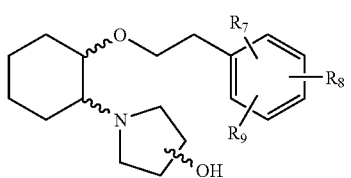

(IA)

wherein, $R_7$, $R_8$ and $R_9$ are independently selected from hydrogen, hydroxy and $C_1$-$C_6$alkoxy, as isolated enantiomeric, diastereomeric and geometric isomers thereof, and mixtures thereof, with the proviso that $R_7$, $R_8$ and $R_9$ cannot all be hydrogen.

Of particular interest are those prodrugs wherein the ion channel modulating compound of formula (IA) is selected from the group consisting of the following:
(1R,2R)/(1S,2S)-2-[(3R)/(3S)-Hydroxypyrrolidinyl]-1-(3,4-dimethoxyphenethoxy)-cyclohexane;
(1R,2R)/(1S,2S)-2-[(3R)-hydroxypyrrolidinyl]-1-(3,4-dimethoxyphenethoxy)-cyclohexane;
(1R,2R)/(1S,2S)-2-[(3S)-hydroxypyrrolidinyl]-1-(3,4-dimethoxyphenethoxy)-cyclohexane;
(1R,2R)-2-[(3R)-hydroxypyrrolidinyl]1-(3,4-dimethoxyphenethoxy)-cyclohexane;
(1R,2R)-2-[(3S)-hydroxypyrrolidinyl]-1-(3,4-dimethoxyphenethoxy)-cyclohexane;
(1R,2S)-2-[(3R)-hydroxypyrrolidinyl]-1-(3,4-dimethoxyphenethoxy)-cyclohexane;
(1R,2S)-2-[(3S)-hydroxypyrrolidinyl]-1-(3,4-dimethoxyphenethoxy)-cyclohexane;
(1S,2R)-2-[(3R)-hydroxypyrrolidinyl]-1-(3,4-dimethoxyphenethoxy)-cyclohexane;
(1S,2R)-2-[(3S)-hydroxypyrrolidinyl]-1-(3,4-dimethoxyphenethoxy)-cyclohexane;
(1S,2S)-2-[(3R)-hydroxypyrrolidinyl]-1-(3,4-dimethoxyphenethoxy)-cyclohexane;
(1S,2S)-2-[(3S)-hydroxypyrrolidinyl]-1-(3,4-dimethoxyphenethoxy)-cyclohexane; and
(1R,2S)/(1S,2R)-2-[(3R)/(3S)-hydroxypyrrolidinyl]-1-(3,4-dimethoxyphenethoxy)-cyclohexane.

Another preferred embodiment of the prodrugs of the invention are those prodrugs wherein the ion channel modulating compound is a compound of formula (IX), or solvates or pharmaceutically acceptable salts thereof:

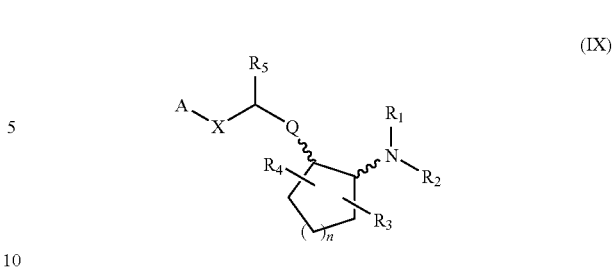

(IX)

wherein, independently at each occurrence,
n is selected from 1, 3 and 4;
Q is either 0 (oxygen) or —O—C(O);
X is selected from a direct bond, —C($R_6$,$R_{14}$)—Y—, and —C($R_{13}$)=CH—;
Y is selected from a direct bond, O, S, and $C_1$-$C_4$alkylene;
$R_{13}$ is selected from hydrogen, $C_1$-$C_6$alkyl, $C_3$-$C_8$cycloalkyl, aryl, and benzyl;
$R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or
$R_1$ and $R_2$, when taken together with the nitrogen atom to which they are directly attached in formula (IX), form a ring denoted by formula (II):

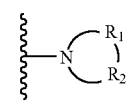

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or
$R_1$ and $R_2$, when taken together with the nitrogen atom to which they are directly attached in formula (IX), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;
$R_3$ and $R_4$ are independently attached to the cyclohexane ring shown in formula (IX) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;
$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from $C_5$-$C_{12}$alkyl, a $C_3$-$C_{13}$carbocyclic ring, and ring systems selected from formulae (III), (IV), (V), (VI), (VII) and (VIII):

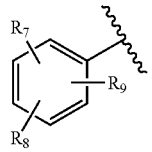

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and $N(R_{15},R_6)$ where $R_{15}$ and $R_{16}$ are independently selected from hydrogen, acetyl, methanesulfonyl and $C_1$-$C_6$alkyl;

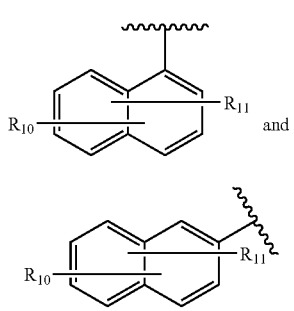

(IV)

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl;

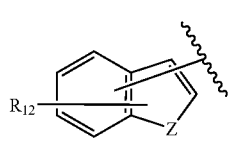

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_8$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (IX) when Z is CH or N, or Z may be directly bonded to $R_{17}$ when Z is N, and $R_{17}$ is selected from hydrogen, $C_1$-$C_6$alkyl, $C_3$-$C_3$cycloalkyl, aryl and benzyl;

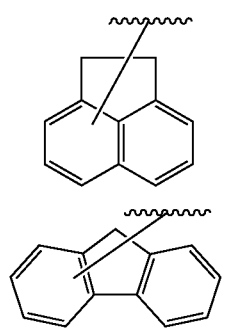

(VII)

(VIII)

as isolated enantiomeric, diastereomeric and geometric isomers thereof, and mixtures thereof.

Of particular interest are those prodrugs wherein the ion channel modulating compound of formula (IX) is selected from the group consisting of the following:

(1R,2R)/(1S,2S)-2-(4-morpholinyl)-1-(2-naphthalenethoxy) cyclopentane monohydrochloride; and (1R,2R)/(1S,2S)-2-(3-ketopyrrolidinyl)-1-(2,6-dichlorophenethoxy)cyclopentane monohydrochloride.

Another preferred embodiment of the prodrugs of the invention are those prodrugs wherein the ion channel modulating compound is Compound A:

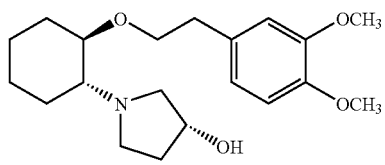

or pharmaceutically acceptable salts or solvates thereof.

This compound has the chemical name of (1R,2R)-2-[(3R)-hydroxypyrrolidinyl]-1-(3,4-dimethoxyphenethoxy) cyclohexane and is referred to herein as "Compound A". For purposes of this invention, the term "Compound A" is intended to include this compound and its pharmaceutically acceptable salts, solvates, esters, amides, complexes, chelates, stereoisomers, stereoisomeric mixtures, geometric isomers, crystalline or amorphous forms, metabolites, or metabolic precursors thereof.

C. Prodrugs of Ion Channel Modulating Compounds

Prodrugs of ion channel modulating compounds are described herein. In the sections below, the term "prodrug" refers to a prodrug of an ion channel modulating compound as described herein. The term "prodrug(s) of the invention" and "compound(s) of the invention" are interchangeable herein. Methods for the preparation of prodrugs and therapeutic uses thereof are also described.

A prodrug is a modified variation of a parent drug and is generally biologically inactive at its site of action, but may be degraded, modified, rearranged, disassociated or cleaved by one or more enzymatic, non-enzymatic or other in vivo or ex vivo processes to its parent bioactive form or a derivative thereof, wherein the derivative generally maintains a bioactive component of the parent drug but may provide a different bioactive component. A prodrug generally has a different pharmacokinetic profile than its parent drug such that, for example, it is more easily absorbed across the mucosal epithelium, it has better salt formation or solubility and/or it has better systemic stability (e.g., an increased plasma half-life).

Examples of modifications of a parent drug to yield a prodrug include but are not limited to: (1) ester or amide derivatives which are susceptible to being cleaved by esterases or lipases; (2) peptide derivatives which may be recognized by specific or nonspecific proteases; or (3) derivatives that cause the prodrug to accumulate at a site of action through membrane selection; and combinations of the above techniques. Conventional procedures for the selection and preparation of prodrug derivatives are described in H. Bundgaard, Design of Prodrugs, (1985), the contents of which are incorporated herein by reference in its entirety.

Any derivative of an ion channel modulating compound that may be degraded, modified, rearranged, disassociated or cleaved by one or more enzymatic, non-enzymatic or other in vivo or ex vivo processes to its parent bioactive form or a variation thereof may be a prodrug of an ion channel modulating compound. A derivative of an ion channel modulating compound may be a covalently modified or non-covalently modified derivative of the compound. Typically, a derivative is a covalently modified version of an ion channel modulating compound. A variation of a parent bioactive form includes any variation of an ion channel modulating compound wherein less than an entire prodrug moiety but more than no prodrug moiety are still attached to the ion channel modulating compound after the prodrug moiety is degraded, modified, rearranged, dissociated or cleaved. In one variation, a parent ion channel modulating compound may comprise a carboxylic acid moiety, and when the carboxylic acid moiety is converted into an ester moiety, the ester derivative of the ion channel modulating compound may be a prodrug.

A prodrug of an ion channel modulating compound may be a prodrug of any ion channel modulating compound, including compounds of formula (I), (IA), (IX) and Compound A described herein. A prodrug of an ion channel modulating compound typically comprises a prodrug moiety attached to an ion channel modulating compound either via a direct bond or via a linker.

A prodrug moiety may be any organic, inorganic or organometallic moiety, including but not limited to the prodrug moieties described in the "Prodrug Moieties" section below.

A prodrug moiety may be attached to an ion channel modulating compound at any site on the ion channel modulating compound amenable to its attachment. Sites at which prodrug moieties may be attached to an ion channel modulating compound to yield a prodrug include but are not limited to those sites described in the "prodrug attachment site" section below. A prodrug moiety may be attached to an ion channel modulating compound either via a direct bond from the prodrug moiety to the ion channel modulating compound or via a bond to a linker that is in turn bound to the ion channel modulating compound. Linkers that may be used in a prodrug include but are not limited to the linkers described in the "prodrug linker" section below.

Typically, a prodrug is formed by the attachment of one prodrug moiety to an ion channel modulating compound, thereby producing a prodrug. In this way, a prodrug is provided wherein the prodrug comprises a 1:1 molar ratio of prodrug moiety to parent ion channel modulating compound. However, a prodrug may be formed by the attachment of more than one prodrug moiety to an ion channel modulating compound. For instance, a prodrug may have a 2:1 or greater than 2:1 molar ratio of prodrug moiety to parent ion channel modulating compound.

In another variation, a prodrug may be formed by the attachment of more than one ion channel modulating compound to a single prodrug moiety, thereby producing a prodrug of a ion channel modulating compound. In another variation, a prodrug is provided wherein the molar ratio of the ion channel modulating compound to the prodrug moiety is 2:1 or greater than 2:1, such as 3:1, 4:1 or greater.

Modification of an Ion Channel Modulating Compound to a Prodrug

Any ion channel modulating compound may be modified to form a prodrug of an ion channel modulating compound, including compounds of formulae (I), (IA) or (IX) and Compound A as described herein. The ion channel modulating compound to be modified to a prodrug may increase or decrease ion channel activity of the ion channel modulating compound. In some instances, the ion channel modulating compound may be used in the treatment of arrhythmia. In still other instances, the ion channel modulating compound may be used in the treatment of atrial fibrillation.

Prodrug Moiety Attachment Site

A prodrug moiety may be attached to an ion channel modulating compound at any site on the ion channel modulating compound that is amenable to such attachment.

In general, when an ion channel modulating compound is modified to form a prodrug, at least one valency of the ion channel modulating compound is substituted with a bond to a prodrug moiety or with a bond to a linker that is in turn bound to the prodrug moiety. When a valency is said to be substituted with a bond, it is meant that any atom, unpaired electron, lone pair of electrons, or empty electron orbital present in the ion channel modulating compound may be replaced with a bond to the prodrug moiety or to a linker. For instance, an ion channel modulating compound comprising a hydroxyl functional group may form a prodrug by the replacement of the hydrogen atom of an —OH moiety with a bond to a prodrug moiety. Accordingly, a prodrug with an —OH moiety is provided.

An ion channel modulating compound may be attached to a linker or to the prodrug moiety by any bond, including but not limited to covalent, ionic, hydrogen, dative, van der Waals, or other chemical bonding or any combination of chemical bonding. In a particular version, the ion channel modulating compound is attached to the prodrug or linker via a covalent bond.

A functional group on an ion channel modulating compound may be used to directly attach a prodrug moiety or linker, or may be converted into a subsequent functional group, which is then attached to the prodrug moiety or linker. Illustrative examples of a functional group on an ion channel modulating compound that may be used for association with a prodrug moiety or linker include but are not limited to a hydroxyl, an amino, an ether, an ester, a thio-ester, a thiol, an alkene, an alkyne, an alkyl, a carboxyl, a ketone, an aldehyde, a thio-aldehyde, a thio-ketone, a thio-carboxyl, an acyl-halide, a thio-acyl-halide, an alkanoyloxy, a thio-alkanoyloxy, an alkoxycarbonyl, a thio-alkoxycarbonyl, an aryl, an aralkyl, an amide, a thio-amide, and a disulfide group. In one variation, a hydroxyl functionality on an ion channel modulating compound is used as an attachment site for a prodrug moiety or linker, for example, to create an ether linkage bond or an ester or amide linkage bond. In another variation, an amino functionality on an ion channel modulating compound is used as an attachment site for a prodrug moiety or linker, for example to create a quaternary amino linkage bond which may be present as a quaternary amino salt. In another variation, an ether functionality on an ion channel modulating compound is used as an attachment site for a prodrug moiety or linker, for example to create an ether linkage bond.

Prodrug Moieties

Any organic, organometallic or inorganic group or atom may be a prodrug moiety. Typically, a prodrug moiety is selected such that the prodrug is inactive or less active than the parent ion channel modulating compound until the prodrug moiety is disassociated, cleaved, degraded, modified, rearranged or the like, and the active ion channel modulating compound or a variation thereof is released. A prodrug moiety may impart on the ion channel modulating compound any one or a combination of altered pharmacokinetics, altered drug transport, improved bio-availability through increased water solubility or increased chemical stability.

In one embodiment of the invention, a prodrug moiety is provided such that the prodrug is an ester derivative of an ion channel modulating compound. In another variation, a prodrug moiety is provided such that the prodrug is a carbamate derivative of an ion channel modulating compound. In still another embodiment, a prodrug moiety is provided such that the prodrug is an ether derivative of an ion channel modulating compound.

In one embodiment of the invention, a prodrug moiety is provided to enhance the water solubility of the ion channel modulating compound. A prodrug comprising a water solubility enhancing moiety typically contains more than one hydroxyl functional group, and preferably contains 2-6 hydroxyl functional groups. In one embodiment, a prodrug comprises a water solubility enhancing moiety such as a monosaccharide, including but not limited to D- or L-glucose, or a 6-carboxylic acid derivative of a monosaccharide such as D- or L-glucuronic acid, and D- or L-gluconic acid, and the like.

In one embodiment, a prodrug moiety is provided, wherein the prodrug moiety is selected from the group consisting of:

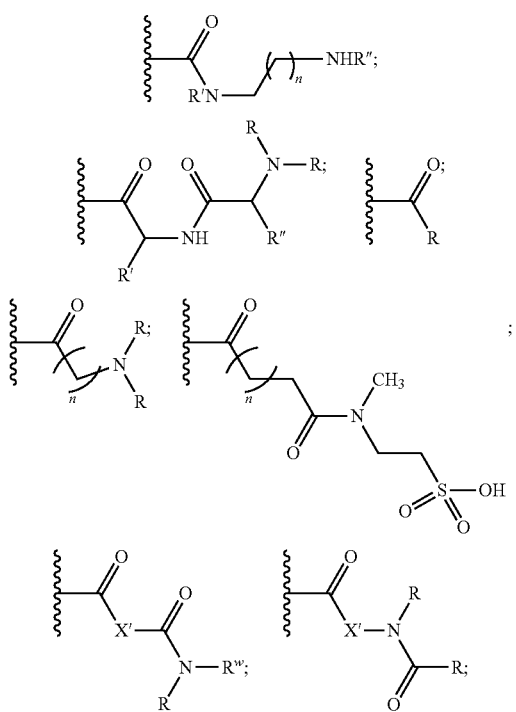

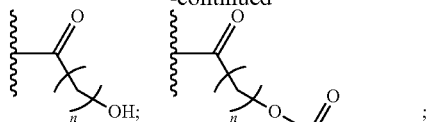

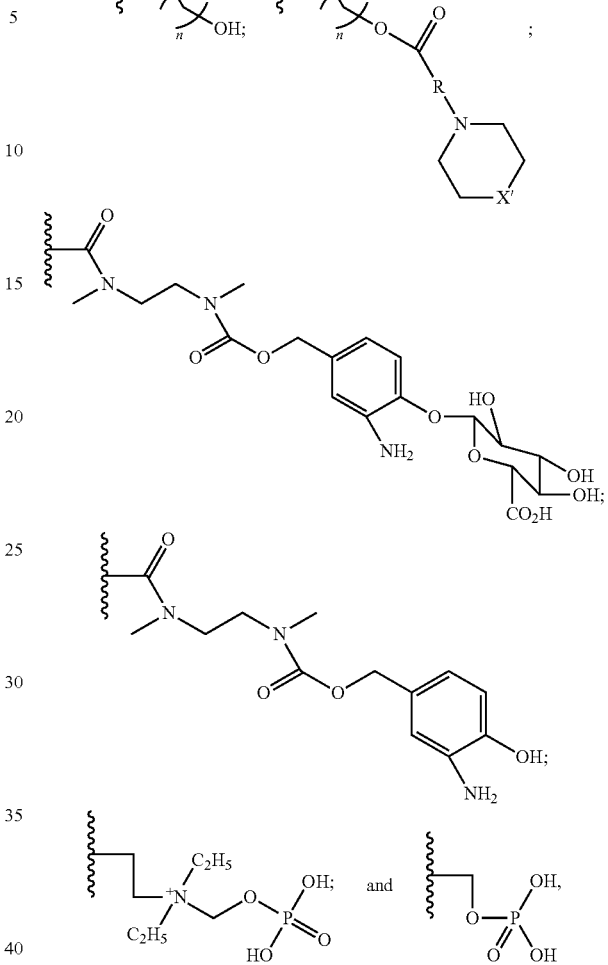

wherein:
R' and R" are independently selected from hydrogen and $C_1$-$C_6$ alkyl;
each R is independently selected from the group consisting of hydrogen, alkyl, substituted alkyl, alkenyl, substituted alkenyl, alkynyl and substituted alkynyl;
$R^w$ is a water-solubilizing moiety;
each X' is independently selected from O, NH, S or $CH_2$;
n is an integer from 1 to 10; and
wherein alkyl, substituted alkyl, alkenyl, substituted alkenyl, alkynyl and substituted alkynyl are as defined herein.

Prodrug Linkage Bonds

When a prodrug moiety is attached to an ion channel modulating compound, either via a direct bond or via a linker, a linkage bond is formed that links or attaches the ion channel modulating compound to the prodrug moiety or linker. Typically, a linkage bond is a covalent linkage bond, such as a cleavable covalent bond. The cleavable covalent bond is usually cleaved by enzymatic or hydrolytic cleavage. Typical covalent linkage bonds that attach the prodrug moiety to the ion channel modulating compound include but are not limited to amides, carbamates, carbonates, ureas, disulfides, sulfonamides, sulfonates, thio-sulfonates, thio-ethers, thio-esters, ethers, esters, amines or the like.

A prodrug moiety may be attached to an ion channel modulating compound at any site suitable for its attachment, as discussed above in the section entitled "prodrug attachment site". Typically, the position on the ion channel modulating compound that is associated with or attached to a prodrug moiety is a functional group that, when associated with or attached to the prodrug moiety, forms a chemical bond that is amenable to enzymatic, non-enzymatic, non-hydrolytic or hydrolytic cleavage. The functional group on the ion channel modulating compound may be directly associated with a prodrug moiety, or may be converted into a subsequent functional group, which may then be associated with the prodrug moiety.

Illustrative examples of a functional group on the ion channel modulating compound that may be used for association with a prodrug moiety include but are not limited to a hydroxyl, an amino, an ether, an ester, a thio-ester, a thiol, an alkene, an alkyne, an alkyl, a carboxyl, a ketone, an aldehyde, a thio-aldehyde, a thioketone, a thio-carboxyl, an acyl-halide, a thio-acyl-halide, an alkanoyloxy, thio-alkanoyloxy, an alkoxycarbonyl, a thio-alkoxycarbonyl, an aryl, an aralkyl, an amide, a thio-amide, and a disulfide. In one variation, the functional group on the ion channel modulating compound that is used for association with or attachment to a prodrug moiety or linker is selected from the group consisting of an amino, alkoxy or hydroxy group.

Prodrug Linkers

A prodrug moiety may be attached to an ion channel modulating compound either directly (i.e. by a direct bond) or via a linker. Typically, a linker will be attached to an ion channel modulating compound via a cleavable covalent bond. The cleavable covalent bond is usually cleaved by enzymatic or hydrolytic cleavage.

A linker may be attached to an ion channel modulating compound via any linkage bond, including but not limited to those described in the previous section. Typical covalent bonds that attach a linker to an ion channel modulating compound include but are not limited to amides, carbamates, carbonates, ureas, disulfides, sulfonamides, sulfonates, thio-sulfonates, thio-ethers, thio-esters, ethers, esters, amines, or the like.

The linker may be of any size, from a small moiety that is used to facilitate the formation a linkage bond, to a larger group which is employed as a connector and/or spacer group. These groups are collectively referred to as "linkers."

Linkers may be used as a spacer molecule to create a separation between the ion channel modulating compound and the prodrug, and/or to avoid undesired steric interactions. The spatial separation may be desired for modified, enhanced, or optimal function of the prodrug. The linkers may also facilitate the preparation or use of the prodrug.

In synthesizing a prodrug comprising a linker, it may be useful to employ a linker that has at least two functional groups (such as a bifunctional linker), one for bonding of the linker to the ion channel modulating compound and one for bonding of the linker to the prodrug moiety. A multifunctional linker may also be used, such that 2, 3, 4 or more prodrug or other moieties may be attached to a single ion channel modulating compound. In one variation, a prodrug comprises a linker that is a bifunctional linker molecule. A bifunctional linker molecule comprises two reactive termini, one of which is available for linkage to the ion channel modulating compound and one of which is available for linkage to the prodrug moiety. The functional groups on the reactive termini may be the same or different, and are typically functional groups that are mutually reactive, or complementary to, reactive functional groups on the ion channel modulating compound and prodrug moiety that serve as attachment sites for the linker. Complementary functional groups would be readily recognized by one of skill in the art and depend upon the ion channel modulating compound and prodrug moiety for use in the prodrug.

A linker may be primarily hydrophobic in nature or may be primarily hydrophilic in nature and may thus contribute to the overall hydrophobicity or hydrophilicity of the prodrug. A single linker may also have both hydrophobic and hydrophilic regions contained within a single linker.

Specific Prodrugs

In one embodiment of the invention, the prodrug is an ester derivative of an ion channel modulating compound. An ester derivative of an ion channel modulating compound is a derivative of an ion channel modulating compound whereby a prodrug moiety is attached to the ion channel modulating compound via an ester linkage. An illustrative schematic diagram of an ester derivative of an ion channel modulating compound comprising a hydroxyl functionality is shown below, wherein R is as defined above in the section "prodrug moieties" In one variation, the ester derivative is an ester derivative of a compound of formulae (I), (IA) or (IX) and Compound A as described herein.

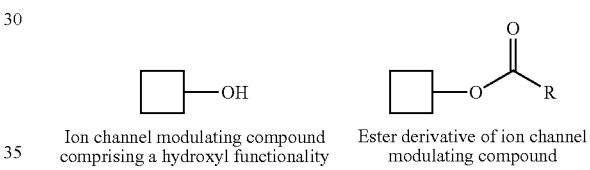

Ion channel modulating compound comprising a hydroxyl functionality

Ester derivative of ion channel modulating compound

In another embodiment of the invention, the prodrug is a carbamate derivative of an ion channel modulating compound. A carbamate derivative of an ion channel modulating compound is a derivative of an ion modulating compound whereby a prodrug moiety is attached to the ion channel modulating compound via a carbamate linkage. In still another embodiment, the prodrug is an ether derivative of an ion channel modulating compound. An ether derivative of an ion channel modulating compound is a derivative of an ion modulating compound whereby a prodrug moiety is attached to the ion channel modulating compound via an ether linkage.

In one embodiment, the prodrug comprises a cycloalkane ring wherein the cycloalkane ring may be a 5, 6, 7, or 8-membered cycloalkane ring. In some embodiments, a prodrug comprising a cycloalkane ring is further substituted with an ether moiety or an amino moiety or with both an ether and an amino moiety. In a particular embodiment, a prodrug comprises an amino-substituted cyclohexyl ether ring. In another embodiment, a prodrug comprises an amino-substituted cycloalkane ring, wherein the amino group is a pyrrolidinyl ring that may be optionally substituted, such as with a hydroxyl group, to provide a prodrug comprising a hydroxyl-substituted pyrrolidinyl ring. In another embodiment, a prodrug comprises a compound of formulae (I), (IA) or (IX) and Compound A as described herein with a prodrug moiety attached thereto.

Thus, in one embodiment, prodrugs of compounds of formula (I), i.e., prodrugs of the following formula (PRO), are provided:

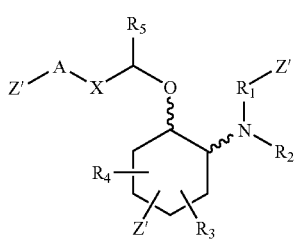

(PRO)

wherein, independently at each occurrence,

X is selected from a direct bond, —C(R$_6$,R$_4$)—Y— and —C(R$_{13}$)=CH—,

Y is selected from a direct bond, O, S and C$_1$-C$_4$alkylene;

R$_{13}$ is selected from hydrogen, C$_1$-C$_6$alkyl, C$_3$-C$_8$cycloalkyl, aryl and benzyl;

R$_1$ and R$_2$ are independently selected from hydrogen, C$_1$-C$_8$alkyl, C$_3$-C$_8$alkoxyalkyl, C$_1$-C$_8$hydroxyalkyl, and C$_7$-C$_{12}$aralkyl; or R$_1$ and R$_2$, when taken together with the nitrogen atom to which they are directly attached in formula (PRO-I), form a ring denoted by formula (PRO-II):

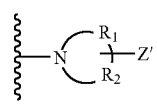

(PRO-II)

wherein the ring of formula (PRO-II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, C$_1$-C$_3$hydroxyalkyl, oxo, C$_2$-C$_4$acyl, C$_1$-C$_3$alkyl, C$_2$-C$_4$alkylcarboxy, C$_1$-C$_3$alkoxy, C$_1$-C$_{20}$alkanoyloxy, or may be substituted to form a spiro five- or six-membered heterocyclic ring containing one or two heteroatoms selected from oxygen and sulfur; and any two adjacent additional carbon ring atoms may be fused to a C$_3$-C$_8$carbocyclic ring, and any one or more of the additional nitrogen ring atoms may be substituted with substituents selected from hydrogen, C$_1$-C$_6$alkyl, C$_2$-C$_4$acyl, C$_2$-C$_4$hydroxyalkyl and C$_3$-C$_8$alkoxyalkyl; or R$_1$ and R$_2$, when taken together with the nitrogen atom to which they are directly attached in formula (PRO-I), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

R$_3$ and R$_4$ are independently attached to the cyclohexane ring shown in formula (PRO-I) at the 3-, 4-, 5- or 6-positions and are independently selected from hydrogen, hydroxy, C$_1$-C$_6$alkyl and C$_1$-C$_6$alkoxy, and, when both R$_3$ and R$_4$ are attached to the same cyclohexane ring atom, may together form a spiro five- or six-membered heterocyclic ring containing one or two heteroatoms selected from oxygen and sulfur;

R$_5$, R$_6$ and R$_{14}$ are independently selected from hydrogen, C$_1$-C$_6$alkyl, aryl and benzyl, or R$_5$ and R$_{14}$, when taken together with the carbon to which they are attached, may form a spiro C$_3$-C$_5$cycloalkyl;

each Z' is independently selected from hydrogen or a prodrug moiety with the proviso that at least one Z' in the prodrug of formula (PRO) is a prodrug moiety;

A is selected from C$_5$-C$_{12}$alkyl, a C$_3$-C$_{13}$carbocyclic ring, and ring systems selected from formulae (III), (IV), (V), (VI), (VII) and (VIII):

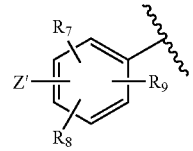

(PRO-III)

where R$_7$, R$_8$ and R$_9$ are independently selected from bromine, chlorine, fluorine, carboxy, hydrogen, hydroxy, hydroxymethyl, methanesulfonamido, nitro, sulfamyl, trifluoromethyl, C$_2$-C$_7$alkanoyloxy, C$_1$-C$_6$alkyl, C$_1$-C$_6$alkoxy, C$_2$-C$_7$alkoxycarbonyl, C$_1$-C$_6$thioalkyl and N(R$_{15}$,R$_{16}$) where R$_{15}$ and R$_{16}$ are independently selected from hydrogen, acetyl, methanesulfonyl and C$_1$-C$_6$alkyl;

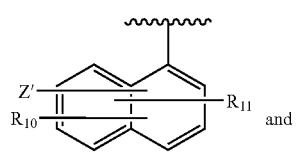

(PRO-IV)

and

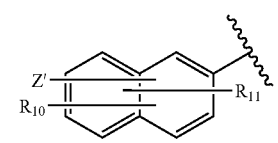

(PRO-V)

where R$_{10}$ and R$_{11}$ are independently selected from bromine, chlorine, fluorine, carboxy, hydrogen, hydroxy, hydroxymethyl, methanesulfonamido, nitro, sulfamyl, trifluoromethyl, C$_2$-C$_7$alkanoyloxy, C$_1$-C$_6$alkyl, C$_1$-C$_6$alkoxy, C$_2$-C$_7$alkoxycarbonyl, C$_1$-C$_6$thioalkyl, and N(R$_{15}$,R$_{16}$) where R$_{15}$ and R$_{16}$ are independently selected from hydrogen, acetyl, methanesulfonyl, and C$_1$-C$_6$alkyl;

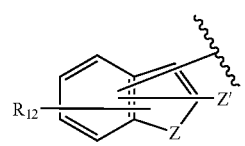

(PRO-VI)

where R$_{12}$ is selected from bromine, chlorine, fluorine, carboxy, hydrogen, hydroxy, hydroxymethyl, methanesulfonamido, nitro, sulfamyl, trifluoromethyl, C$_2$-C$_7$alkanoyloxy, C$_1$-C$_6$alkyl, C$_1$-C$_6$alkoxy, C$_2$-C$_7$alkoxycarbonyl, C$_1$-C$_6$thioalkyl, and N(R$_{15}$,R$_{16}$) where R$_{15}$ and R$_{16}$ are independently selected from hydrogen, acetyl, methanesulfonyl, and C$_1$-C$_6$alkyl; and Z is selected from CH, CH$_2$, O, N and S, where Z may be directly bonded to "X" as shown in formula (PRO-I) when Z is CH or N, or Z may be directly bonded to R$_{17}$ when Z is N, and R$_{17}$ is selected from hydrogen, C$_1$-C$_6$alkyl, C$_3$-C$_8$cycloalkyl, aryl and benzyl;

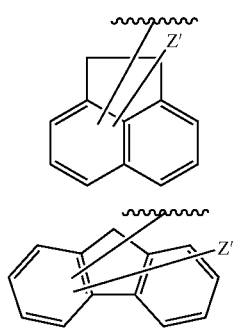

(PRO-VII)

(PRO-VIII)

as isolated enantiomeric, diastereomeric and geometric isomers thereof, and mixtures thereof, or pharmaceutically acceptable salts or solvates thereof.

In another embodiment, prodrugs of compounds of formula (I), i.e., prodrugs of the following formula (PRO-I), are provided:

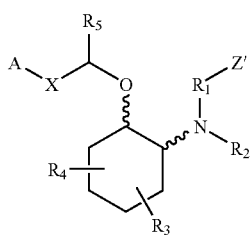

(PRO-I)

wherein, independently at each occurrence,

X is selected from a direct bond, —C($R_6,R_{14}$)—Y— and —C($R_{13}$)=CH—,

Y is selected from a direct bond, O, S and $C_1$-$C_4$alkylene;

$R_{13}$ is selected from hydrogen, $C_1$-$C_6$alkyl, $C_3$-$C_8$cycloalkyl, aryl and benzyl;

$R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached in formula (PRO-I), form a ring denoted by formula (PRO-II):

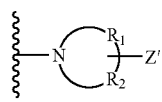

(PRO-II)

wherein the ring of formula (PRO-II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached in formula (PRO-I), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cyclohexane ring shown in formula (PRO-I) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

Z' is a prodrug moiety;

A is selected from $C_5$-$C_{12}$alkyl, a $C_3$-$C_{13}$-carbocyclic ring, and ring systems selected from formulae (III), (IV), (V), (VI), (VII) and (VIII):

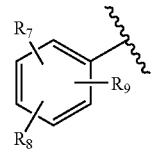

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and N($R_{15}$,$R_{16}$) where $R_{15}$ and $R_{16}$ are independently selected from hydrogen, acetyl, methanesulfonyl and $C_1$-$C_6$alkyl;

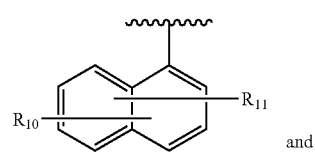

(IV)

and

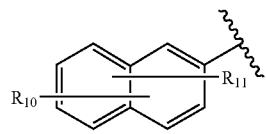

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$,$R_{16}$) where $R_{15}$ and $R_{16}$ are independently selected from hydrogen, acetyl, methanesulfonyl, and $C_1$-$C_6$alkyl;

(VI)

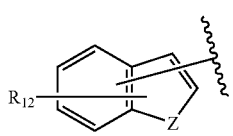

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (PRO-I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

(VII)

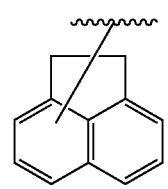

(VIII)

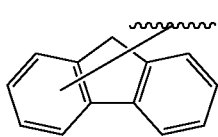

as isolated enantiomeric, diastereomeric and geometric isomers thereof, and mixtures thereof, or pharmaceutically acceptable salts or solvates thereof.

In another aspect, one or more prodrug moieties, as defined herein, may be attached to any suitable position on the compound of formula (I) to form additional prodrugs of compounds of formula (I), as illustrated below in the following FIG. 1, where Z', Za and Zb are each independently a prodrug moiety as described herein, and each A, X, $R_1$, $R_2$, $R_3$, $R_4$ and $R_5$ are defined as above for prodrugs of formula (PRO-I):

FIG. 1: Additional Prodrugs of Compounds of Formula (I)

(PRO-I)

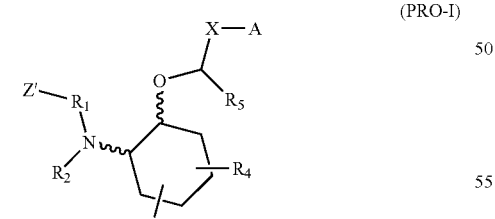

(PRO-Ia)

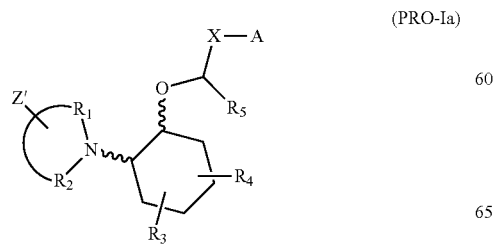

(PRO-Ib)

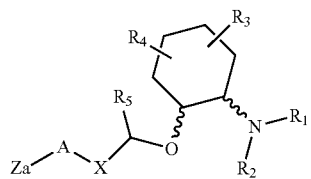

(PRO-Ic)

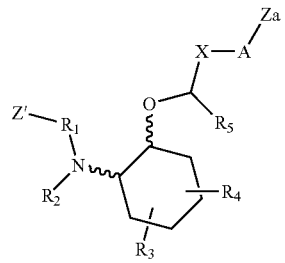

(PRO-Id)

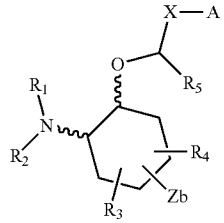

(PRO-Ie)

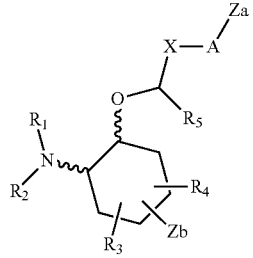

(PRO-If)

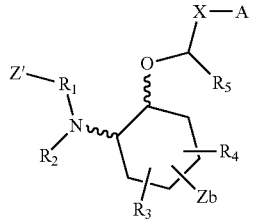

(PRO-Ig)

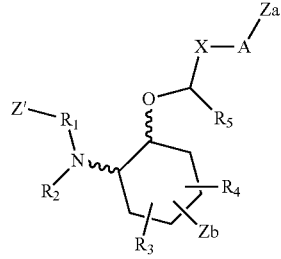

In another embodiment of the invention, prodrugs of compounds of formula (IA), i.e., prodrugs of the following formula (PRO-IA), are provided:

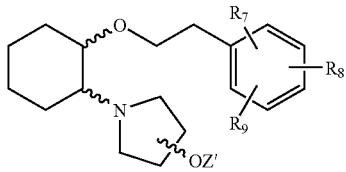

(PRO-IA)

wherein:

Z' is a prodrug moiety; and $R_7$, $R_8$ and $R_9$ are independently selected from hydrogen, hydroxy and $C_1$-$C_6$alkoxy, with the proviso that $R_7$, $R_8$ and $R_9$ cannot all be hydrogen;

as isolated enantiomeric, diastereomeric and geometric isomers thereof, and mixtures thereof, or pharmaceutically acceptable salts thereof.

In another embodiment, one or more prodrug moieties, as defined herein, may be attached to any suitable position on the compound of formula (IA) to form additional prodrugs of compounds of formula (IA), as illustrated below in FIG. 2 where each Z' and Za are independently a prodrug moiety, and $R_7$, $R_8$ and $R_9$ are as described above for prodrugs of formula (PRO-IA):

FIG. 2: Additional Prodrugs of Compounds of Formula (IA)

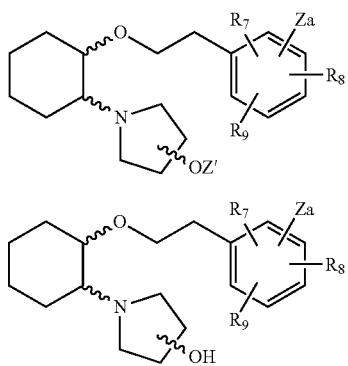

(PRO-IAa)

(PRO-IAb)

In another embodiment of the invention, prodrugs of compounds of formula (IX), i.e., prodrugs of the following formula (PRO-IX), are provided:

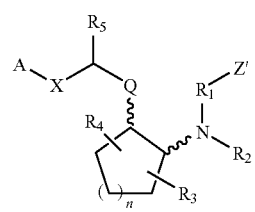

(PRO-IX)

wherein, independently at each occurrence, n is selected from 1, 3 and 4;

Q is either 0 (oxygen) or —O—C(O);

X is selected from a direct bond, —C($R_6$,$R_{14}$)—Y—, and —C($R_{13}$)═CH—;

Y is selected from a direct bond, O, S, and $C_1$-$C_4$alkylene;

$R_{13}$ is selected from hydrogen, $C_1$-$C_8$alkyl, $C_3$-$C_8$cycloalkyl, aryl, and benzyl;

$R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached in formula (PRO-IX), form a ring denoted by formula (PRO-II):

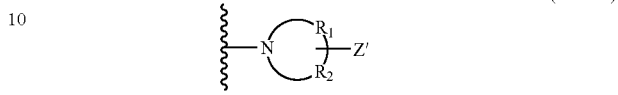

(PRO-II)

wherein the ring of formula (PRO-II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$-carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached in formula (PRO-IX), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cyclohexane ring shown in formula (PRO-IX) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

Z' is a prodrug moiety;

A is selected from $C_6$-$C_{12}$alkyl, a $C_3$-$C_{13}$carbocyclic ring, and ring systems selected from formulae (III), (IV), (V), (VI), (VII) and (VIII):

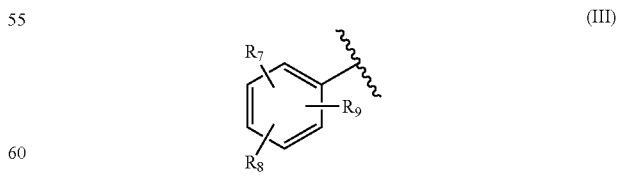

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and N($R_{15}$,$R_{16}$) where $R_{15}$ and $R_{16}$ are independently selected from hydrogen, acetyl, methanesulfonyl and $C_1$-$C_6$alkyl;

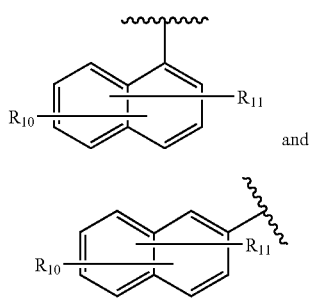
(IV)

and (V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl;

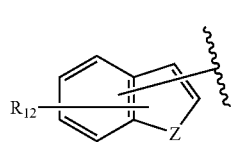
(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (PRO-IX) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

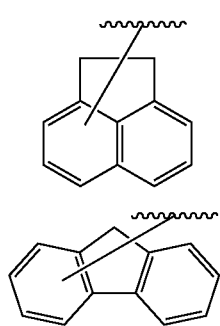
(VII)

(VIII)

as isolated enantiomeric, diastereomeric and geometric isomers thereof, and mixtures thereof, or pharmaceutically acceptable salts or solvates thereof.

In another embodiment of the invention, one or more prodrug moieties, as defined herein, may be attached to any suitable position on the compound of formula (IX) to form additional prodrugs of compounds of formula (PRO-IX), as illustrated below in the following FIG. 3, where Z', Za and Zb are each independently a prodrug moiety as described herein, and each n, A, Q, X, $R_1$, $R_2$, $R_3$, $R_4$ and $R_5$ are defined as above for prodrugs of formula (PRO-IX):

FIG. 3: Additional Prodrugs of Compounds of Formula (IX)

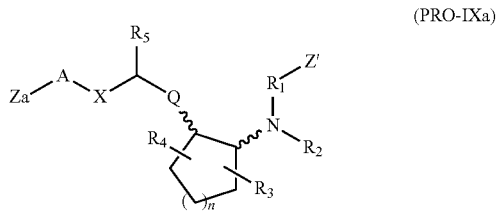
(PRO-IXa)

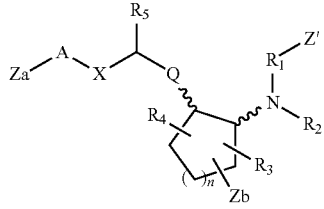
(PRO-IXb)

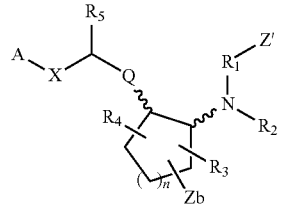
(PRO-IXc)

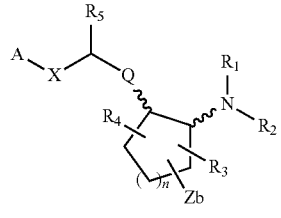
(PRO-IXd)

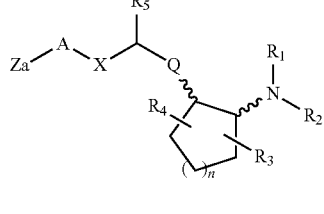
(PRO-IXe)

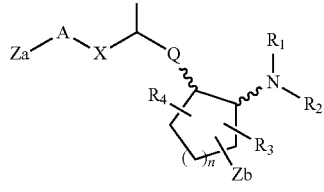
(PRO-IXe)

In another embodiment of the invention, prodrugs of Compound A, i.e., prodrugs of the following formula (PRO-A), are provided where Z' is a prodrug moiety:

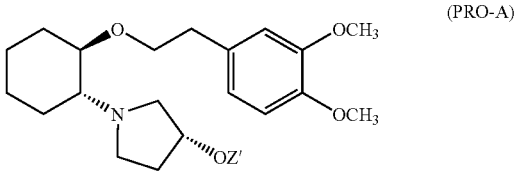
(PRO-A)

where Z' is a prodrug entity;
or pharmaceutically acceptable salts or solvates thereof.

In another aspect, one or more prodrug moieties, as defined herein, may be attached to other suitable positions on the compound of formula (A) to form additional prodrugs of compounds of formula (PRO-A), as illustrated below in the following FIG. 4, where Za and Zb are each independently a prodrug moiety as described herein:

FIG. 4: Additional Prodrugs of Compounds of Formula (A)

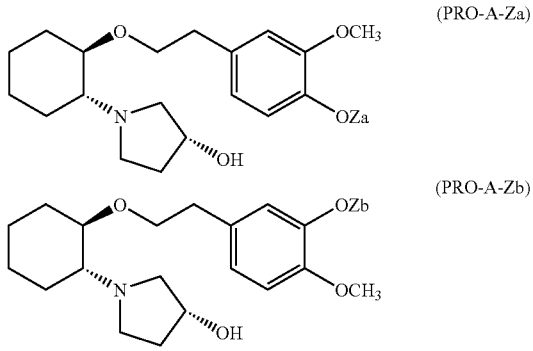

Preparation of the Above Prodrugs of the Invention, and their Degradation into the respective ion channel modulating compound of formulae (I), (IA), (IX) or Compound A, is described in more detail below in the section entitled "Preparation of Prodrugs of Ion Channel Modulating Compounds".

D. Administration of the Prodrugs of the Invention

The present invention provides a composition or medicament that includes one or more prodrugs of the invention, selected from any of the compounds, or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, as isolated enantiomeric, diastereomeric and geometric isomers thereof, and mixtures thereof, described above, in combination with a pharmaceutically acceptable carrier, diluent or excipient, and further provides a method for the manufacture of such a composition or medicament.

The present invention further provides a composition or medicament that includes one or more prodrugs of the invention, selected from any of the prodrugs, or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, as isolated enantiomeric, diastereomeric and geometric isomers thereof, and mixtures thereof, described above, in combination with appropriate amounts of sodium chloride USP, citric acid USP, sodium hydroxide NF and water for injection USP, and further provides a method for the manufacture of such a composition or medicament.

In other embodiments, the present invention provides a composition or medicament that includes a compound which is (1R,2R)-2-[(3R)-hydroxypyrrolidinyl]-1-(3,4-dimethoxyphenethoxy)-cyclohexane monohydrochloride, or any solvate thereof; in combination with appropriate amounts of sodium chloride USP, citric acid USP, sodium hydroxide NF and water for injection USP; and further provides a method for the manufacture of such a composition or medicament.

The present invention further provides a composition or medicament that includes one or more prodrugs of the invention, selected from any of the prodrugs, or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, as isolated enantiomeric, diastereomeric and geometric isomers thereof, and mixtures thereof, described above, in combination with appropriate amounts of sodium chloride USP, citric acid USP, sodium hydroxide NF and water for injection USP, that resulted in an isotonic intravenous solution of said compound at a concentration of about 0.1 mg/mL to 100 mg/mL in sodium citrate of about 1 to 400 nM at a pH of about 7.5 to 4.0; and further provides a method for the manufacture of such a composition or medicament.

The present invention further provides a composition or medicament that includes one or more prodrugs of the invention, selected from any of the prodrugs, or a solvate, pharmaceutically acceptable salt, ester, amide, complex, chelate, stereoisomer, stereoisomeric mixture, geometric isomer, crystalline or amorphous form, metabolite, or metabolic precursor, as isolated enantiomeric, diastereomeric and geometric isomers thereof, and mixtures thereof, described above, in combination with appropriate amounts of sodium chloride USP, citric acid USP, sodium hydroxide NF and water for injection USP, that resulted in an isotonic intravenous solution of said compound at a concentration of about 5 mg/mL to 80 mg/mL in sodium citrate of about 10 to 80 nM at a pH of about 6.5 to 4.5; and further provides a method for the manufacture of such a composition or medicament.

The present invention further provides a composition or medicament that includes one or more prodrugs of the invention, selected from any of the prodrugs, or a solvate, pharmaceutically acceptable salt, ester, amide, complex, chelate, stereoisomer, stereoisomeric mixture, geometric isomer, crystalline or amorphous form, metabolite, or metabolic precursor thereof, as isolated enantiomeric, diastereomeric and geometric isomers thereof, and mixtures thereof, described above, in combination with appropriate amounts of sodium chloride USP, citric acid USP, sodium hydroxide NF and water for injection USP, that resulted in an isotonic intravenous solution of said compound at a concentration of about 10 mg/mL to 40 mg/mL in sodium citrate of about 20 to 60 nM at a pH of about 6.0 to 5.0; and further provides a method for the manufacture of such a composition or medicament.

The present invention further provides a composition or medicament that includes one or more prodrugs of the invention, selected from any of the prodrugs, or a solvate, pharmaceutically acceptable salt, ester, amide, complex, chelate, stereoisomer, stereoisomeric mixture, geometric isomer, crystalline or amorphous form, metabolite, or metabolic precursor thereof, as isolated enantiomeric, diastereomeric and geometric isomers thereof, and mixtures thereof, described above, in combination with appropriate amounts of sodium chloride USP, citric acid USP, sodium hydroxide NF and water for injection USP, that resulted in an isotonic intravenous solution of said compound at a concentration of about 20 mg/mL in sodium citrate of about 40 nM at a pH of about 5.5; and further provides a method for the manufacture of such a composition or medicament.

In another embodiment, the present invention provides compositions which include a compound of the present invention in admixture or otherwise in association with one or more inert carriers, excipients and diluents, as well as optional ingredients if desired. These compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 75 wt % of the entire weight of the composition. Inert carriers include any material which does not degrade or otherwise covalently react with a compound of the invention. Examples of suitable inert carriers are water; aqueous buffers, such as those which are generally useful in High Performance Liquid Chromatography (HPLC) analysis; organic solvents such as acetonitrile, ethyl acetate, hexane and the like (which are suitable for use in in vitro diagnostics or assays, but typically are not suitable for administration to a warm-blooded animal); and pharmaceutically acceptable carriers, such as physiological saline.

Thus, the present invention provides a pharmaceutical or veterinary composition (hereinafter, simply referred to as a pharmaceutical composition) containing a compound of the present invention, in admixture with a pharmaceutically acceptable carrier, excipient or diluent. The invention further provides a pharmaceutical composition containing an effective amount of compound of the present invention, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques. Pharmaceutical compositions of the invention are formulated so as to allow the active ingredients contained therein to be bioavailable upon administration of the composition to a patient. Compositions that will be administered to a patient take the form of one or more dosage units, where for example, a tablet, capsule or cachet may be a single dosage unit, and a container of the compound in aerosol form may hold a plurality of dosage units.

Materials used in preparing the pharmaceutical compositions should be pharmaceutically pure and non-toxic in the amounts used. The inventive compositions may include one or more compounds (active ingredients) known for a particularly desirable effect. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a compound of the present invention as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, cachet, chewing gum, wafer, lozenges, or the like form. Such a solid composition will typically contain one or more inert diluents or edible carriers. In addition, one or more of the following adjuvants may be present: binders such as syrups, acacia, sorbitol, polyvinylpyrrolidone, carboxymethylcellulose, ethyl cellulose, microcrystalline cellulose, gum tragacanth or gelatin, and mixtures thereof; excipients such as starch, lactose or dextrins, disintegrating agents such as alginic acid, sodium alginate, Primogel, corn starch and the like; lubricants such as magnesium stearate or Sterotex; fillers such as lactose, mannitols, starch, calcium phosphate, sorbitol, methylcellulose, and mixtures thereof; lubricants such as magnesium stearate, high molecular weight polymers such as polyethylene glycol, high molecular weight fatty acids such as stearic acid, silica, wetting agents such as sodium lauryl sulfate, glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, aqueous or oily emulsion or suspension, or even dry powders which may be reconstituted with water and/or other liquid media prior to use. The liquid may be for oral administration or for delivery by injection, as two examples. When intended for oral administration, preferred compositions contain, in addition to the present compounds, one or more of a sweetening agent, thickening agent, preservative (e.g., alkyl p-hydroxybenzoate), dye/colorant and flavor enhancer (flavorant). In a composition intended to be administered by injection, one or more of a surfactant, preservative (e.g., alkyl p-hydroxybenzoate), wetting agent, dispersing agent, suspending agent (e.g., sorbitol, glucose, or other sugar syrups), buffer, stabilizer and isotonic agent may be included. The emulsifying agent may be selected from lecithin or sorbitol monooleate.

The liquid pharmaceutical compositions of the invention, whether they be solutions, suspensions or other like form, may include one or more of the following adjuvants: sterile diluents such as water for injection, saline solution, preferably physiological saline, Ringers solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active aminocyclohexyl ether compound. Preferred compositions and preparations according to the present invention are prepared so that a parenteral dosage unit contains between 0.01 to 10% by weight of active compound.

The pharmaceutical composition may be intended for topical administration, in which case the carrier may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 25% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the aminocyclohexyl ether compound is dispersed homogeneously therein by stirring. The molten homogeneous mixture is then poured into convenient sized molds, allowed to cool and thereby solidify.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The composition in solid or liquid form may include an agent which binds to the aminocyclohexyl ether compound and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of prodrugs of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in methods for either modulating ion channel activity in a warm-blooded animal or for modulating ion channel activity in vitro, or used in the treatment and/or prevention of arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g., diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, heart failure, atrial contractile dysfunction, hypotension, Alzheimer's disease, dementia and other mental disorders, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer or other diseases. Other agents known to cause libido enhancement, analgesia or local anesthesia may be combined with compounds of the present invention.

The compositions may be prepared by methodology well known in the pharmaceutical art. The aminocyclohexyl ether compounds of the present invention may be in the form of a solvate in a pharmaceutically acceptable solvent such as water or physiological saline. Alternatively, the compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

A composition intended to be administered by injection can be prepared by combining the aminocyclohexyl ether compound of the present invention with water, and preferably buffering agents, so as to form a solution. The water is preferably sterile pyrogen-free water. A surfactant may be added to facilitate the formation of a homogeneous solution or suspension. Surfactants are compounds that non-covalently interact with the aminocyclohexyl ether compound so as to facilitate dissolution or homogeneous suspension of the aminocyclohexyl ether compound in the aqueous delivery system. Surfactants are desirably present in aqueous compositions of the invention because the aminocyclohexyl ether compounds according to the present invention may be hydrophobic. Other carriers for injection include, without limitation, sterile peroxide-free ethyl oleate, dehydrated alcohols, propylene glycol, as well as mixtures thereof.

Suitable pharmaceutical adjuvants for the injecting solutions include stabilizing agents, solubilizing agents, buffers, and viscosity regulators. Examples of these adjuvants include ethanol, ethylenediaminetetraacetic acid (EDTA), tartrate buffers, citrate buffers, and high molecular weight polyethylene oxide viscosity regulators. These pharmaceutical formulations may be injected intramuscularly, epidurally, intraperitoneally, or intravenously.

As used herein, "treating arrhythmia" refers to therapy for arrhythmia. An effective amount of a composition of the present invention is used to treat arrhythmia in a warm-blooded animal, such as a human. Methods of administering effective amounts of antiarrhythmic agents are well known in the art and include the administration of an oral or parenteral dosage form. Such dosage forms include, but are not limited to, parenteral dosage form. Such dosage forms include, but are not limited to, parenteral solutions, tablets, capsules, sustained release implants, and transdermal delivery systems. Generally, oral or intravenous administration is preferred for some treatments. The dosage amount and frequency are selected to create an effective level of the agent without harmful effects. It will generally range from a dosage of from about 0.01 to about 100 mg/kg/day, and typically from about 0.1 to 10 mg/kg where administered orally or intravenously for antiarrhythmic effect or other therapeutic application.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocyclohexyl ether compound of the invention may be co-administered with epinephrine in order to induce local anesthesia.

E. Utility and Testing of the Prodrugs of the Invention

The present invention provides one or more prodrugs of ion channel modulating compounds, or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above, for use in methods for modulating ion channel activity in a warm-blooded animal or for modulating ion channel activity in vitro. In one version of this embodiment, the warm-blooded animal in which the ion channel activity is modulated is a mammal; in one version, the warm-blooded animal is a human; in one version, the warm-blooded animal is a farm animal.

As disclosed within the present invention, a variety of cardiac pathological conditions may be treated and/or prevented by the use of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above. These compounds of the present invention are ion channel modulating compounds that either singly or together with one or more additional compounds are able to selectively modulate certain ionic currents. The ion currents referred to herein are generally cardiac currents and more specifically, are the sodium currents and early repolarising currents.

Early repolarising currents correspond to those cardiac ionic currents which activate rapidly after depolarization of membrane voltage and which effect repolarisation of the cell. Many of these currents are potassium currents and may include, but are not limited to, the transient outward current $I_{to1}$ such as Kv4.2 and Kv4.3), and the ultrarapid delayed rectifier current ($I_{Kur}$) such as Kv1.5, Kv1.4 and Kv2.1). The ultrarapid delayed rectifier current ($I_{Kur}$) has also been described as $I_{sus}$. A second calcium dependent transient outward current ($I_{to2}$) has also been described.

The pathological conditions that may be treated and/or prevented by the present invention may include, but are not limited to, various cardiovascular diseases.

The cardiac pathological conditions that may be treated and/or prevented by the present invention may include, but are not limited to, arrhythmias such as the various types of atrial and ventricular arrhythmias, e.g., atrial fibrillation, atrial flutter, ventricular fibrillation and ventricular flutter.

In one embodiment, the present invention provides prodrugs of ion channel modulating compounds that can be used to selectively inhibit cardiac early repolarising currents and cardiac sodium currents.

In another embodiment, the present invention provides prodrugs of ion channel modulating compounds that can be used to selectively inhibit cardiac early repolarising currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity resulting from ischaemia or inflammation. Changes such as these are observed during conditions of myocardial ischaemia or inflammation and those conditions that precede the onset of arrhythmias such as atrial fibrillation.

In other embodiments, the present invention provides a method for modulating ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for modulating ion channel activity in an in vitro setting comprising administering in vitro an effective amount of one or more prodrugs of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said prodrug or mixture comprising compounds as described above.

In other embodiments, the present invention provides a method for blocking/inhibiting the activity/conductance of ion channel in a warm-blooded animal comprising administering to a warm-blooded animal in need thereof, an effective amount of one or more prodrugs of the present invention or solvates, pharmaceutically acceptable salts, esters, amides, complexes, chelates, stereoisomers, stereoisomeric mixtures, geometric isomers, crystalline or amorphous forms, metabolites, or metabolic precursors, as isolated enantiomeric, diastereomeric and geometric isomers thereof, and mixtures thereof; or a composition or medicament that includes said prodrug or mixture comprising compounds as described above.

In other embodiments, the present invention provides a method for blocking/inhibiting the activity/conductance of ion channel in an in vitro setting comprising administering in vitro an effective amount of one or more prodrugs of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for modulating potassium ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for modulating voltage-gated potassium ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, and mixtures thereof; or a composition or medicament that includes said compound or mixture comprising compounds as described above.

In other embodiments, the present invention provides a method for modulating cardiac sodium currents activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, and mixtures thereof; or a composition or medicament that includes said compound or mixture comprising compounds as described above.

In other embodiments, the present invention provides a method for modulating cardiac early repolarising currents and cardiac sodium currents ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting cardiac early repolarising currents and cardiac sodium currents ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting the cardiac ion channels responsible for cardiac early repolarising currents and cardiac sodium currents ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting cardiac early repolarising currents and cardiac sodium currents ion channel activity in a warm-blooded animal under conditions where an arrhythmogenic substrate is present in the heart of said warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, and mixtures thereof; or a composition or medicament that includes said compound or mixture comprising compounds as described above.

In other embodiments, the present invention provides a method for blocking/inhibiting the cardiac ion channels responsible for cardiac early repolarising currents and cardiac sodium currents ion channel activity in a warm-blooded animal under conditions where an arrhythmogenic substrate is present in the heart of said warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, and mixtures thereof; or a composition or medicament that includes said compound or mixture comprising compounds as described above.

In other embodiments, the cardiac early repolarising currents referred to in the present invention comprise ionic currents which activate rapidly after depolarisation of membrane voltage and which effect repolarisation of the cell.

In other embodiments, the cardiac early repolarising currents referred to in the present invention comprise the cardiac transient outward potassium current (Ito) and/or the ultrarapid delayed rectifier current ($I_{Kur}$)

In other embodiments, the cardiac transient outward potassium current ($I_{to}$) and/or the ultrarapid delayed rectifier current ($I_{Kur}$) referred to in the present invention comprise at least one of the Kv4.2, Kv4.3, Kv2.1, Kv1.4 and Kv1.5 currents.

In other embodiments, the present invention provides a method for treating and/or preventing arrhythmia in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial arrhythmia in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular arrhythmia in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial fibrillation in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular fibrillation in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial flutter in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular flutter in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, or metabolic precursors thereof, as isolated enantiomeric, diastereomeric and geometric isomers thereof, and mixtures thereof; or a composition or medicament that includes said compound or mixture comprising compounds as described above.

As noted above, the present invention provides for utilizing the compounds described above in in vitro and in vivo methods. In one embodiment, ion channels, such as cardiac potassium channels, are blocked in vitro or in vivo.

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

Accordingly, compounds that are capable of modulating the activity or function of the appropriate ion channels will be useful in treating and/or preventing a variety of diseases or disorders caused by defective or inadequate function of the ion channels. The prodrugs of the invention are found to have significant activity in modulating various ion channel activity both in vivo and in vitro.

In one embodiment, the present invention provides a compound of the present invention or a composition containing said compound, for use in methods for either modulating ion channel activity in a warm-blooded animal or for modulating ion channel activity in vitro. Some of the ion channels to which the compounds, compositions and methods of the present invention have modulating effect are various potassium and sodium channels. These potassium and sodium ion channels may be voltage-activated (also known as voltage-gated) or ligand-activated (also known as ligand-gated), and may be present in cardiac and/or neuronal systems.

In one embodiment, the invention provides a compound of the present invention, or composition containing said compound, for use in methods for either modulating activity of ion channel(s) in a warm-blooded animal or for modulating activity of ion channel(s) in vitro, wherein said ion channel(s) correspond to some of the cardiac and/or neuronal ion channels that are responsible for one or more early repolarising currents comprising those which activate rapidly after membrane depolarisation and which effect repolarisation of the cells.

In another embodiment, of the present invention, the above-mentioned early repolarising currents comprise the transient outward potassium current ($I_{to}$ for cardiac or $I_A$ for neuronal) and/or the ultrarapid delayed rectifier current ($I_{Kur}$); and include at least one of the Kv4.2, Kv4.3, Kv2.1, Kv1.3, Kv1.4 and Kv1.5 currents.

In another embodiment, the present invention provides a compound of the present invention, or composition containing said compound, for use in methods for either modulating activity of ion channel(s) in a warm-blooded animal or for modulating activity of ion channel(s) in vitro, wherein said ion channel(s) correspond to either the cardiac or neuronal ion channel(s) that are responsible for Kv1.5 current.

In yet another embodiment, the present invention provides a compound of the present invention, or composition containing said compound, for use in methods for either modulating activity of ion channel(s) in a warm-blooded animal or for modulating activity of ion channel(s) in vitro, wherein said ion channel(s) correspond to the potassium channel that are responsible for Kv4.2 current.

Furthermore, the voltage-activated sodium ion channels comprise the $Na_v1$, $Na_v2$ or $Na_v3$ series and may be present in cardiac, neuronal, skeletal muscle, central nervous and/or peripheral nervous systems (e.g., hH1Na).

For cardiac sodium channels, in studies on ion channels in isolated human atrial myocytes, compounds of the present invention have been shown to produce frequency-dependent blockade of cardiac sodium channels. In these studies enhanced blockade of cardiac sodium channels was observed at faster rates of stimulation with sodium block increasing several-fold during rapid stimulation rates. These protocols have been designed to mimic the short recovery intervals during fibrillation.

As noted earlier, modulating the activity of an ion channel as used above may imply but does not limit to blocking or inhibiting the conductance of the current through the ion channel.

Thus, the present invention provides for methods of treating a disease or condition in a warm-blooded animal suffering from or having the disease or condition, and/or preventing a disease or condition from arising in a warm-blooded animal, wherein a therapeutically effective amount of a compound of the present invention, or a composition containing a compound of the present invention is administered to a warm-blooded animal in need thereof. Some of the diseases and conditions to which the compounds, compositions and methods of the present invention may be applied are as follows: arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g., diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, heart failure, atrial contractile dysfunction, hypotension, Alzheimer's disease, dementia and other mental disorder, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer.

Furthermore, the present invention provides a method for producing analgesia or local anesthesia in a warm-blooded animal which includes administering to a warm-blooded animal in need thereof an effective amount of a compound of the present invention or a pharmaceutical composition containing said compound. These methods may be used to relieve or forestall the sensation of pain in a warm-blooded animal.

The invention further provides a method for enhancing libido in a warm-blooded animal which includes administering to a warm-blooded animal in need thereof an effective amount of a compound of the present invention or a pharmaceutical composition containing said compound. These compositions and methods may be used, for example, to treat a sexual dysfunction, e.g., impotence in males, and/or to enhance the sexual desire of a patient without a sexual dysfunction. As another example, the therapeutically effective amount may be administered to a bull (or other breeding stock), to promote increased semen ejaculation, where the ejaculated semen is collected and stored for use as it is needed to impregnate female cows in promotion of a breeding program.

Furthermore, the present invention provides a method in an in vitro setting, wherein a preparation that contains ion channels is contacted with an effective amount of an aminocyclohexyl ether compound of the invention. Suitable preparations containing cardiac sodium channels and/or cardiac potassium channels include cells isolated from cardiac tissue as well as cultured cell lines. The step of contacting includes, for example, incubation of ion channels with a compound under conditions and for a time sufficient to permit modulation of the activity of the channels by the compound.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocyclohexyl ether compound of the invention may be co-administered with epinephrine in order to induce local anesthesia.

In order to assess whether a compound has a desired pharmacological activity with the present invention, it may be subjected to a series of tests. The precise test to employ will depend on the physiological response of interest. The published literature contains numerous protocols for testing the efficacy of a potential therapeutic agent, and these protocols may be employed with the present compounds and compositions.

For example, in connection with treatment or prevention of arrhythmia, a series of four tests may be conducted. In the first of these tests, a compound of the present invention is given as increasing (doubling with each dose) intravenous infusion every 5 minutes to a conscious rat. The effects of the compound on blood pressure, heart rate and the ECG are measured continuously. Increasing doses are given until a severe adverse event occurs. The drug related adverse event is identified as being of respiratory, central nervous system or cardiovascular system origin. This test gives an indication as to whether the compound is modulating the activity of sodium channels and/or potassium channels, and in addition gives information about acute toxicity. The indices of sodium channel blockade are increasing P-R interval and QRS widening of the ECG. Potassium channel blockade results in Q-T interval prolongation of the ECG.

A second test involves administration of a compound as an infusion to pentobarbital anesthetized rats in which the left ventricle is subjected to electrical square wave stimulation performed according to a preset protocol described in further detail below. This protocol includes the determination of thresholds for induction of extrasystoles and ventricular fibrillation. In addition, effects on electrical refractoriness are assessed by a single extra beat technique. In addition effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q-T intervals of the ECG.

A third test involves exposing isolated rat hearts to increasing concentrations of a compound. Ventricular pressures, heart rate, conduction velocity and ECG are recorded in the isolated heart in the presence of varying concentrations of the compound. The test provides evidence for direct toxic effects on the myocardium. Additionally, selectivity, potency and efficacy of action of a compound can be ascertained under conditions simulating ischemia. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate under normal conditions.

All of the foregoing tests may be performed using rat tissue. In order to ensure that a compound is not having effects which are only specific to rat tissue, further experiments may be performed in dogs and primates. In order to assess possible sodium channel and potassium channel blocking action in vivo in dogs, a compound is tested for effects on the ECG, ventricular epicardial conduction velocity and responses to electrical stimulation. An anesthetized dog is subjected to an open chest procedure to expose the left ventricular epicardium. After the pericardium is removed from the heart a recording/stimulation electrode is sewn onto the epicardial surface of the left ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time possible toxic effects of a compound on the dog's cardiovascular system is assessed.

The effects of a compound on the ECG and responses to electrical stimulation are also assessed in intact, anesthetized monkeys (*Macaca fascicularis*). In this preparation, a blood pressure cannula and ECG electrodes are suitably placed in an anesthetized monkey. In addition, a stimulating electrode is placed onto the right atria and/or ventricle, together with monophasic action potential electrode. As in the tests described above, ECG and electrical stimulation response to a compound reveal the possible presence of sodium and/or potassium channel blockade. The monophasic action potential also reveals whether a compound widens the action potential, an action expected of a potassium channel blocker.

As another example, in connection with the mitigation or prevention of the sensation of pain, the following test may be performed. To determine the effects of a compound of the present invention on an animal's response to a sharp pain sensation, the effects of a slight prick from a 7.5 g weighted syringe fitted with a 23G needle as applied to the shaved back of a guinea pig (*Cavia porcellus*) is assessed following subcutaneous administration of sufficient (50 μL, 10 mg/mL) solution in saline to raise a visible bleb on the skin. Each test is performed on the central area of the bleb and also on its periphery to check for diffusion of the test solution from the point of administration. If the test animal produces a flinch in response to the stimulus, this demonstrates the absence of blockade of pain sensation. Testing may be carried out at intervals for up to 8 hours or more post-administration. The sites of bleb formation are examined after 24 hours to check for skin abnormalities consequent to local administration of test substances or of the vehicle used for preparation of the test solutions.

F. Preparation of the Compounds of Formula (I), (IA), (IX) and Compound A

The ion channel modulating compounds of formulae (I), (IA) and/or (IX) and/or Compound A used in the present invention may be prepared as described in PCT Published Patent Application No. WO 1999/50225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. WO 2005002693; or may be prepared by methods known to one skilled in the art.

G. Preparation of Prodrugs of Ion Channel Modulating Compounds

The prodrugs of ion channel modulating compounds described above are generally prepared by treating the respective ion channel modulating compound, in particular, a compound of formula (I), formula (IA), formula (IX) or Compound A, with a chemical entity allowing for the attachment of the Z', Za, or Zb group to the ion channel modulating compound. The methods may comprise of conjugation of an ion channel modulating compound to an additional drug moiety via a linker. The scheme below for compounds of formula (I) is generally applicable to all ion channel modulating compounds described above which comprise an aminocycloalkyl ether moiety. In the scheme below, Z', Za' and Zb represent prodrug moieties as described herein.

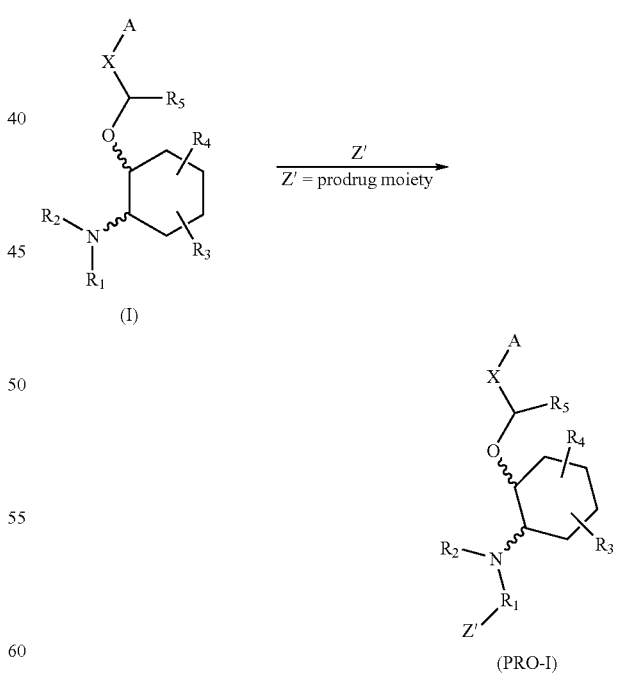

The prodrugs described herein may be in the form of a pharmaceutically acceptable salt. In one variation, the prodrug comprises a quaternary amine salt.

Upon administration of the compound to a subject, the prodrugs of the invention undergo an enzymatic degradation to produce the corresponding ion channel modulating compound, particularly the compound of formula (I), formula (IA), formula (IX) or Compound A as described above and in more detail below.

In general, a prodrug of the invention may be formed by the reaction of a prodrug moiety or linker with an in channel modulating compound under conditions appropriate to form a linkage bond between the ion channel modulating compound and the prodrug moiety or linker. If a linker is used, a subsequent step of reacting a prodrug moiety with the linker under conditions appropriate to attach the prodrug moiety to the linker may be required, or alternatively, the attachment of the prodrug moiety to the linker may take place prior to attachment of the linker to the ion channel modulating compound.

It is understood that in the following description, combinations of substituents and/or variables of any depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1999), 3rd Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following Reaction Schemes illustrate methods to make compounds of this invention. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention. If applicable, the following parameters were determined:

Melting points were determined on a Fisher-Johns apparatus and are uncorrected. NMR spectra were acquired in the indicated solvent on a Brucker AC-200, Varian XL-300, Brucker AV-300 or AV-400. Mass spectra were recorded for EI on a Kratos MS50, for FAB/LSIMS on a Kratos Concept IIHQ and for ES on a Micromass (Waters) Quattro (I) MSMS, connected to a HP1090 Series 2 LC (Agilent), controlled by Masslynx version 3.3 software. Elemental analyses were performed on an Element Analyzer 1108 by D. & H. Malhow, University of Alberta, Edmonton, AB (where analyses were indicated only by symbols of the elements, analytical results were within ±0.4% of the theoretical values). Whenever elemental analyses were not available, purity was determined by HPLC and capillary electrophoresis (CE). HPLC analyses were performed using a Gilson HPLC system (Gilson, Middleton, Wis.) with UV detection at 200 nm. A $C_{18}$ column with 150×4.6 mm, 5μ particle size was used. The mobile phase was delivered isocratically or as a gradient at a flow rate of 1 mL/min and consisted of a combination of phosphate buffer (low or high pH) and acetonitrile. Samples were prepared at ~100 μg/mL in mobile phase and 20 μL were injected into the HPLC. Purity was expressed in area %. CE analyses were performed using a P/ACE System MDQ (Beckman Coulter, Fullerton, Calif.). Uncoated silica capillaries with 60 (50 to detector) cm length and 75 μm internal diameter were used. The run buffer used was 100 mM sodium phosphate (pH 2.5). The separation voltage was either 23 or 25 kV (normal polarity) and the capillary cartridge temperature was maintained at 20° C. Samples (~0.5 mg/mL in water) were injected by pressure at 0.5 psi for 6 seconds. Detection was by UV at 200 or 213 nm. Purity was expressed in area %. IR spectral data were recorded on a Perkin-Elmer 983G spectrophotometer. Optical rotations were performed by F. Hoffman-La Roche Ltd (CH, Basel). Thin layer chromatography (TLC) was performed on E. Merck, TLC aluminum sheets 20×20 cm, Silica gel 60 $F_{254}$ plates. Flash chromatography was performed on E.M. Science silica gel 60 (70-230 mesh). Dry flash chromatography was performed with Sigma silica gel type H. Chromatotron chromatography (Harisson Research, USA) was performed on 4 mm plate with EM Science silica gel 60P $F_{254}$ with Gypsum or aluminum oxide 60P $F_{254}$ with Gypsum (type E). Preparative HPLC were performed on a Waters Delta Prep 4000 with a cartridge column (porasil, 10 μm, 125 Å, 40 mm×100 mm). GC analyses were performed on a Hewlett Packard HP 6890 equipped with 30 m×0.25 mm×0.25 μm capillary column HP-35 (crosslinked 35% PH ME siloxane) and a flame-ionization detector. High-boiling solvents (DMF, DMSO) were Sure/Seal™ from Aldrich, and tetrahydrofuran (THF) and ethylene glycol dimethyl ether (DME) were distilled from sodium-benzophenone ketyl. Organic extracts were dried with $Na_2SO_4$ unless otherwise noted. All moisture sensitive reactions were performed in dried glassware under a nitrogen or argon atmosphere.

Although anyone skilled in the art is capable of preparing the compounds of the invention according to the general techniques disclosed above, more specific details on synthetic techniques for compositions of the invention are provided elsewhere in this specification for convenience. Again, all reagents and reaction conditions employed in synthesis are known to those skilled in the art and are available from ordinary commercial sources.

The syntheses of compounds of this invention and their degradation into the respective ion channel modulating compounds are illustrated by, but not limited to the following examples and reaction schemes.

Example 1

The following Reaction Scheme 1 illustrates the intramolecular cyclization-elimination reaction transformation of a carbamate derivative prodrug of the present invention (PRO-A1) to the respective Compound A and prodrug moiety:

REACTION SCHEME 1

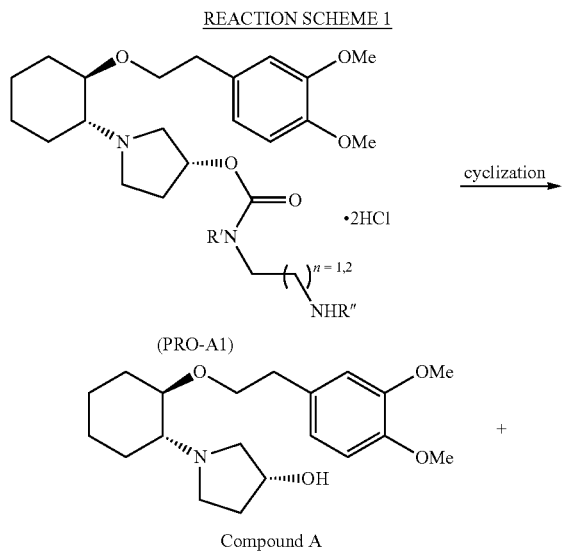

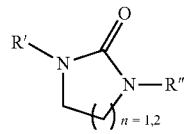

Reaction Scheme 1 shows a transformation process that may occur in the release of an ion channel modulating compound, such as Compound A, from a prodrug, such as the prodrug of formula (PRO-A1). In this example, an intramolecular cyclization-elimination reaction transformation is depicted. In this way, generation of the parent ion channel modulating compound, such as Compound A, does not only depend upon the host environments, but may also normally depend upon the rate of the cyclization reaction, which generally depends on factors such as: pH of the environment, length of the linkage between the two nitrogen atoms (NR' and NHR") and, the nature of the R' and R" groups on the nitrogen atoms (NR' and NHR" as reported by Saari et al. (Saari, W. S.; Schwering, J. E.; Lyle, P. A.; Smith, S. J.; Engelhardt, E. L. *J. Med. Chem.* 1990, 33, 97-101), a series of basic carbamates of 4-hydroxyanisole was synthesized and evaluated as progenitors of this melanocytotoxic phenol. In all cases, 4-hydroxyanisole was generated cleanly but at different rates depending upon the structure of the specific carbamate. Furthermore, kinetic data indicated that the hydrolysis rate follows first-order kinetics).)

In Reaction Scheme 1, which is generally applicable to prodrugs comprising a carbamate derivative of an ion channel modulating compound, R' and R" in the carbamate linker functional group of the prodrug of formula (PRO-A1) are selected from hydrogen or $C_1$-$C_6$-alkyl. In one aspect, R' and R" of the prodrug of formula (PRO-A1) are both methyl groups.

Synthesis of a prodrug, such as that shown above in formula (PRO-A1) with the basic carbamate linker functional group may be carried out according to a process shown below in Reaction Scheme 1A. The process is generally applicable for any ion channel modulating compound comprising a hydroxyl functionality, although alternate processes may also be carried out.

REACTION SCHEME 1A

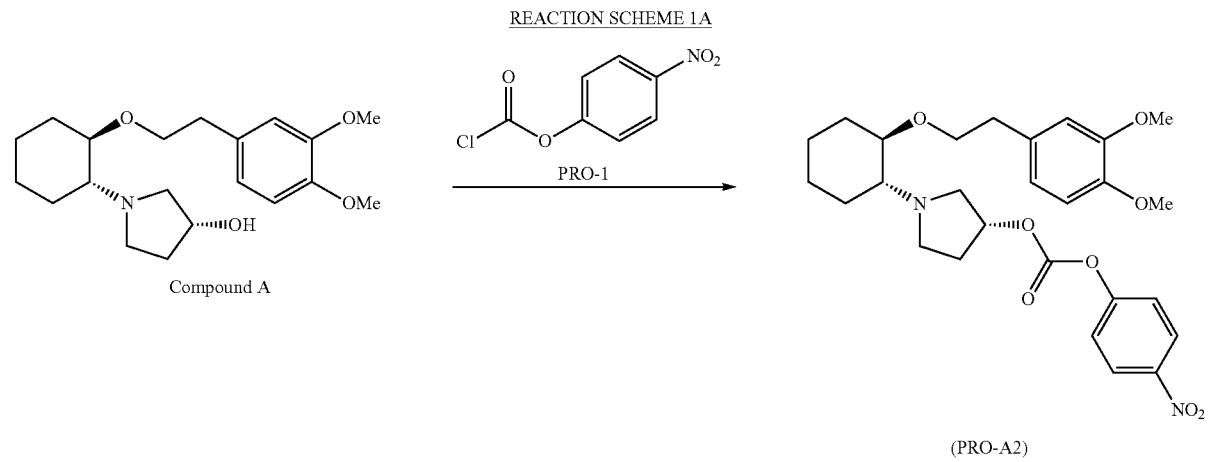

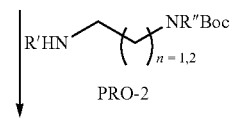

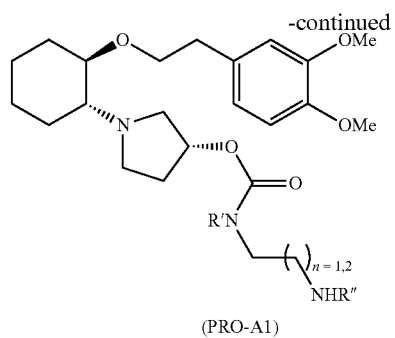

(PRO-A1)

HCl/EtOAc ←

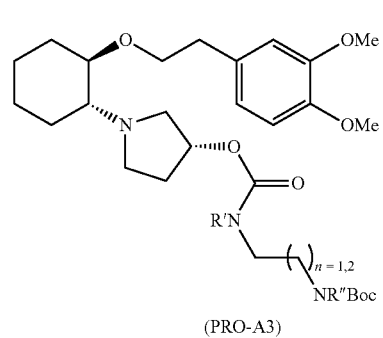

(PRO-A3)

In the first step of Reaction Scheme 1A, activation of the 3-pyrrolidinol functionality of Compound A to carbonate (PRO-A2) with 4-nitrophenyl chloroformate (PRO-1) may be carried out in a mixture of anhydrous THF-dichloromethane in the presence of pyridine (3 equiv.) at 0° C. for 2 h and then at ambient temperature for 18 h (see, de Groot, F. M. H. et al. J. Org. Chem. 2001, 66, 8815-8830). Reaction of carbonate (PRO-A2) with BOC-protected diamines (PRO-2) in the presence of N,N-diisopropylamine (1 equiv.) in THF at 0° C. for 30 min and then at ambient temperature for a further 20 h may result in the formation of the BOC-protected carbamate (PRO-A3). Monoprotected diamine intermediates (PRO-2) which could ultimately be deblocked in the last step without destruction of the carbamate functionality may be prepared according to literature methods (see, Saari, W. S.; Schwering, J. E.; Lyle, P. A.; Smith, S. J.; Engelhardt, E. L. *J. Med. Chem.* 1990, 33, 97-101). The tert-butoxycarbonyl (BOC) group may be used for that approach. Syntheses of mono-alkoxycarbonyl-protected diamines are extensively reported in the literature (Hansen, J. B.; Nielsen, M. C.; Erhbar, U.; Buchardt, O. *Synthesis* 1982, 404; Fuchs, S.; Klinger, W.; Voelter, W. *Liebigs Ann. Chem.* 1977, 602; Geiger, R. *Justus Liebigs Ann. Chem.* 1971, 750, 165; Herrin, T. R.; Pauviik, J. M.; Schuber, E. V.; Geiszler, A. O. *J. Med. Chem.* 1975, 18, 1216; Houssin, R.; Bernier, J. L.; Henichart, J.-P. *Synthesis* 1988, 259; Atwell, G. J.; Denny, W. A. *Synthesis* 1984, 1032). In a typical experiment, direct acylation of excess diamine with di-tert-butyl dicarbonate (⅓ molar equiv.) in THF is a convenient source of the protected diamines (PRO-2). BOC-protected carbamate (PRO-A3) may be isolated by standard procedures well known in the art. The basic carbamates (PRO-A1) may be obtained by treatment of compound (PRO-A3) with anhydrous hydrogen chloride in a suitable solvent such as ethyl acetate.

Example 2

The following Reaction Scheme 2 illustrates the intramolecular cyclization-elimination reaction transformation of an ester derivative prodrug (PRO-A5) to the respective Compound A and prodrug moiety:

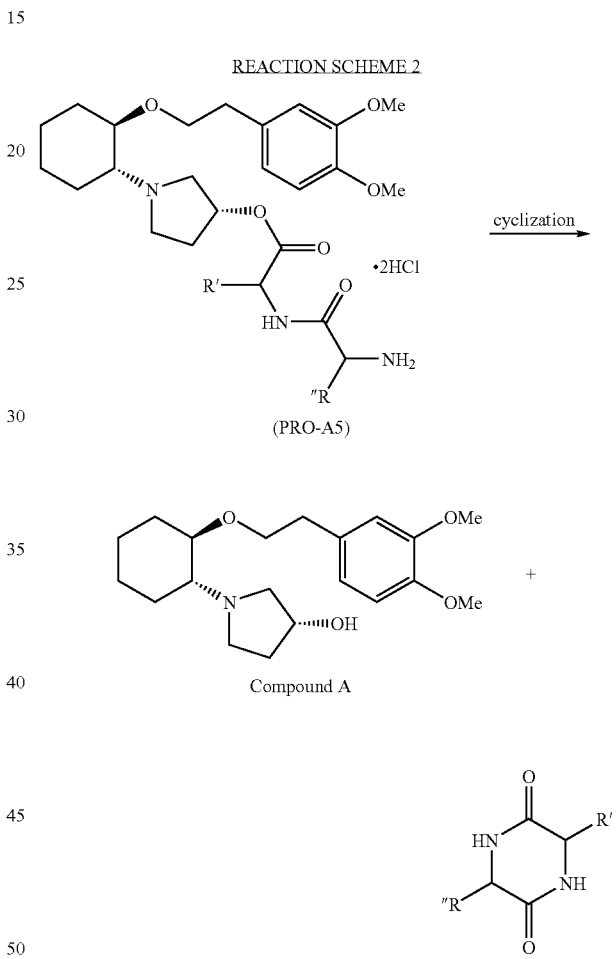

Reaction Scheme 2, which is generally applicable to prodrugs comprising an ester derivative of an ion channel modulating compound, shows a transformation process that may occur in the release of an Ion channel modulating compound, such as Compound A, from an ester derivative prodrug, such as formula (PRO-A5). In this instance, the transformation involves an intramolecular cyclization-elimination reaction. R' and R" of prodrug of formula (PRO-A5) are selected from hydrogen or $C_1$-$C_8$-alkyl.

Synthesis of the prodrug of formula (PRO-A5) above with the basic ester linker functional group may be carried out according to a process shown in Reaction Scheme 2A:

REACTION SCHEME 2A

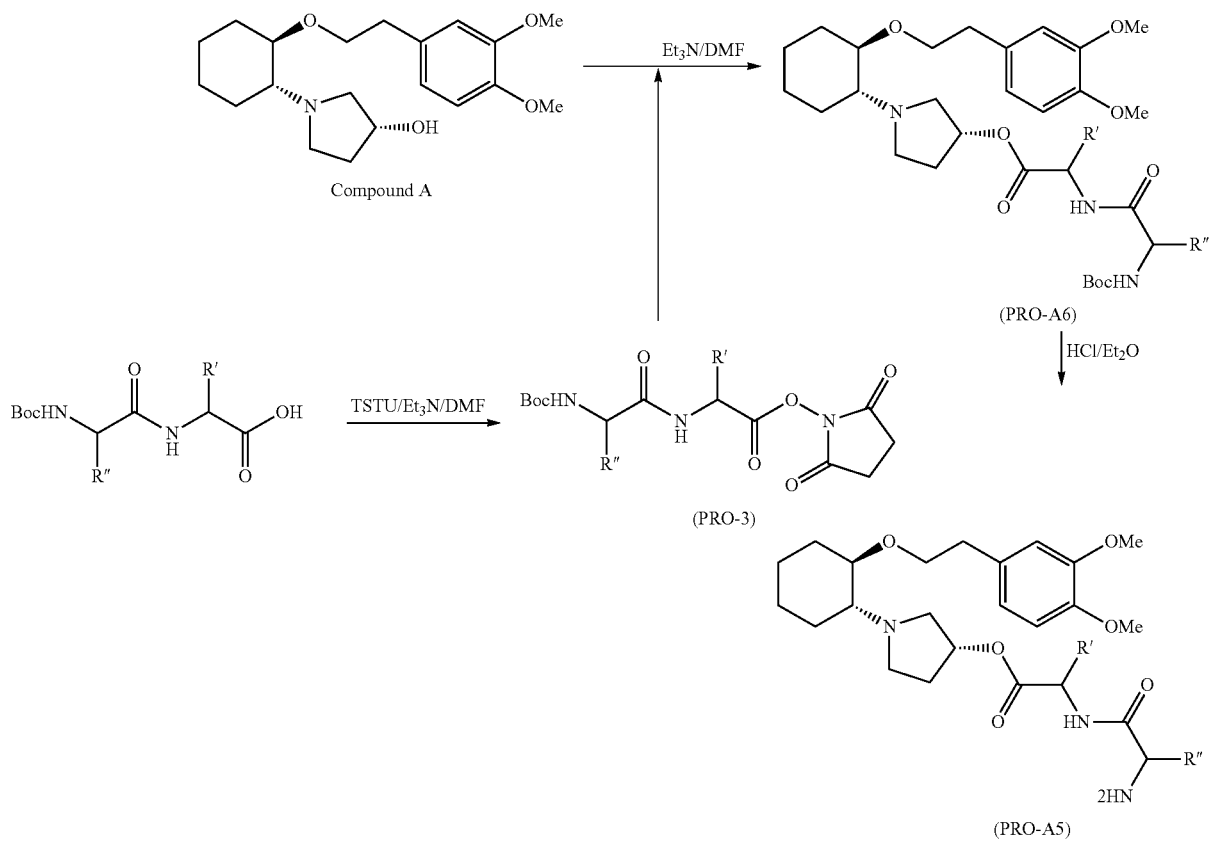

The process described above in Reaction Scheme 2A is generally applicable for any ion channel modulating compound comprising a hydroxyl functionality, although alternate processes may also be carried out. In general, synthesis of basic esters such as (PRO-A5) may be prepared by esterification of the free base of a hydroxyl containing ion channel modulating compound such as Compound A with an activated N-boc protected dipeptide such as (PRO-3). Activated dipeptides (PRO-3) are commercially available or may be prepared by reaction of the corresponding N-boc protected dipeptide with N,N,N',N'N-tetramethyl-O—(N-succinimidyl)uronium tetrafluoroborate (TSTU), according to the general procedure of Knorr et al. (see, Knorr, R.; Trzeciak, A.; Bannwarth, W.; Gillessen, D. *Tetrahedron Lett.* 1989, 30, 1927). In a typical experiment, the activated ester may be reacted with molar excesses of hydroxyl containing ion channel modulating compound, such as Compound A and triethylamine in a polar solvent such as DMF at ambient temperature for about 20 h. Standard work-up procedures well known in the art may be used in the isolation of the derivatives such as (PRO-A6). Cleavage of the carbamate protecting group in the presence of ethereal hydrogen chloride provides prodrugs such as formula (PRO-A5). In one variation, R' and R" of a prodrug such as that in formula (PRO-A5) are methyl groups.

Example 3

The following Reaction Scheme 3 illustrates the cleavage of an ester bond in an ester derivative prodrug (PRO-A7) to the respective Compound A and prodrug moiety:

REACTION SCHEME 3

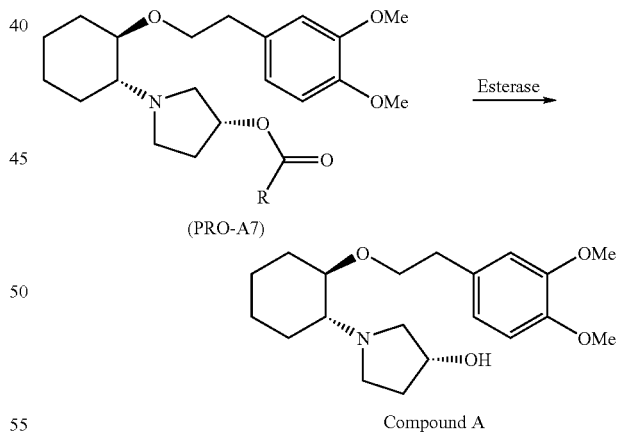

Reaction Scheme 3, which is generally applicable to prodrugs comprising an ester derivative of an ion channel modulating compound, shows a transformation process that may occur in the release of an ion channel modulating drug such as Compound A from an ester derivative prodrug such as that of formula (PRO-A7). In this instance, the transformation involves an enzymatic cleavage of the ester bond such as that in (PRO-A7).

Synthesis of ester derivative prodrugs such as (PRO-A7) may be carried out by standard procedures well known in the art as depicted in Reaction Scheme 3A, which is generally applicable to prodrugs comprising an ester derivative of an ion channel modulating compound. The process is generally applicable for any ion channel modulating compound comprising a hydroxyl functionality, although alternate processes may also be carried out.

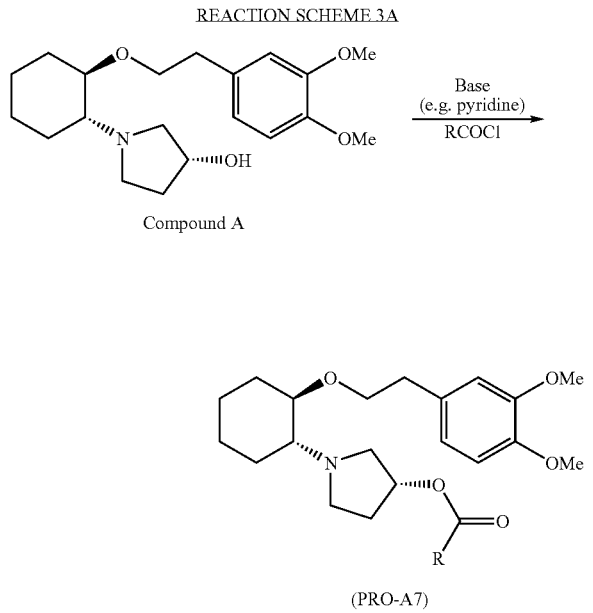

In Reaction Scheme 3A, any R group that provides an ester is suitable in this reaction (see, Bursi, R.; Grootenhuis, A.; van der Louw, J.; Verhagen, J.; de Gooyer, M.; Jacobs, P.; Leysen, D., *Steriod* 2003, 213-220.). More particular R groups include alkyl, substituted alkyl, alkenyl, substituted alkenyl, alkynyl, and substituted alkynyl groups as listed in the "prodrug moieties" section above. In one variation, the R group is an alkyl or a substituted alkyl group as listed in the "prodrug moieties" section above.

The following examples illustrate the use of prodrug moieties from the literature that have been reported to have good pharmacokinetics and safety profiles. Any prodrug moiety may be used in combination with an ion channel modulating compound to form a prodrug as described herein, including but not limited to those described in the "Prodrug Moieties" section above and in the examples below. The schemes below depicting ion channel modulating compounds are generally applicable to ion channel modulating compounds with the same or similar functional groups and the schemes below depicting prodrugs are generally applicable to prodrugs with the same or similar linkage bonds and/or prodrug moieties.

Example 4

The following Reaction Scheme 4 illustrates the cleavage of an ester bond in an ester derivative prodrug (PRO-A8) to the respective Compound A and prodrug moiety:

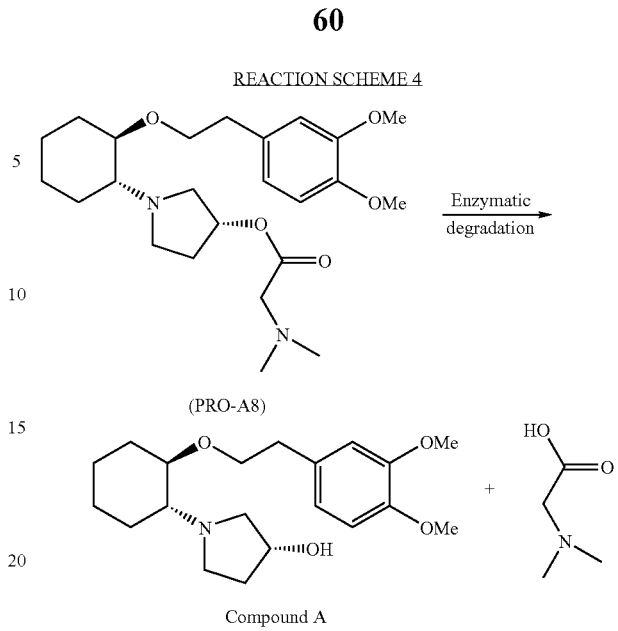

Reaction Scheme 4 shows a transformation process that may occur in the release of an ion channel modulating compound such as Compound A from the ester derivative prodrug such as that of formula (PRO-A8).

Synthesis of a dimethylglycine ester prodrug such as that of compound of formula (PRO-A8), i.e., (R)-1-((1R,2R)-2-(3,4-dimethoxyphenethoxy)cyclohexyl)pyrrolidin-3-yl-2-(dimethylamino)acetate, can be accomplished by standard literature procedures, as illustrated below in Reaction Scheme 4A. The process is generally applicable for any ion channel modulating compound comprising a hydroxyl functionality, although alternate processes may also be carried out.

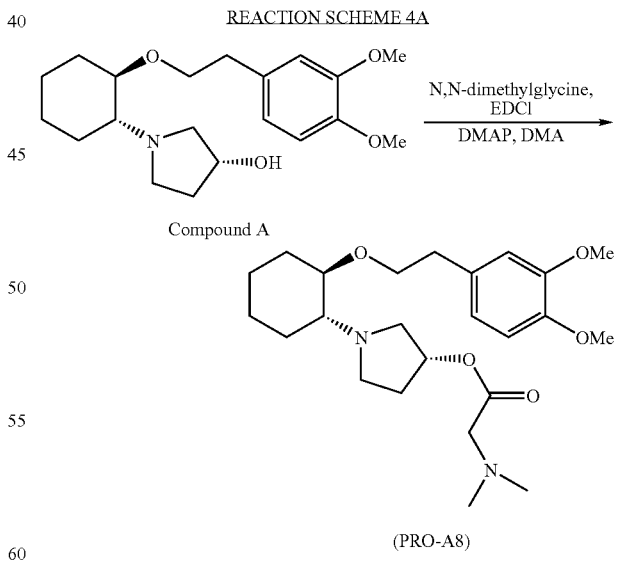

In general, reaction of Compound A with 4-(dimethylamino)pyridine, N,N-dimethylglycine and 1-[3(dimethylamino)propyl]-3-ethylcarbodiimide hydrochloride with N,N-dimethylacetamide may afford the compound (PRO-AB) (see, Gingrich, D. E.; Reddy, D. R.; Iqbal, M. A.; Singh, J.; Aimone, L. D.; Angeles, T. S.; Albom, M.; Yang, S.; Ator, M. A.; Meyer, S. L.; Robinson, C.; Ruggeri, B. A.; Dionne, C. A.; Vaught, J. L.; Mallamo, J. P.; Hudkins, R. L. *J. Med. Chem.* 2003, 46, 5375-5388).

Alternatively, the prodrug of formula (PRO-A8), i.e., (R)-1-((1R,2R)-2-(3,4-dimethoxyphenethoxy)cyclohexyl)pyrrolidin-3-yl-2-(dimethylamino)acetate, was prepared as follows, as illustrated below in Reaction Scheme 4B:

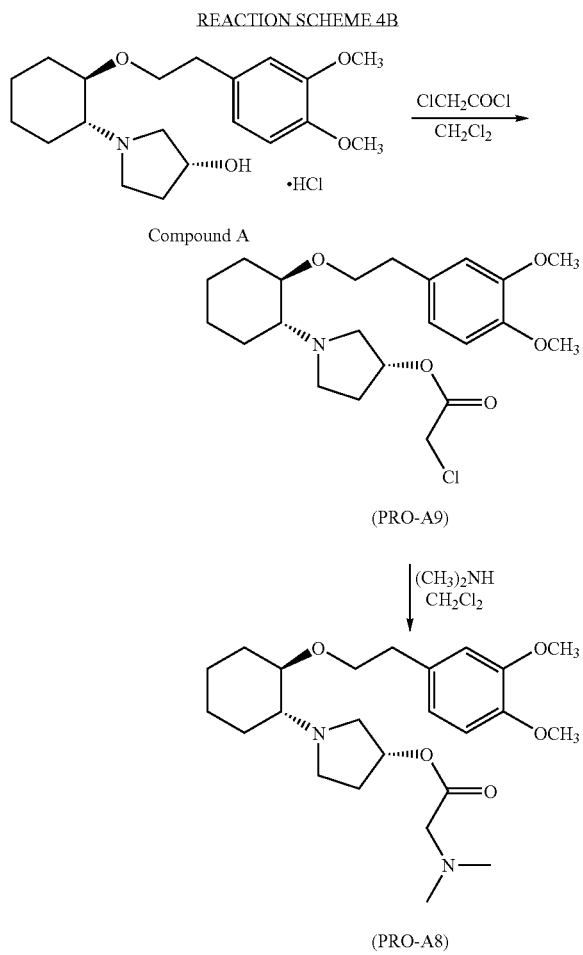

Specifically, a round bottom flask was charged with the hydrochloride salt of Compound A (2 g, 5.18 mmol). Air was evacuated and the system was flushed with nitrogen. Dry dichloromethane (26 mL) was added through the septum under nitrogen, and the solution was cooled to 0° C. To the cold solution was added chloroacetylchloride (1.76 g, 1.24 mL, 15.55 mmol) slowly. The mixture was then stirred at 0° C. for 7 h, and at ambient temperature overnight (17 h). The reaction was quenched by adding saturated aqueous sodium bicarbonate. The two layers were separated and the aqueous layer was extracted with dichloromethane (4×50 mL). The combined organic extracts were washed successively with water (3×50 mL) and brine (3×50 mL), dried over anhydrous $Na_2SO_4$, filtered and concentrated to afford the compound of formula (PRO-A9) (2.20 g, 99.5% yield) as a brown oil. MS (ES+, MeOH): [M+H]+ 426.0.

To a solution of the compound of formula (PRO-A9) (2.09 g, 4.91 mmol) in dichloromethane (10 mL) was added dimethylamine (2.0 M solution in THF, 1.10 g, 24.49 mmol, 12.24 mL). The solution was stirred at ambient temperature overnight, then diluted with water (50 mL) and extracted with dichloromethane (4×50 mL). The combined organic extracts were washed successively with saturated aqueous $NaHCO_3$ (3×50 mL), water (10×50 mL) and brine (2×75 mL), dried over anhydrous $Na_2SO_4$, filtered and concentrated to afford the compound of formula (PRO-A8) (1.53 g, 71.6% yield) as a light brown oil. $^1$H NMR (400 MHz, $CDCl_3$): δ 6.75 (m, 3H); 5.14 (m, 1H); 3.85 (s, 3H); 3.83 (s, 3H); 3.73 (m, 1H); 3.55 (m, 1H); 3.30 (br, s, 1H); 3.12 (s, 2H); 2.79 (br, m, 4H); 2.56 (br, s, 1H); 2.32 (m, 7H); 2.19-1.15 (m, 10H); $^{13}$C NMR (100 MHz, $CDCl_3$): δ 170.61 (C=O), 148.77, 147.47, 131.98, 120.79, 112.45, 111.24, 79.47, 74.14, 69.76, 63.86, 60.48, 56.89, 55.95, 55.86, 49.93, 45.63, 45.28, 35.51, 31.32, 28.90, 27.44, 23.34, 22.93; MS (ES+, MeOH): [M+H]+ 435.2, [M+2H]$^{2+}$ 218.1.

Alternatively, the prodrug of formula (PRO-A8a), i.e., (R)-1-((1R,2R)-2-(3,4-dimethoxyphenethoxy)cyclohexyl)pyrrolidin-3-yl-2-(2-aminoethyl)carbamate dihydrochloride, was prepared as follows, as illustrated below in Reaction Scheme 4C:

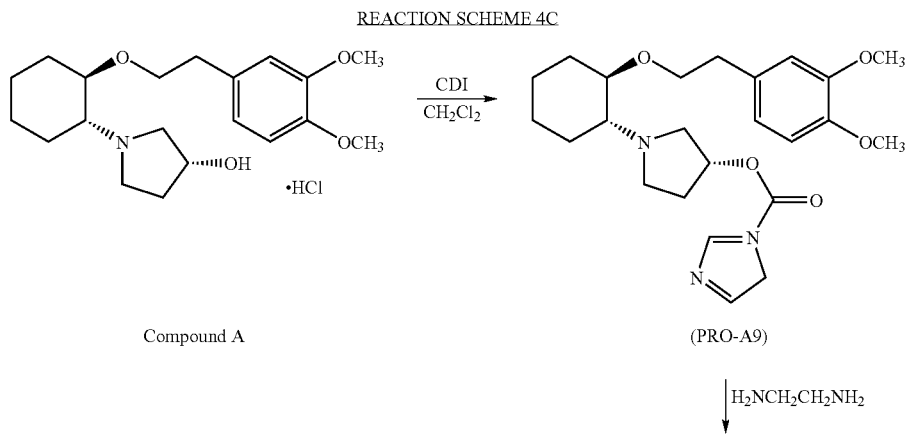

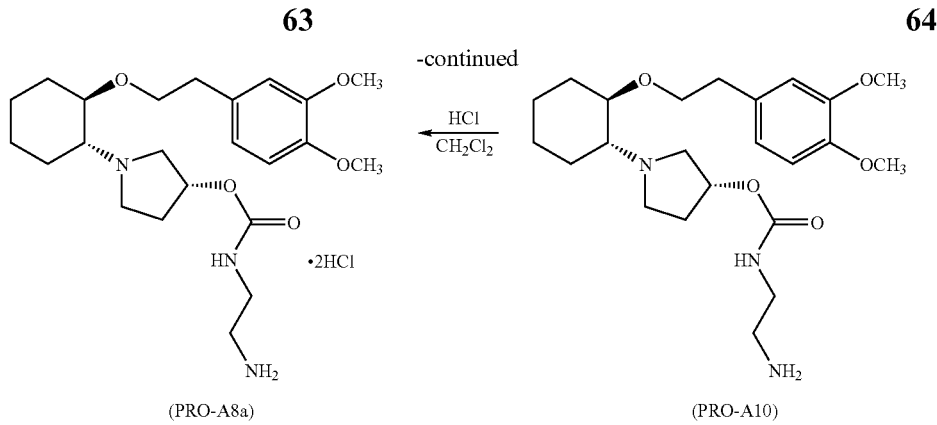

(PRO-A8a) ⇌ HCl/CH₂Cl₂ (PRO-A10)

Specifically, a round bottom flask was charged with hydrochloride salt of Compound A (2 g, 5.18 mmol). Air was evacuated and the system was flushed with nitrogen. Dry dichloromethane (22 mL) was added through the septum under nitrogen. To this solution was added a solution of carbonyldiimidazole (1.23 g, 7.75 mmol) in dichloromethane (5 mL) and the resultant mixture was stirred at ambient temperature overnight. Ethylenediamine (1.56 g, 1.73 mL, 25.91 mmol) was then added slowly and stirred for 24 h and then the reaction mixture was diluted with water (50 mL). The layers were separated and the aqueous phase was extracted with dichloromethane (4×50 mL). The combined organic extracts were washed successively with saturated aqueous NaHCO₃ (3×50 mL), water (10×50 mL) and brine (3×50 mL). The organic phase was dried over anhydrous Na₂SO₄, filtered and concentrated to afford the compound of formula (PRO-A10a) (1.81 g, 80% yield) as light brown oil. $^1$H NMR (400 MHz, CDCl₃) δ 6.75 (m, 3H); 5.16 (br, s, 1H); 5.05 (m, 1H); 3.85 (s, 3H); 3.83 (s, 3H); 3.73 (m, 1H); 3.55 (m, 1H); 3.29 (m, 1H); 3.19 (m, 2H); 2.79 (m, 6H); 2.50 (m, 1H); 2.32 (m, 1H); 2.09 (m, 1H); 2.02-1.55 (br, m, 8H); 1.40-1.12 (br, m, 4H); $^{13}$C NMR (100 MHz, CDCl₃) δ 156.64 (C=O), 148.65, 147.34, 131.91, 120.72, 112.33, 111.09, 79.73, 74.22, 69.68, 63.83, 57.19, 55.89, 55.84/55.80, 49.70, 43.47, 41.65, 36.44/36.32, 31.36, 28.99, 27.52/27.45, 23.42, 23.01; MS (ES⁺, MeOH): [M+H]⁺ 436.2, [M+2H]²⁺218.6.

To a solution of the compound of formula (PRO-A10) (1.81 g, 4.14 mmol) in dichloromethane (10 mL) was added HCl (2.0 M solution in ether, 14 mL) and stirred at ambient temperature for 15 min. The solution was then concentrated and the residue was dissolved in water. The aqueous solution was washed repeatedly with dichloromethane and the phases were separated. The aqueous phase was then concentrated and the residue was recrystallized (i-PrOH/Hexanes) to afford the compound of formula (PRO-A8a), i.e., (R)-1-((1R,2R)-2-(3,4-dimethoxyphenethoxy)cyclohexyl)pyrrolidin-3-yl-2-(2-aminoethyl)carbamate dihydrochloride, (1.28 g, 60.7% yield) as a light brown oil. MS (ES⁺, MeOH): [M+H]⁺ 436.2, [M+2H]²⁺ 218.6.

In a similar manner as described above, the following prodrugs of the invention may be prepared:
(S)-1-((1R,2R)-2-(3,4-dimethoxyphenethoxy)cyclohexyl) pyrrolidin-3-yl-2-(dimethylamino)acetate;
(R)-1-((1S,2S)-2-(3,4-dimethoxyphenethoxy)cyclohexyl) pyrrolidin-3-yl-2-(dimethylamino)acetate;
(S)-1-((1S,2S)-2-(3,4-dimethoxyphenethoxy)cyclohexyl) pyrrolidin-3-yl-2-(dimethylamino)acetate;
(R)-1-((1S,2R)-2-(3,4-dimethoxyphenethoxy)cyclohexyl) pyrrolidin-3-yl-2-(dimethylamino)acetate;
(S)-1-((1S,2R)-2-(3,4-dimethoxyphenethoxy)cyclohexyl) pyrrolidin-3-yl-2-(dimethylamino)acetate;
(R)-1-((1R,2S)-2-(3,4-dimethoxyphenethoxy)cyclohexyl) pyrrolidin-3-yl-2-(dimethylamino)acetate; and
(S)-1-((1R,2S)-2-(3,4-dimethoxyphenethoxy)cyclohexyl) pyrrolidin-3-yl-2-(dimethylamino)acetate.

Example 5

The following Reaction Scheme 5 illustrates a transformation process that may occur in the release of a compound such as a hydroxy derivative of Compound A from the ester derivative prodrug such as that of formula (PRO-A-Za1), i.e., 4-(2-((1R,2R)-2-((R)-3-hydroxypyrrolidin-1-yl)cyclohexyloxy) ethyl)-2-methoxyphenyl 2-(dimethylamino)acetate:

REACTION SCHEME 5

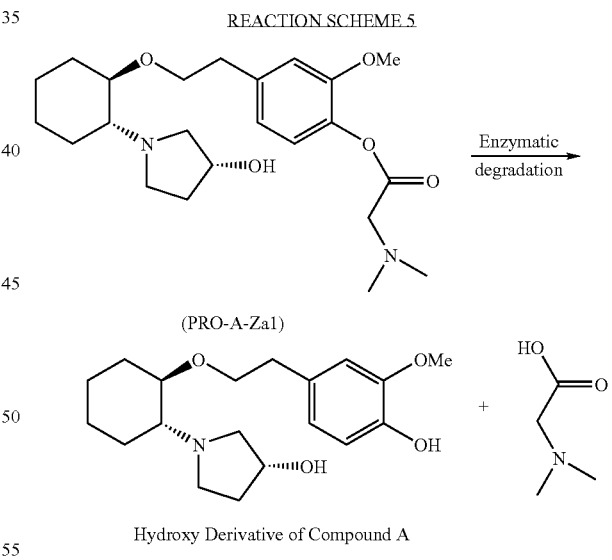

(PRO-A-Za1)

Hydroxy Derivative of Compound A

Reaction Scheme 5 shows, by way of example but not by way of limitation, a transformation process that may occur in the release of a compound such as a hydroxy derivative of Compound A from the ester derivative prodrug such as that of formula (PRO-A-Za1). In this instance, the transformation involves an enzymatic cleavage of the ester bond such as that in (PRO-A-Za1).

Synthesis of a dimethylglycine ester prodrug such as that of formula (PRO-A-Za1) above can be accomplished by standard literature procedures, as illustrated below in Reaction Scheme 5A:

REACTION SCHEME 5A

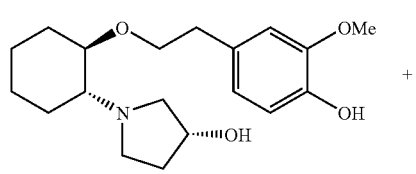

Hydroxy Derivative of Compound A

+

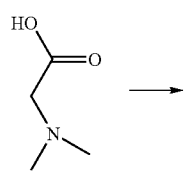

→

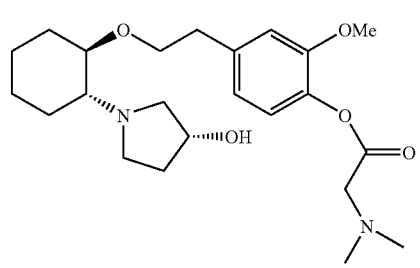

(PRO-A-Za1)

The process illustrated above in Reaction Scheme 5A is generally applicable for any compound comprising a hydroxyl functionality, although alternate processes may also be carried out. In a typical experiment, reaction of the hydroxy derivative of Compound A with 4-(dimethylamino) pyridine, N,N-dimethylglycine and 1-[3(dimethylamino) propyl]-3-ethylcarbodiimide hydrochloride with N,N-dimethylacetamide may afford the prodrug of formula (PRO-A-Za1), i.e., 4-(2-((1R,2R)-2-((R)-3-hydroxypyrrolidin-1-yl) cyclohexyloxy)ethyl)-2-methoxyphenyl 2-(dimethylamino) acetate (see, Gingrich, D. E.; Reddy, D. R.; Iqbal, M. A.; Singh, J.; Aimone, L. D.; Angeles, T. S.; Albom, M.; Yang, S.; Ator, M. A.; Meyer, S. L.; Robinson, C.; Ruggeri, B. A.; Dionne, C. A.; Vaught, J. L.; Mallamo, J. P.; Hudkins, R. L. *J. Med. Chem.* 2003, 46, 5375-5388).

Example 6

The following Reaction Scheme 6 illustrates a shows a transformation process that may occur in the release of an ion channel modulating compound such as Compound A from an ester derivative prodrug such as that of formula (PRO-A11), i.e., 2-(7-((R)-1-((1R,2R)-2-(3,4-dimethoxyphenethoxy)cyclohexyl)pyrrolidin-3-yloxy)-N-methyl-7-oxoheptanamido) ethanesulfonic acid):

REACTION SCHEME 6

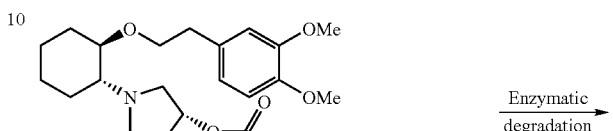

(PRO-A11)

Enzymatic degradation →

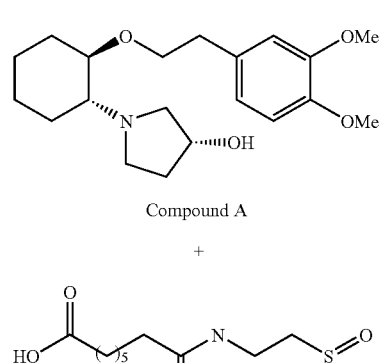

Compound A

+

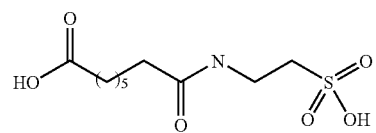

In this instance, the transformation illustrated above in Reaction Scheme 6 involves an enzymatic cleavage of the ester bond in the prodrug of formula (PRO-A11), i.e., 2-(7-((R)-1-((1R,2R)-2-(3,4-dimethoxyphenethoxy)cyclohexyl) pyrrolidin-3-yloxy)-N-methyl-7-oxoheptanamido)ethanesulfonic acid). The suleptanate group in the prodrug of formula (PRO-A11) is used as a prodrug in Pharmacia Corp's asthma drug, Promedrol (Paggiaro, P.; *Current Opinion in investigational Drugs.* 2000, 1, 97-103). This ester may be stable in saline solution and may have good pharmacokinetics and safety profile. The prodrug of formula (PRO-A11) may be prepared by known procedures, e.g., it can be prepared either from Compound A via condensation with hemisuberate or by condensation of Compound A with protected suleptanic acid (*Drug Future.* 1997, 22, 833-840. The Synthesis of Methylprednisolone Suleptenate and a Review of its Biological Data). Enzymatic cleavage of this group will release the ion channel modulating agent, Compound A.

In a similar manner, the following prodrugs of ion channel modulating compounds may be prepared:

2-(7-((S)-1-((1R,2R)-2-(3,4-dimethoxyphenethoxy)cyclohexyl)pyrrolidin-3-yloxy)-N-methyl-7-oxoheptanamido)ethanesulfonic acid;

2-(7-((R)-1-((1S,2S)-2-(3,4-dimethoxyphenethoxy)cyclohexyl)pyrrolidin-3-yloxy)-N-methyl-7-oxoheptanamido)ethanesulfonic acid;

2-(7-((S)-1-((1S,2S)-2-(3,4-dimethoxyphenethoxy)cyclohexyl)pyrrolidin-3-yloxy)-N-methyl-7-oxoheptanamido)ethanesulfonic acid;

2-(7-((R)-1-((1S,2R)-2-(3,4-dimethoxyphenethoxy)cyclohexyl)pyrrolidin-3-yloxy)-N-methyl-7-oxoheptanamido)ethanesulfonic acid;

2-(7-((S)-1-((1S,2R)-2-(3,4-dimethoxyphenethoxy)cyclohexyl)pyrrolidin-3-yloxy)-N-methyl-7-oxoheptanamido)ethanesulfonic acid;

2-(7-((R)-1-((1R,2S)-2-(3,4-dimethoxyphenethoxy)cyclohexyl)pyrrolidin-3-yloxy)-N-methyl-7-oxoheptanamido)ethanesulfonic acid; and 2-(7-((S)-1-((1R,2S)-2-(3,4-dimethoxyphenethoxy)cyclohexyl)pyrrolidin-3-yloxy)-N-methyl-7-oxoheptanamido)ethanesulfonic acid.

Example 7

A strategy which may be employed in preparing the prodrugs of the invention is to utilize a water-soluble prodrug moiety with a self cleavable linker, such as seen with the water solubilizing prodrug moiety with an ionized amino functionality such as seen in the following Reaction Scheme 7:

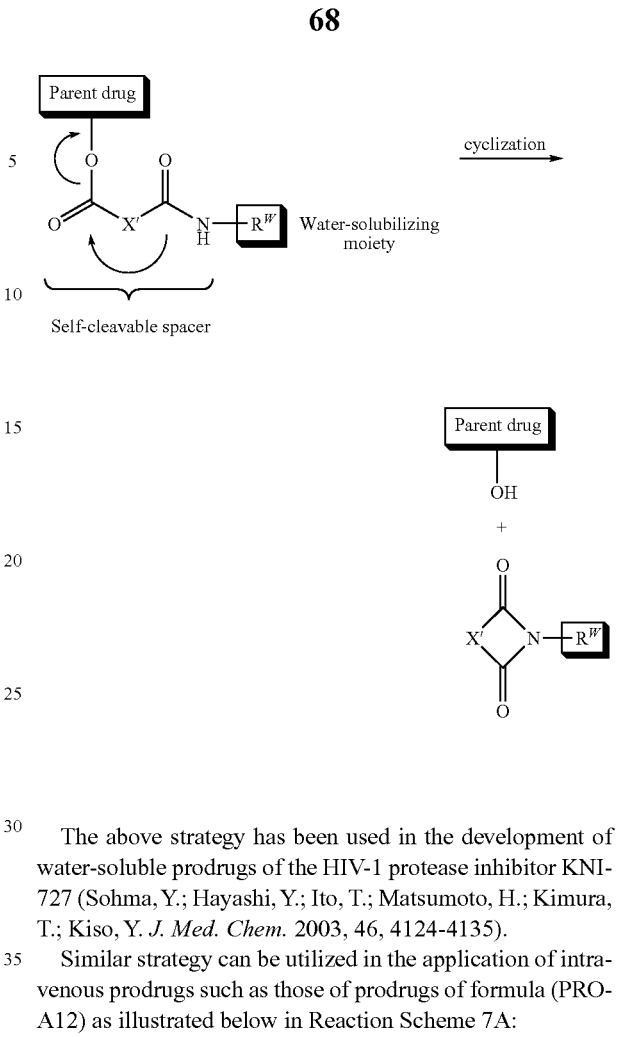

The above strategy has been used in the development of water-soluble prodrugs of the HIV-1 protease inhibitor KNI-727 (Sohma, Y.; Hayashi, Y.; Ito, T.; Matsumoto, H.; Kimura, T.; Kiso, Y. *J. Med. Chem.* 2003, 46, 4124-4135).

Similar strategy can be utilized in the application of intravenous prodrugs such as those of prodrugs of formula (PRO-A12) as illustrated below in Reaction Scheme 7A:

REACTION SCHEME 7A

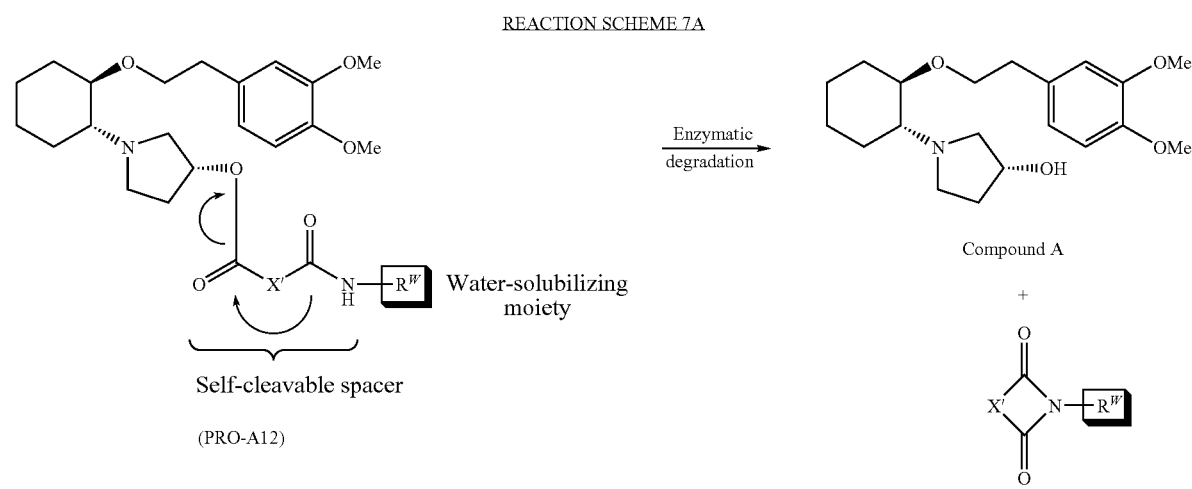

The ion channel modulating compound may be released by an intramolecular cyclization-elimination reaction such as the one depicted in Reaction Scheme 7A. The water solubilizing moiety is generally a moiety comprising one or more, typically 1 to 6, 2 to 6, 3 to 6, or 1, 2, 3, 4, 5 or 6 or more hydroxyl groups.

Example 8

The formation of prodrugs of the invention, such as the prodrugs of formula (PRO-A13) as illustrated below in Reaction Scheme 8, may be performed by esterification of the free base of a hydroxyl containing ion channel modulating compound such as Compound A with an activated peptide such as compound of formula (PRO-4):

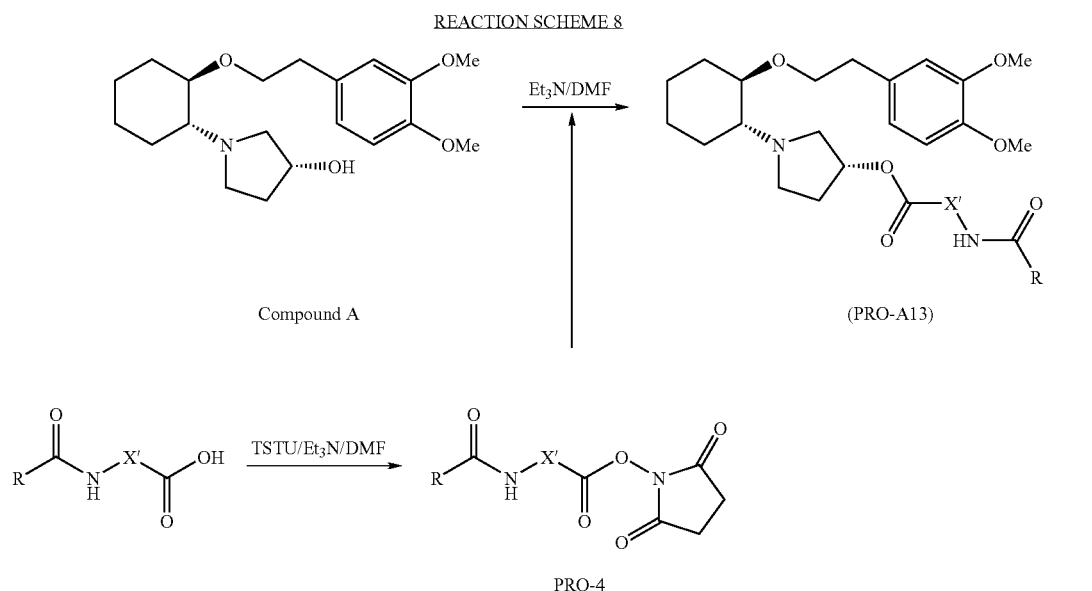

Activated peptides are commercially available or may be prepared by reaction of the corresponding peptide with N,N,N',N'-tetramethyl-O—(N-succinimidyl)uronium tetrafluoroborate (TSTU), according to the general procedure of Knorr et al. (see, Knorr, R.; Trzeciak, A.; Bannwarth, W.; Gillessen, D. *Tetrahedron Lett.* 1989, 30, 1927). In a typical experiment, an activated ester may be reacted with a molar excess of a hydroxyl containing ion channel modulating compound such as Compound A and triethylamine in a polar solvent such as DMF at ambient temperature for 20 h. Standard work-up procedures well known in the art may permit the isolation of prodrugs of formula (PRO-A13).

Example 9

The following Reaction Scheme 9 illustrates transformation processes that may occur in the release of an ion channel modulating compound such as Compound A from the ester derivative prodrug such as that of formula (PRO-A14). In this instance, the transformation involves an enzymatic cleavage of the ester bond in the prodrug of formula (PRO-A14):

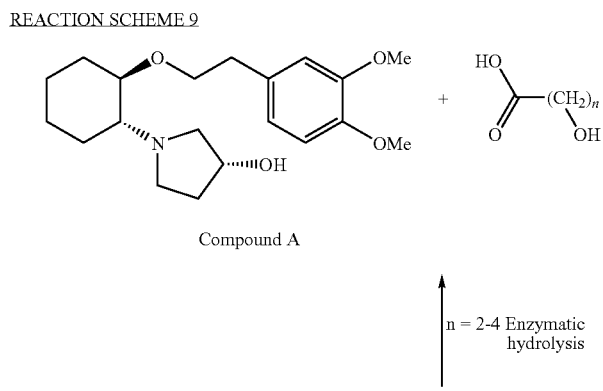

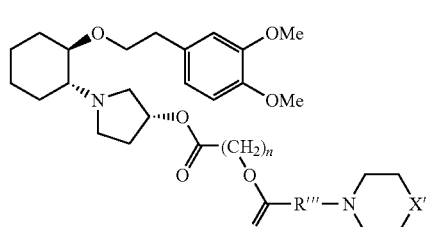

(PRO-A14)

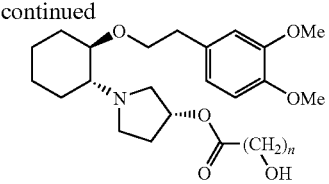

-continued

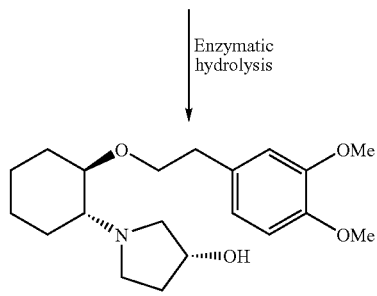

Compound A

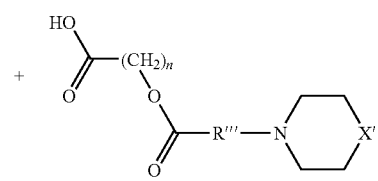

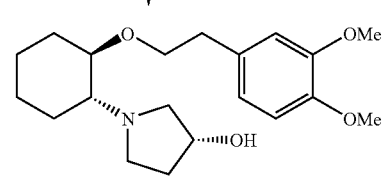

Compound A

+

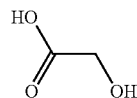

In the above Reaction Scheme 9, the ion channel modulating compound such as Compound A may be released by spontaneous or enzymatic hydrolysis of the ester linkage depending on the nature of this group such as the one depicted in prodrug of formula (PRO-A14) or the prodrug of formula (PRO-A15). This strategy has been demonstrated as a promising method of obtaining a prodrug of the nonsteroidal anti-inflammatory drug (see, NSAID, Rautio, J.; Nevalainen, T.; Taipale, H.; Vepsäläinen.; Gynther, J.; Laine, K.; Järvinen, T. *J. Med. Chem.* 2000, 43, 1489-1494).

Synthesis of the prodrug of formula (PRO-A14) involves the formation of a hydroxyl ester derivative such as the prodrug of formula (PRO-A15) using standard ester bond formation procedures well known in the art, as illustrated below in Reaction Scheme 9A:

REACTION SCHEME 9A

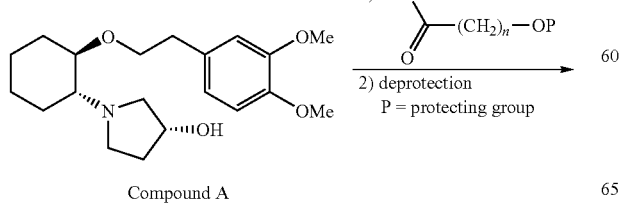

-continued

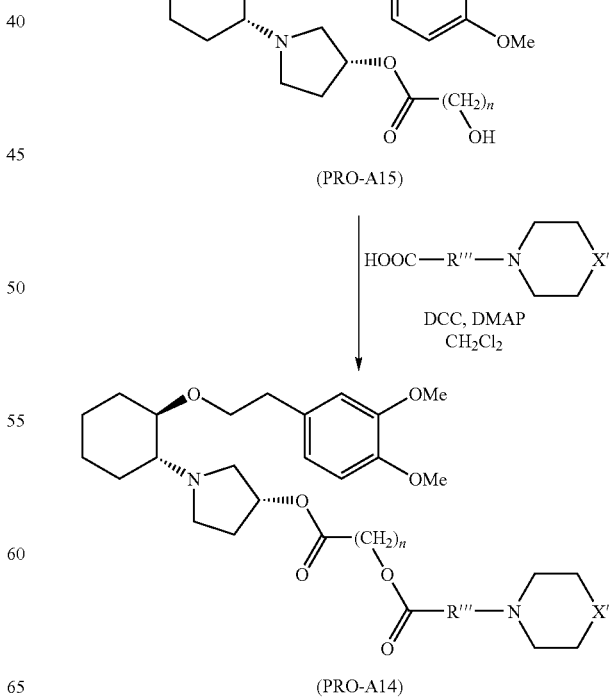

As illustrated above in Reaction Scheme 9A, the morpholinyl (X'=O) and methylpiperazinylacyloxyalkyl (X'=N) prodrugs of formula (PRO-A14) may be prepared by coupling the corresponding hydroxyl alkyl ester of the prodrug of formula (PRO-A15) with the morpholinyl- and (4-methyl-1-piperazinyl)acyl chloride in the presence of dicyclohexylcarbodiimide (DCC) and 4-(dimethylamino)-pyridine (DMAP) in dry dichloromethane.

Example 10

Reaction Scheme 10 shows transformation processes that may occur in the release of an ion channel modulating compound such as Compound A from a saccharide prodrug such as that of formula (PRO-A16), i.e., 6-(2-amino-4-(((2-((((R)-1-((1R,2R)-2-(3,4-dimethoxyphenethoxy)cyclohexyl)pyrrolidin-3-yloxy)carbonyl)(methyl)amino)ethyl)(methyl)carbamoyloxy)methyl)phenoxy)-3,4,5-trihydroxy-tetrahydro-2H-pyran-2-carboxylic acid) involving an enzymatic cleavage of the bond in the prodrug of formula (PRO-A16) where Compound A' is the radical of the following formula:

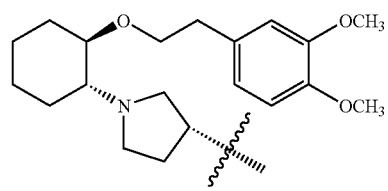

REACTION SCHEME 10

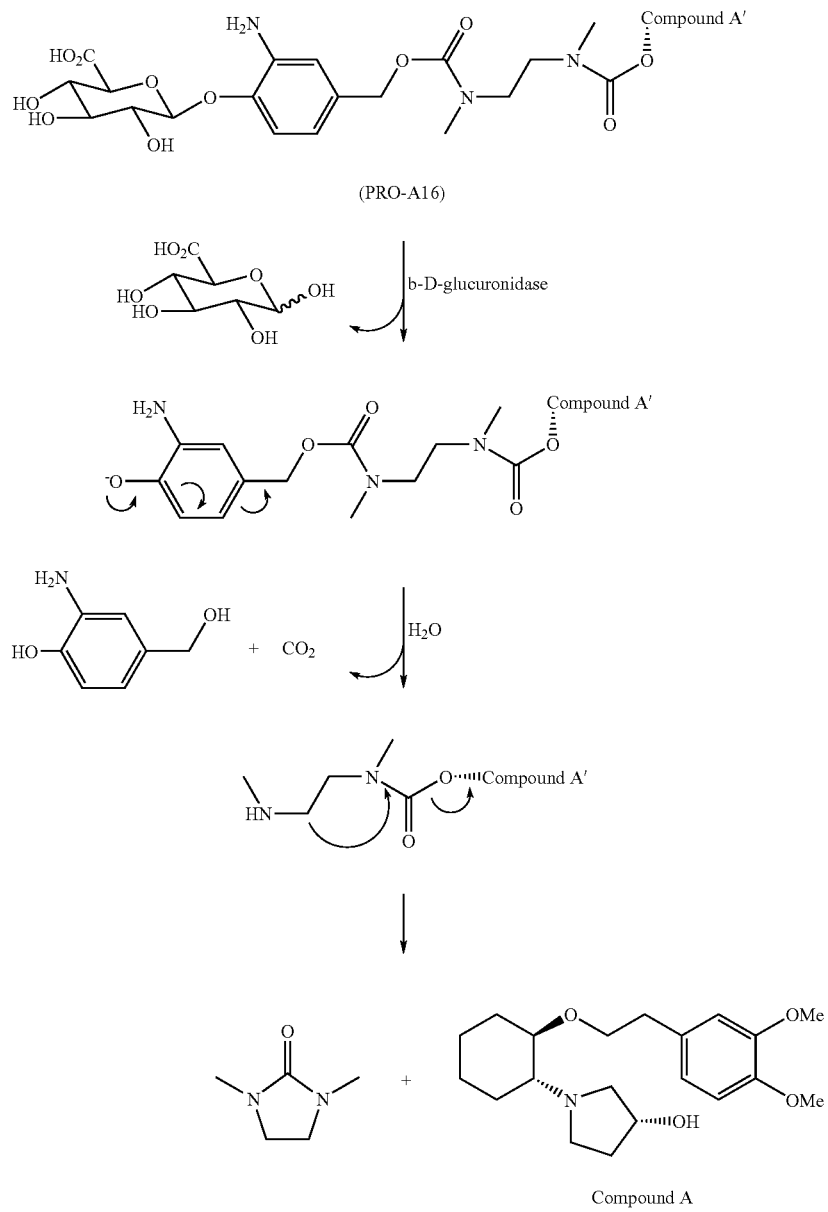

In this example, which is generally applicable to like compounds, the release of the ion channel modulating drug from the prodrug of formula (PRO-A16) may involve enzymatic hydrolysis of the prodrug by β-D-glucuronidase as shown above in Reaction Scheme 10 (see, Bouvier, E.; Thirot, S.; Schmidt, F.; Monneret, C. *Org. Biol. Chem.* 2003, 1, 3343-3352).

The synthesis of the prodrug of formula (PRO-A16) is illustrated below in Reaction Scheme 10A:

As illustrated above in Reaction Scheme 10A, synthesis of a prodrug of formula (PRO-A16), i.e., 6-(2-amino-4-(((2-((((R)-1-((1R,2R)-2-(3,4-dimethoxyphenethoxy)cyclohexyl)pyrrolidin-3-yloxy)carbonyl)(methyl)amino)ethyl)(methyl)carbamoyloxy)methyl)phenoxy)-3,4,5-trihydroxy-tetrahydro-2H-pyran-2-carboxylic acid, may involve the coupling of a compound such as (PRO-5) with an ion channel modulating compound such as Compound A under catalytic basic conditions in dichloromethane to give compound of

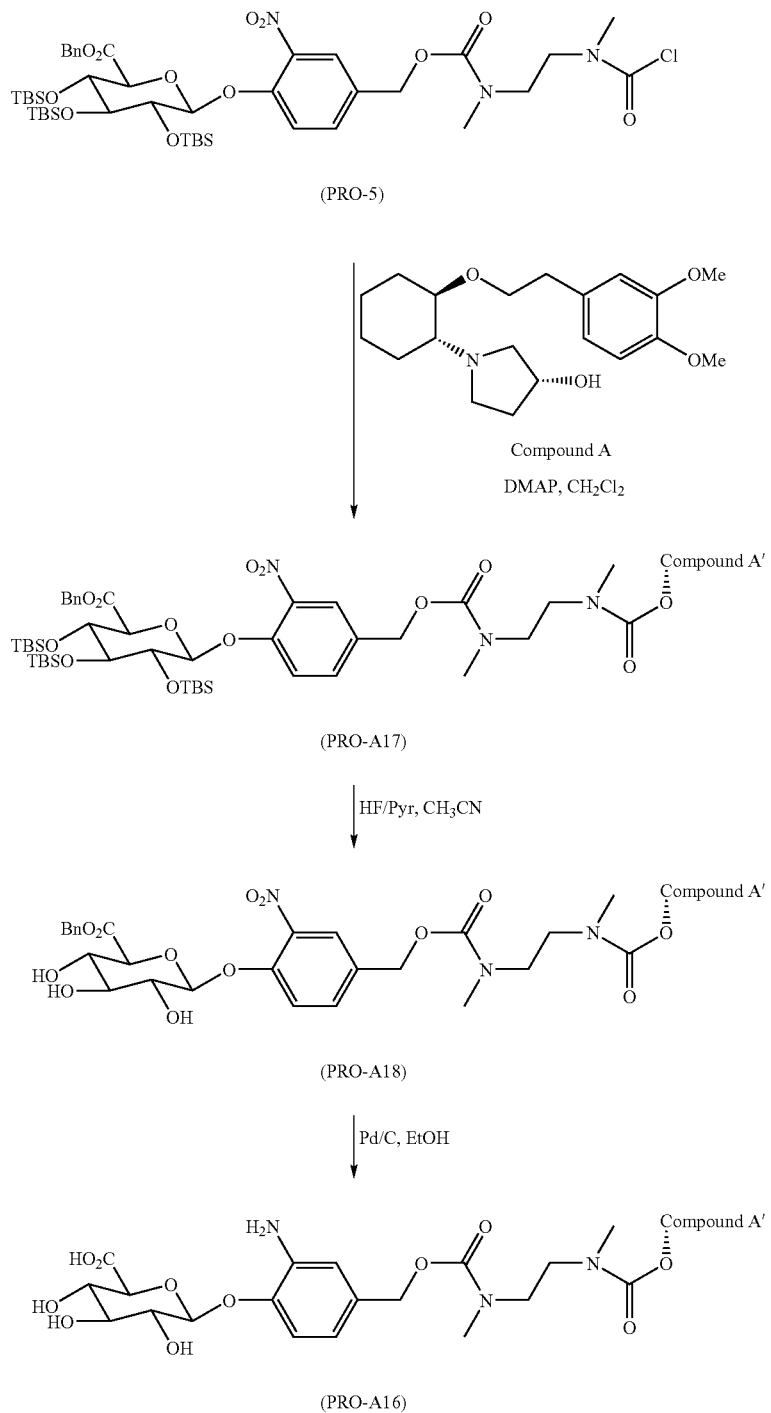

formula (PRO-A17). Removal of the TBS protecting groups with hydrogen fluoride in pyridine followed by palladium may catalyze hydrogenation of the compound of formula (PRO-A17) to give the prodrug of formula (PRO-A16) (see, Rautio, J.; Nevalainen, T.; Taipale, H.; Vepsäläinen.; Gynther, J.; Laine, K.; Järvinen, T. *J. Med. Chem.* 2000, 43, 1489-1494). Compound of formula (PRO-5) may be synthesized according to the method of Florent et al. (Florent, J-C.; Dong, X.; Gaudel, G.; Mitaku, S.; Monneret, C.; Gesson, J-P.; Jacquesy, J-C.; Mondon, M.; Renoux, B.; Andrianomenjanahary, S.; Michel, S.; Koch, M.; Tillequin, F.; Gerken, M.; Czech, J.; Straub, R.; Bosslet, K. *J. Med. Chem.* 1998, 41, 3572-3581).

In a similar manner, the following prodrugs of ion channel modulating compounds may be prepared:

6-(2-amino-4-(((2-((((S)-1-((1R,2R)-2-(3,4-dimethoxyphenethoxy)cyclohexyl)pyrrolidin-3-yloxy)carbonyl)(methyl)amino)ethyl)(methyl)carbamoyloxy)methyl)phenoxy)-3,4,5-trihydroxy-tetrahydro-2H-pyran-2-carboxylic acid;

6-(2-amino-4-(((2-((((R)-1-((1S,2S)-2-(3,4-dimethoxyphenethoxy)cyclohexyl)pyrrolidin-3-yloxy)carbonyl)(methyl)amino)ethyl)(methyl)carbamoyloxy)methyl)phenoxy)-3,4,5-trihydroxy-tetrahydro-2H-pyran-2-carboxylic acid;

6-(2-amino-4-(((2-((((S)-1-((1S,2S)-2-(3,4-dimethoxyphenethoxy)cyclohexyl)pyrrolidin-3-yloxy)carbonyl)(methyl)amino)ethyl)(methyl)carbamoyloxy)methyl)phenoxy)-3,4,5-trihydroxy-tetrahydro-2H-pyran-2-carboxylic acid 6-(2-amino-4-(((2-((((R)-1-((1S,2R)-2-(3,4-dimethoxyphenethoxy)cyclohexyl)pyrrolidin-3-yloxy)carbonyl)(methyl)amino)ethyl)(methyl)carbamoyloxy)methyl)phenoxy)-3,4,5-trihydroxy-tetrahydro-2H-pyran-2-carboxylic acid;

6-(2-amino-4-(((2-((((S)-1-((1S,2R)-2-(3,4-dimethoxyphenethoxy)cyclohexyl)pyrrolidin-3-yloxy)carbonyl)(methyl)amino)ethyl)(methyl)carbamoyloxy)methyl)phenoxy)-3,4,5-trihydroxy-tetrahydro-2H-pyran-2-carboxylic acid;

6-(2-amino-4-(((2-((((R)-1-((1R,2S)-2-(3,4-dimethoxyphenethoxy)cyclohexyl)pyrrolidin-3-yloxy)carbonyl)(methyl)amino)ethyl)(methyl)carbamoyloxy)methyl)phenoxy)-3,4,5-trihydroxy-tetrahydro-2H-pyran-2-carboxylic acid; and 6-(2-amino-4-(((2-((((S)-1-((1R,2S)-2-(3,4-dimethoxyphenethoxy)cyclohexyl)pyrrolidin-3-yloxy)carbonyl)(methyl)amino)ethyl)(methyl)carbamoyloxy)methyl)phenoxy)-3,4,5-trihydroxy-tetrahydro-2H-pyran-2-carboxylic acid.

Example 11

Another prodrug moiety that may be used in a prodrug of the invention is a phosphate ester (see, Schultz, C.; *Bioorg. Med. Chem.* 2003, 11, 885-898. Egron, D.; Imbach, J-L.; Gosselin, G.; Aubertin, A-M.; Périgaud, C.; *J. Med. Chem.* 2003, 46, 4564-4571. ProQuest Pharmaceutical, INC. PHOS™ Prodrugs of Alcohols and Phenols. 1201 Wakarusa Drive, E2 Lawrence, Kans. 66049). This functional group is widely used for drugs containing hydroxyl (—OH) functionalities or amino functionalities, such as hydroxyl or amino containing ion channel modulating compounds such as Compound A. In one aspect, a phosphate ester derivative prodrug such as that of formula (PRO-A19), i.e., (1S,3R)-1-((1R,2R)-2-(3,4-dimethoxyphenethoxy)cyclohexyl)-3-hydroxy-1-(phosphonooxymethyl)pyrrolidinium) is provided. In another aspect, a phosphate ester derivative prodrug such as that of formula (PRO-A20), i.e., ((R)-1-((1R,2R)-2-(3,4-dimethoxyphenethoxy)cyclohexyl)pyrrolidin-3-yloxy)methyl dihydrogen phosphate) is provided. Structures of these two examples are depicted below in FIG. 5. Liberation of the parent ion channel modulating compound, Compound A, will generally occur upon enzymatic degradation of the phosphate ester linkage.

FIG. 5: Phosphate Ester Prodrugs

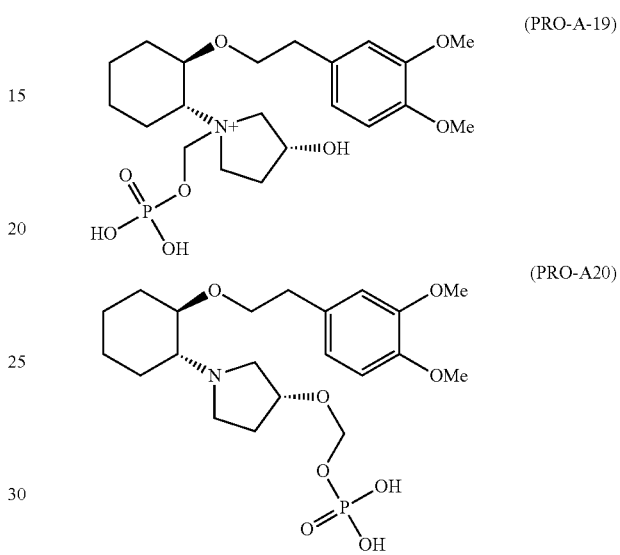

In a similar manner, the following prodrugs of ion channel modulating compounds may be prepared:

(1S,3S)-1-((1R,2R)-2-(3,4-dimethoxyphenethoxy)cyclohexyl)-3-hydroxy-1-(phosphonooxymethyl)pyrrolidinium;

(1R,3R)-1-((1S,2S)-2-(3,4-dimethoxyphenethoxy)cyclohexyl)-3-hydroxy-1-(phosphonooxymethyl)pyrrolidinium;

(1R,3S)-1-((1S,2S)-2-(3,4-dimethoxyphenethoxy)cyclohexyl)-3-hydroxy-1-(phosphonooxymethyl)pyrrolidinium;

(1R,3R)-1-((1S,2R)-2-(3,4-dimethoxyphenethoxy)cyclohexyl)-3-hydroxy-1-(phosphonooxymethyl)pyrrolidinium;

(1R,3S)-1-((1S,2R)-2-(3,4-dimethoxyphenethoxy)cyclohexyl)-3-hydroxy-1-(phosphonooxymethyl)pyrrolidinium;

(1S,3R)-1-((1R,2S)-2-(3,4-dimethoxyphenethoxy)cyclohexyl)-3-hydroxy-1-(phosphonooxymethyl)pyrrolidinium;

(1S,3S)-1-((1R,2S)-2-(3,4-dimethoxyphenethoxy)cyclohexyl)-3-hydroxy-1-(phosphonooxymethyl)pyrrolidinium;

((S)-1-((1R,2R)-2-(3,4-dimethoxyphenethoxy)cyclohexyl)pyrrolidin-3-yloxy)methyl dihydrogen phosphate ((R)-1-((1S,2S)-2-(3,4-dimethoxyphenethoxy)cyclohexyl)pyrrolidin-3-yloxy)methyl dihydrogen phosphate;

((S)-1-((1S,2S)-2-(3,4-dimethoxyphenethoxy)cyclohexyl)pyrrolidin-3-yloxy)methyl dihydrogen phosphate;

((R)-1-((1S,2R)-2-(3,4-dimethoxyphenethoxy)cyclohexyl)pyrrolidin-3-yloxy)methyl dihydrogen phosphate;

((S)-1-((1S,2R)-2-(3,4-dimethoxyphenethoxy)cyclohexyl)pyrrolidin-3-yloxy)methyl dihydrogen phosphate;

((R)-1-((1R,2S)-2-(3,4-dimethoxyphenethoxy)cyclohexyl) pyrrolidin-3-yloxy)methyl dihydrogen phosphate; and
((S)-1-((1R,2S)-2-(3,4-dimethoxyphenethoxy)cyclohexyl) pyrrolidin-3-yloxy)methyl dihydrogen phosphate.

Biological Example 1

Assessment of Antiarrhythmic Efficacy

Antiarrhythmic efficacy may be assessed by investigating the effect of a compound of the invention on the incidence of cardiac arrhythmias in anesthetized rats subjected to coronary artery occlusion. Rats weighing 200-300 gms are subjected to preparative surgery and assigned to groups in a random block design. In each case, the animal is anesthetized with pentobarbital during surgical preparation. The left carotid artery is cannulated for measurement of mean arterial blood pressure and withdrawal of blood samples. The left jugular vein is also cannulated for injection of drugs. The thoracic cavity is opened and a polyethylene occluder loosely placed around the left anterior descending coronary artery. The thoracic cavity is then closed. An ECG is recorded by insertion of electrodes placed along the anatomical axis of the heart. In a random and double-blind manner, an infusion of vehicle or the compound to be tested is given about 15 min post-surgery. After 5 minutes infusion, the occluder is pulled out so as to produce a coronary artery occlusion. ECG, arrhythmias, blood pressure, heart rate and mortality are monitored for 15 minutes after occlusion. Arrhythmias are recorded as ventricular tachycardia (VT) and ventricular fibrillation (VF) and scored according to Curtis, M. J. and Walker, M. J. A., *Cardiovasc. Res.* 22: 656 (1988).

Rats are excluded from the study if they did not exhibit pre-occlusion serum potassium concentrations within the range of 2.9-3.9 mM. Occlusion is associated with increases in R-wave height and "S-T" segment elevation; and an occluded zone (measured after death by cardiogreen dye perfusion) in the range of 25%-50% of total left-ventricular weight.

Results of the test compounds may be expressed as values of a given infusion rate in micromol/kg/min. ($ED_{50}AA$) which will reduce the arrhythmia score in treated animals to 50% of that shown by animals treated only with the vehicle in which the test compound(s) is dissolved.

Biological Example 2

Measurement of Cardiovascular and Behavioral Effects

Preparative surgery is performed in Sprague Dawley rats weighing 200-300 gm and anaesthetized with 65 mg/kg (i.p.) pentobarbital. The femoral artery and vein are cannulated using polyethylene (PE)-10 tubing. Prior to surgery, this PE-10 tubing had been annealed to a wider gauge (PE-50) tubing for externalization. The cannulated PE-10/PE-50 tubing is passed through a trocar and exteriorised together with three (lead II) limb ECG leads (see below). The trocar is threaded under the skin of the back and out through a small incision at the mid-scapular region. A ground ECG electrode is inserted subcutaneously using a 20 gauge needle with the lead wire threaded through it. To place the other ECG electrodes, a small incision is made in the anterior chest region over the heart and ECG leads are inserted into the subcutaneous muscle layer in the region of the heart using a 20 gauge needle. Other ECG leads are inserted into the subcutaneous muscle layer in the region near the base of the neck and shoulder (right side). The animal is returned to a clean recovery-cage with free access to food and water. The treatment and observational period for each animal commenced after a 24-hour recovery period.

A 15 min observational period is recorded followed by the intravenous infusion regime of the test compound at an initial dose of 2.0 µmol/kg/min (at 1 ml/hr). This rate is doubled every 5 minutes until one of the following effects is observed:
  a) partial or complete convulsions
  b) severe arrhythmias
  c) bradycardia below 120 beats/min
  d) hypotension below 50 mmHg
  e) the dose exceeds 32 times the initial starting dose (i.e. 64 µmol/kg/min).

Blood pressure (BP), heart rate (HR) and ECG variables are continuously recorded while behavioral responses are also monitored and the total accumulative drug dose and drug infusion rate at which the response (such as convulsion, piloerection, ataxia, restlessness, compulsive chewing, lipsmacking, wet dog shake etc.) occurred are recorded.

Estimates of plasma concentrations of the test compound are determined by removing a 0.5 mL blood sample at the end of the experiment. Blood samples are centrifuged for 5 min at 4600×g and the plasma decanted. Brain tissue samples are also extracted and kept frozen (−20° C.) along with the plasma samples for chemical analysis.

Electrocardiograph (ECG) parameters: PR, QRS, $QT_1$ (peak of T-wave), $QT_2$ (midpoint of T-wave deflection) and hemodynamic parameters: BP and HR are analyzed using the automated analysis function in LabView (National Instruments) with a customized autoanalysis software (Nortran Pharmaceuticals). The infused dose producing 25% from control ($D_{25}$) for all recorded ECG variables is determined.

Results of the tests can be expressed as $D_{25}$ (micromol/kg) which are the doses required to produce a 25% increase in the ECG parameter measured. The increases in P-R interval and QRS interval indicate cardiac sodium channel blockade while the increase in Q-T interval indicates cardiac potassium channel blockade.

Biological Example 3

Electrophysiological Test (In Vivo)

Male Sprague-Dawley rats weighing between 250-350 g are used. They are randomly selected from a single group and anesthetized with pentobarbital (65 mg/kg, ip.) with additional anesthetic given if necessary.

The trachea is cannulated and the rat is artificially ventilated at a stroke volume of 10 mL/kg, 60 strokes/minute. The right external jugular vein and the left carotid artery are cannulated for intravenous injections of compounds and blood pressure (BP) recording, respectively.

Needle electrodes are subcutaneously inserted along the suspected anatomical axis (right atrium to apex) of the heart for ECG measurement. The superior electrode is placed at the level of the right clavicle about 0.5 cm from the midline, while the inferior electrode is placed on the left side of the thorax, 0.5 cm from the midline and at the level of the ninth rib.

Two Teflon-coated silver electrodes are inserted through the chest wall using 27G needles as guides and implanted in the epicardium of left ventricle (4-5 mm apart). Square pulse stimulation is provided by a stimulator controlled by a computer. In-house programmed software is used to determine the following: threshold current (iT) for induction of extra systoles, maximum following frequency (MFF), effective refractory period (ERP) and ventricular flutter threshold (VTt).

Briefly, iT is measured as the minimal current (in μA) of a square wave stimulus required to capture and pace the heart at a frequency of 7.5 Hz and a pulse width of 0.5 msec; ERP is the minimum delay (in msec) for a second stimulus required to cause an extra systole with the heart entrained at a frequency of 7.5 Hz (1.5×iT and 0.2 msec pulse width), MFF is the maximum stimulation frequency (in Hz) at which the heart is unable to follow stimulation (1.5×iT and 0.2 msec pulse width); VTt is the minimum pulse current (in μA) to evoke a sustained episode of VT (0.2 msec pulse width and 50 Hz) (Howard, P. G. and Walker, M. J. A., *Proc. West. Pharmacol. Soc.* 33: 123-127 (1990)).

Blood pressure (BP) and electrocardiographic (ECG) parameters are recorded and analyzed using LabView (National Instruments) with a customized autoanalysis software (Nortran Pharmaceuticals Inc.) to calculate mean BP (mmHg, ⅔ diastolic+⅓ systolic blood pressure), HR (bpm, 60/R—R interval); PR (msec, the interval from the beginning of the P-wave to the peak of the R-wave), ORS (msec, the interval from the beginning of the R-wave due to lack of Q wave in rat ECG, to the peak of the S-wave), QT (msec, the interval from the beginning of the R-wave to the peak of the T-wave).

The initial infusion dose is chosen based on a previous toxicology study of the test compound in conscious rats. This is an infusion dose that did not produce a 10% change from pre-drug levels in haemodynamic or ECG parameters.

The animal is left to stabilize prior to the infusion treatment according to a predetermined random and blind table. The initial infusion treatment is started at a rate of 0.5 mL/hr/300 g (i.e., 0.5 μmol/kg/min). Each infusion dose is doubled (in rate) every minutes. All experiments are terminated at 32 mL/hr/300 g (i.e., 32 μmol/kg/min). Electrical stimulation protocols are initiated during the last two minutes of each infusion level.

Responses to test compounds are calculated as percent changes from pre-infusion values; this normalization is used to reduce individual variation. The mean values of BP and ECG parameters at immediately before the electrical stimulation period (i.e., 3 min post-infusion) are used to construct cumulative dose-response curves. Data points are fit using lines of best fit with minimum residual sum of squares (least squares; SlideWrite program; Advanced Graphics Software, Inc.). $D_{25}$'s (infused dose that produced 25% change from pre-infusion value) are interpolated from individual cumulative dose-response curves and used as indicators for determining the potency of compounds of the present invention.

All of the U.S. patents, U.S. patent application publications, U.S. patent applications, foreign patents, foreign patent applications and non-patent publications referred to in this specification are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A prodrug represented by an ion channel modulating compound attached to a prodrug moiety, wherein the ion channel modulating compound is a compound of formula (IA), or a pharmaceutically acceptable salt, a stereoisomers or a stereoisomeric mixture thereof:

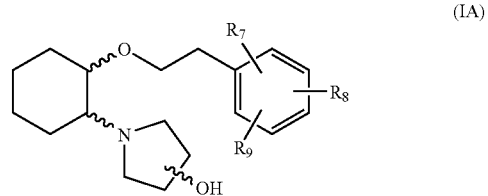

wherein, $R_7$, $R_8$ and $R_9$ are independently selected from hydrogen, hydroxy and $C_1$-$C_6$alkoxy, with the proviso that $R_7$, $R_8$ and $R_9$ cannot all be hydrogen;

wherein the prodrug moiety is selected from the group consisting of:

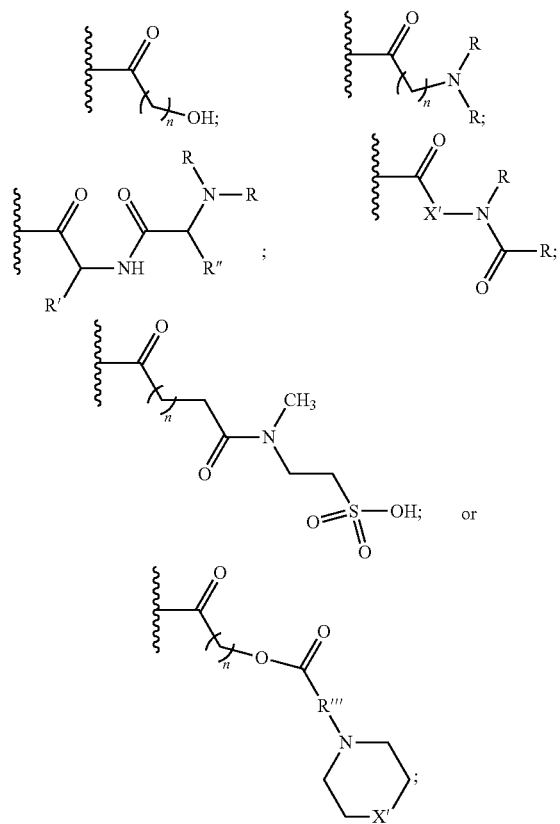

wherein:
each n is an integer from 1 to 10;
R' and R" are independently selected from hydrogen and $C_1$-$C_6$alkyl;
each R is independently selected from the group consisting of hydrogen, alkyl, substituted alkyl, alkenyl, substituted alkenyl, alkynyl and substituted alkynyl;
R'" is alkylene; and
each X' is independently selected from O, NH, S or $CH_2$; and
wherein at least one valency of the compound of formula (IA) is substituted with a bond to the prodrug moiety.

2. The prodrug of claim 1, wherein the ion channel modulating compound of formula (IA) is selected from the group consisting of the following:
(1R,2R)/(1S,2S)-2-[(3R)/(3S)-Hydroxypyrrolidinyl]-1-(3,4-dimethoxyphenethoxy)-cyclohexane;

(1R,2R)/(1S,2S)-2-[(3R)-hydroxypyrrolidinyl]-1-(3,4-dimethoxyphenethoxy)-cyclohexane;

(1R,2R)/(1S,2S)-2-[(3S)-hydroxypyrrolidinyl]-1-(3,4-dimethoxyphenethoxy)-cyclohexane;

(1R,2R)-2-[(3R)-hydroxypyrrolidinyl]-1-(3,4-dimethoxyphenethoxy)-cyclohexane;

(1R,2R)-2-[(3S)-hydroxypyrrolidinyl]-1-(3,4-dimethoxyphenethoxy)-cyclohexane;

(1R,2S)-2-[(3R)-hydroxypyrrolidinyl]-1-(3,4-dimethoxyphenethoxy)-cyclohexane;

(1R,2S)-2-[(3S)-hydroxypyrrolidinyl]-1-(3,4-dimethoxyphenethoxy)-cyclohexane;

(1S,2R)-2-[(3R)-hydroxypyrrolidinyl]-1-(3,4-dimethoxyphenethoxy)-cyclohexane;

(1S,2R)-2-[(3S)-hydroxypyrrolidinyl]-1-(3,4-dimethoxyphenethoxy)-cyclohexane;

(1S,2S)-2-[(3R)-hydroxypyrrolidinyl]-1-(3,4-dimethoxyphenethoxy)-cyclohexane;

(1S,2S)-2-[(3S)-hydroxypyrrolidinyl]-1-(3,4-dimethoxyphenethoxy)-cyclohexane; and (1R,2S)/(1S,2R)-2-[(3R)/(3S)-hydroxypyrrolidinyl]-1-(3,4-dimethoxyphenethoxy)-cyclohexane.

3. A pharmaceutical composition comprising a prodrug of claim 1 and a pharmaceutically acceptable excipient.

4. The prodrug of claim 1 of the formula (PRO-A), formula (PRO-A-Za) or formula (PRO-A-Zb):

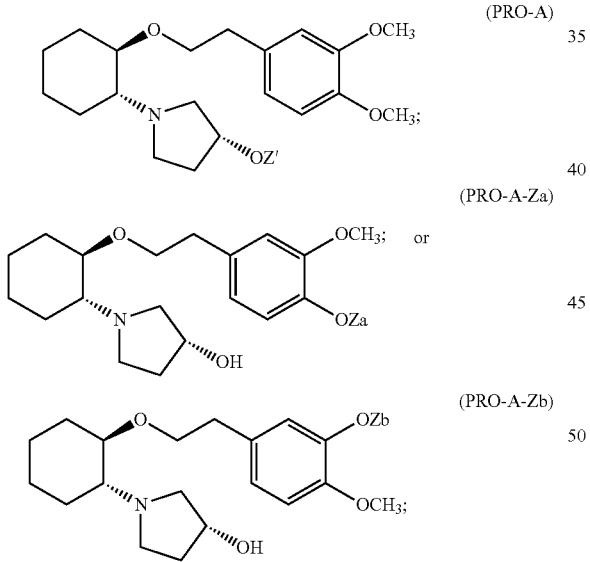

or a pharmaceutically acceptable salt thereof;
wherein Z', Za and Zb are independently selected from:

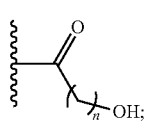 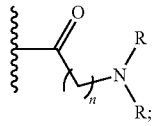

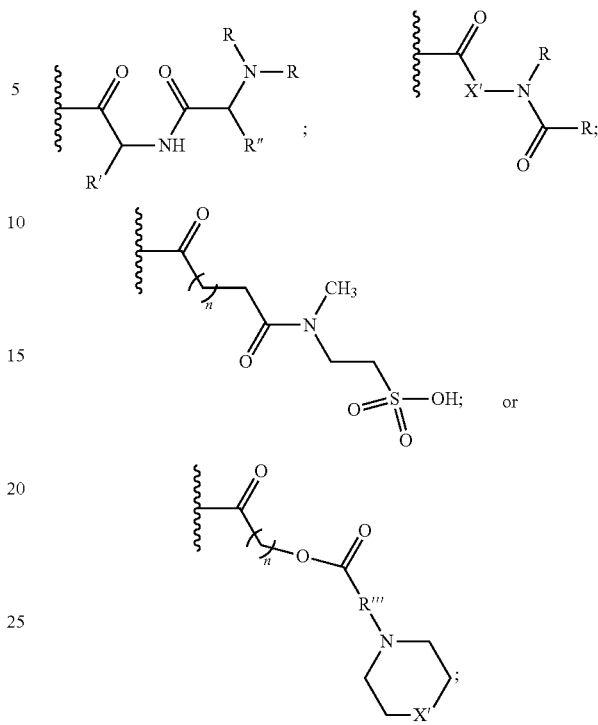

wherein:

each n is an integer from 1 to 10;

R' and R'' are independently selected from hydrogen and $C_1$-$C_6$alkyl;

each R is independently selected from the group consisting of hydrogen, alkyl, substituted alkyl, alkenyl, substituted alkenyl, alkynyl and substituted alkynyl;

R''' is alkylene; and each R'''' is independently selected from O, NH, S or $CH_2$.

5. The prodrug of claim 4 selected from:

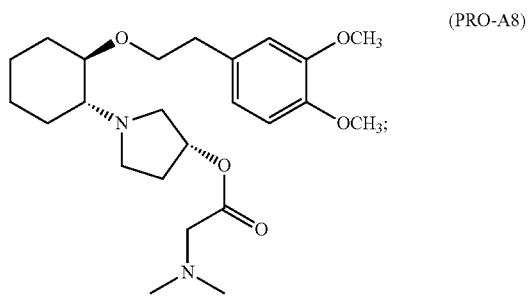

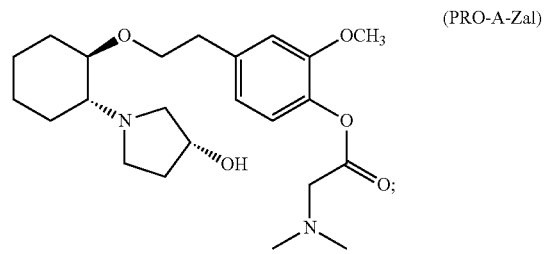

85
-continued

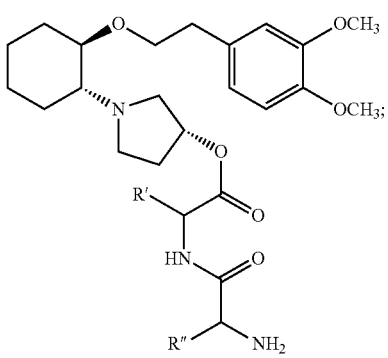
(PRO-A5)

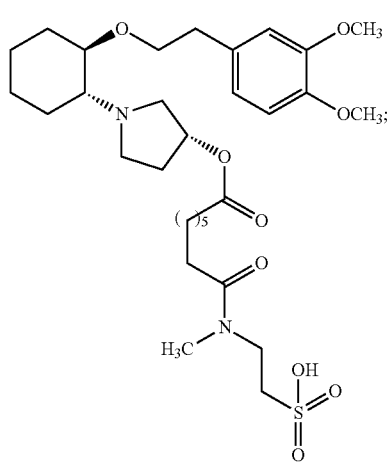
(PRO-A11)

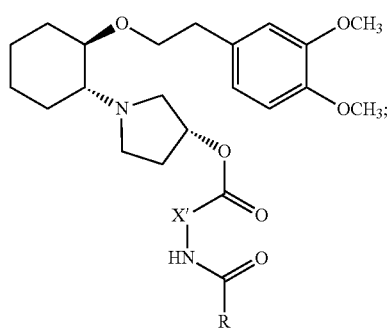
(PRO-A13)

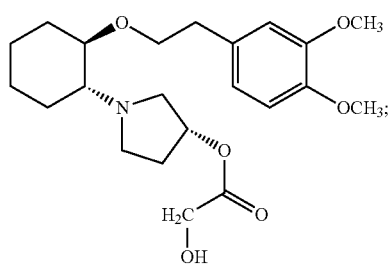
(PRO-A15) and

86
-continued

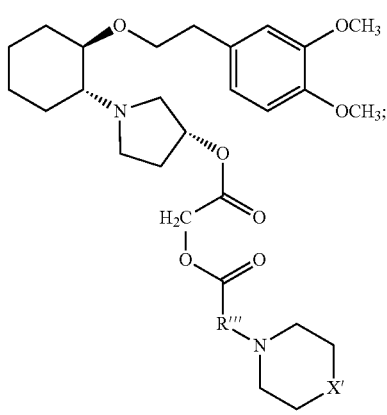
(PRO-A15)

or a pharmaceutically acceptable salt thereof.

6. The prodrug of claim 4 of formula (PRO-A):

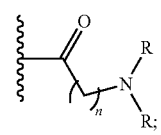
(PRO-A)

or a pharmaceutically acceptable salt thereof;

wherein Z' is

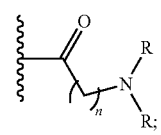

wherein:

n is an integer from 1 to 10; and each R is independently selected from the group consisting of hydrogen, alkyl, substituted alkyl, alkenyl, substituted alkenyl, alkynyl and substituted alkynyl.

7. The prodrug of claim 6 having the formula (PRO-A8):

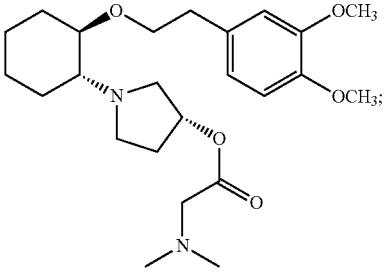
(PRO-A8)

or a pharmaceutically acceptable salt thereof.

8. The prodrug of claim 4 of formula (PRO-A-Za):

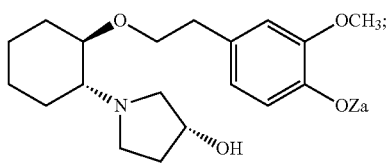
(PRO-A-Za)

or a pharmaceutically acceptable salt thereof;
wherein Za is

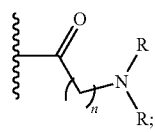

wherein:
n is an integer from 1 to 10; and
each R is independently selected from the group consisting of hydrogen, alkyl, substituted alkyl, alkenyl, substituted alkenyl, alkynyl and substituted alkynyl.

9. The prodrug of claim 7 of formula (PRO-A-Za1):

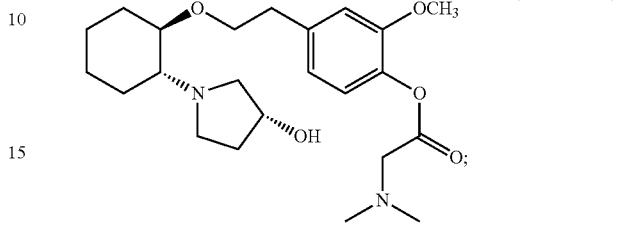
(PRO-A-Za1)

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,977,373 B2 | Page 1 of 2 |
| APPLICATION NO. | : 11/547423 | |
| DATED | : July 12, 2011 | |
| INVENTOR(S) | : Lewis Siu Leung Choi et al. | |

It is certified that error appears in the above-identified patent and that said Letters Patent is hereby corrected as shown below:

Title Page
Item 75, Inventors:
"Lewis Siu Leung Choi, Burnaby (CA); Doug Ta Hung Chou, Vancouver (CA); Allen W. Davidoff, Calgary (CA); Adewale Eniade, Coquitlam (CA); Bertrand M. C. Plouvier, Vancouver (CA)" should read, --Lewis Siu Leung Choi, Burnaby, BC (CA); Doug Ta Hung Chou, Vancouver, BC (CA); Allen W. Davidoff, Calgary, AB (CA); Adewale Eniade, Coquitlam, BC (CA); Bertrand M. C. Plouvier, Vancouver, BC (CA)--.

Item 56, Other Pubs:
"Amin et al., "RPR 101821, a new Potent Cholesterol-lowering Agent. Inhibition of Squalene Synthase and 7-Dehydrocholesterol Reductase", *Naunyn-Schmiedeberg's Arch Pharmacol* 353:233-240, 1996." should read, --Amin et al., "RPR 101821, a New Potent Cholesterol-lowering Agent: Inhibition of Squalene Synthase and 7-Dehydrocholesterol Reductase", *Naunyn-Schmiedeberg's Arch Pharmacol* 353:233-240, 1996.--.

Item 56, Other Pubs:
"Ginrich et al., "A New Class of Potent Vascular Endothelial Growth Factor Receptor Tyrosine Kinase Inhibitors: Structure-Activity Relationships for a Series of 9-Alkoxymethyl-12-(3-hydroxypropyl)indeno[2,1-α]pyrolo[3,4-c]carbazole-5-ones and the Identification of CEP-5214 and its Dimethylglycine Ester Prodrug Clinical Candidate CEP-7055," *J. Med. Chem.* 46:5375-5388, 2003." should read, --Ginrich et al., "A New Class of Potent Vascular Endothelial Growth Factor Receptor Tyrosine Kinase Inhibitors: Structure-Activity Relationships for a Series of 9-Alkoxymethyl-12-(3-hydroxypropyl)indeno[2,1-α]pyrrolo[3,4-c]carbazole-5-ones and the Identification of CEP-5214 and Its Dimethylglycine Ester Prodrug Clinical Candidate CEP-7055," *J. Med. Chem.* 46:5375-5388, 2003.--.

Signed and Sealed this
Twenty-ninth Day of November, 2011

David J. Kappos
*Director of the United States Patent and Trademark Office*

CERTIFICATE OF CORRECTION (continued)
U.S. Pat. No. 7,977,373 B2

Item 56, Other Pubs:
"Houssin et al., "A Convenient and General Method for the Preparation of *tert*-Butoxycarbonylaminoalkanenitriles and Their Conversion to Mono-tert-butoxycarbonlalkanediamines," *Synthesis:* 259-261, Mar. 1988." should read, --Houssin et al., "A Convenient and General Method for the Preparation of *tert*-Butoxycarbonylaminoalkanenitriles and Their Conversion to Mono-*tert*-butoxycarbonylalkanediamines," *Synthesis:* 259-261, Mar. 1988.--.

Item 56, Other Pubs:
"Steinbeck, "Proarrhythmische Wirkungen von Antiarrhythmika-Theoretische and Klinische Aspekte", *Z. Kardiol* 81(Supp 4):139-143, 1992." should read, --Steinbeck, "Proarrhythmische Wirkungen von Antiarrhythmika-Theoretische und Klinische Aspekte", *Z. Kardiol* 81(Supp 4): 139-143, 1992.--.

Column 84, Line 41:
"each R'" is independently selected from O, NH, S or $CH_2$." should read, --each X' is independently selected from O, NH, S, or $CH_2$.--.